United States Patent
Simons et al.

(10) Patent No.: US 12,275,960 B2
(45) Date of Patent: Apr. 15, 2025

(54) AAV-MEDIATED DELIVERY OF THERAPEUTIC ANTIBODIES TO THE INNER EAR

(71) Applicant: Akouos, Inc., Boston, MA (US)

(72) Inventors: Emmanuel John Simons, Brookline, MA (US); Robert Ng, Newton, MA (US); Michael McKenna, Boston, MA (US)

(73) Assignee: Akouos, Inc., Boston, MA (US)

( * ) Notice: Subject to any disclaimer, the term of this patent is extended or adjusted under 35 U.S.C. 154(b) by 0 days.

(21) Appl. No.: 18/209,041

(22) Filed: Jun. 13, 2023

(65) Prior Publication Data

US 2024/0101970 A1   Mar. 28, 2024

Related U.S. Application Data

(63) Continuation of application No. 16/955,715, filed as application No. PCT/US2018/066512 on Dec. 19, 2018, now abandoned.

(60) Provisional application No. 62/607,665, filed on Dec. 19, 2017.

(51) Int. Cl.
| | |
|---|---|
| *C12N 7/00* | (2006.01) |
| *A61K 9/00* | (2006.01) |
| *A61K 48/00* | (2006.01) |
| *A61P 27/16* | (2006.01) |
| *C07K 16/22* | (2006.01) |

(52) U.S. Cl.
CPC .............. *C12N 7/00* (2013.01); *A61K 9/0046* (2013.01); *A61K 48/005* (2013.01); *A61P 27/16* (2018.01); *C07K 16/22* (2013.01); *C12N 2750/14143* (2013.01)

(58) Field of Classification Search
CPC ..................................................... C12N 7/00
See application file for complete search history.

(56) References Cited

U.S. PATENT DOCUMENTS

| | | | |
|---|---|---|---|
| 4,797,368 A | 1/1989 | Carter et al. | |
| 4,816,567 A | 3/1989 | Cabilly et al. | |
| 5,122,458 A | 6/1992 | Post et al. | |
| 5,139,941 A | 8/1992 | Muzyczka et al. | |
| 5,168,062 A | 12/1992 | Stinski | |
| 5,478,745 A | 12/1995 | Samulski et al. | |
| 5,741,683 A | 4/1998 | Zhou et al. | |
| 5,952,221 A * | 9/1999 | Kurtzman | C12N 15/86 435/325 |
| 6,001,650 A | 12/1999 | Colosi | |
| 6,054,297 A | 4/2000 | Carter et al. | |
| 6,057,152 A | 5/2000 | Samulski et al. | |
| 6,156,303 A | 12/2000 | Russell et al. | |
| 6,204,059 B1 | 3/2001 | Samulski et al. | |
| 6,268,213 B1 | 7/2001 | Samulski et al. | |
| 6,407,213 B1 | 6/2002 | Carter et al. | |
| 6,491,907 B1 | 12/2002 | Rabinowitz et al. | |
| 6,660,514 B1 | 12/2003 | Zolotukhin et al. | |
| 6,884,879 B1 | 4/2005 | Baca et al. | |
| 6,951,753 B2 | 10/2005 | Shenk et al. | |
| 7,060,269 B1 | 6/2006 | Baca et al. | |
| 7,094,604 B2 | 8/2006 | Snyder et al. | |
| 7,169,901 B2 | 1/2007 | Baca et al. | |
| 7,172,893 B2 | 2/2007 | Rabinowitz et al. | |
| 7,201,898 B2 | 4/2007 | Monahan et al. | |
| 7,229,823 B2 | 6/2007 | Samulski et al. | |
| 7,282,199 B2 | 10/2007 | Gao et al. | |
| 7,297,334 B2 | 11/2007 | Baca et al. | |
| 7,365,166 B2 | 4/2008 | Baca et al. | |
| 7,439,065 B2 | 10/2008 | Ferrari et al. | |
| 7,485,291 B2 | 2/2009 | Fang et al. | |
| 7,498,024 B2 | 3/2009 | Fang et al. | |
| 7,588,772 B2 | 9/2009 | Kay et al. | |
| 7,612,181 B2 | 11/2009 | Wu et al. | |
| 7,662,623 B2 | 2/2010 | Fang et al. | |
| 7,709,224 B2 | 5/2010 | Fang et al. | |
| 7,714,119 B2 | 5/2010 | Fang et al. | |
| 7,790,449 B2 | 9/2010 | Gao et al. | |
| 8,258,268 B2 | 9/2012 | Wu et al. | |
| 8,513,390 B2 | 8/2013 | Stagliano et al. | |
| 8,586,714 B2 | 11/2013 | Ghayur et al. | |
| 8,716,450 B2 | 5/2014 | Ghayur et al. | |
| 8,722,855 B2 | 5/2014 | Ghayur et al. | |
| 8,735,546 B2 | 5/2014 | Ghayur et al. | |
| 8,822,645 B2 | 9/2014 | Ghayur et al. | |
| 8,962,804 B2 | 2/2015 | Williams et al. | |
| 9,079,953 B2 | 7/2015 | Harding et al. | |
| 9,453,241 B2 | 9/2016 | Pan | |
| 9,522,949 B2 | 12/2016 | Fang et al. | |
| 10,179,925 B2 | 1/2019 | Laird et al. | |

(Continued)

FOREIGN PATENT DOCUMENTS

| | | |
|---|---|---|
| CN | 102219859 A | 10/2011 |
| CN | 103143017 A | 6/2013 |

(Continued)

OTHER PUBLICATIONS

Adachi, K. et al., Drawing a high-resolution functional map of adeno-associated virus capsid by massively parallel sequencing, Nat Commun., 5:3075 (2014).

(Continued)

*Primary Examiner* — Albert M Navarro
(74) *Attorney, Agent, or Firm* — Choate, Hall & Stewart LLP; Stephanie L. Schonewald; Mandeep Kaur

(57) ABSTRACT

Provided herein are methods that include introducing into an inner ear of a mammal a therapeutically effective amount of an adeno-associated virus (AAV) vector that includes a nucleotide sequence encoding (a) a polypeptide including an antibody heavy chain variable domain operably linked to a signal peptide and a polypeptide including an antibody light chain variable domain operably linked to a signal peptide; (b) a polypeptide including an antigen-binding antibody fragment operably linked to a signal peptide; or (c) a soluble vascular endothelial growth factor receptor operably linked to a signal peptide.

15 Claims, 5 Drawing Sheets

Specification includes a Sequence Listing.

(56) References Cited

U.S. PATENT DOCUMENTS

| | | |
|---|---|---|
| 10,647,758 B2 | 5/2020 | Wilson et al. |
| 10,799,566 B2 | 10/2020 | High et al. |
| 11,197,937 B2 | 12/2021 | Tretiakova et al. |
| 11,697,801 B2 | 7/2023 | Simons et al. |
| 11,766,489 B2 | 9/2023 | Kirn et al. |
| 12,077,783 B2 | 9/2024 | Simons et al. |
| 12,084,503 B2 | 9/2024 | Gastwirt et al. |
| 12,122,844 B2 | 10/2024 | Crystal et al. |
| 2001/0034062 A1 | 10/2001 | Koenig |
| 2006/0018882 A1 | 1/2006 | Kaemmerer et al. |
| 2006/0040354 A1 | 2/2006 | O'Keefe |
| 2006/0110364 A1 | 5/2006 | Harding |
| 2006/0177819 A1 | 8/2006 | Smith et al. |
| 2007/0141029 A1 | 6/2007 | Brough |
| 2009/0215178 A1 | 8/2009 | Tang |
| 2009/0305344 A1 | 12/2009 | Polo et al. |
| 2010/0317096 A1 | 12/2010 | Fang et al. |
| 2010/0322931 A1 | 12/2010 | Harding et al. |
| 2011/0052576 A1 | 3/2011 | Ferrara et al. |
| 2011/0065779 A1 | 3/2011 | Fang et al. |
| 2013/0078260 A1 | 3/2013 | Cheeseman et al. |
| 2013/0090375 A1 | 4/2013 | Crystal et al. |
| 2015/0050243 A1 | 2/2015 | Kaczmarczyk et al. |
| 2015/0147317 A1 | 5/2015 | Robblee et al. |
| 2015/0182638 A1 | 7/2015 | Crystal et al. |
| 2015/0210771 A1 | 7/2015 | Crystal et al. |
| 2016/0024483 A1 | 1/2016 | Kim et al. |
| 2016/0243229 A1 | 8/2016 | Crystal et al. |
| 2016/0289314 A1 | 10/2016 | Shandilya et al. |
| 2017/0321214 A1 | 11/2017 | Zhang et al. |
| 2018/0311319 A1 | 11/2018 | Constable et al. |
| 2018/0369414 A1 | 12/2018 | Stankovic et al. |
| 2019/0060328 A1 | 2/2019 | Ibañez et al. |
| 2019/0060425 A1 | 2/2019 | Scheel et al. |
| 2019/0127455 A1 | 5/2019 | Simpson et al. |
| 2019/0211091 A1 | 7/2019 | Simpson et al. |
| 2019/0381194 A1 | 12/2019 | Tretiakova et al. |
| 2020/0277364 A1 | 9/2020 | Yoo et al. |
| 2020/0282077 A1 | 9/2020 | Kirn et al. |
| 2021/0071149 A1 | 3/2021 | Simons et al. |
| 2021/0171656 A1 | 6/2021 | Crystal et al. |
| 2021/0363499 A1 | 11/2021 | Simons et al. |
| 2022/0143221 A1 | 5/2022 | Danos et al. |
| 2022/0195462 A1 | 6/2022 | Danos et al. |
| 2022/0267739 A1 | 8/2022 | Simons et al. |
| 2022/0280608 A1 | 9/2022 | Pakola et al. |
| 2022/0288236 A1 | 9/2022 | Burns et al. |
| 2022/0288238 A1 | 9/2022 | Tretiakova et al. |
| 2023/0057380 A1 | 2/2023 | Gao et al. |
| 2023/0057519 A1 | 2/2023 | Simpson et al. |
| 2023/0075045 A1 | 3/2023 | Wang et al. |
| 2023/0295243 A1 | 9/2023 | Shi et al. |
| 2023/0295287 A1 | 9/2023 | Simons et al. |
| 2023/0372538 A1 | 11/2023 | Bee et al. |
| 2023/0414788 A1 | 12/2023 | Bee et al. |
| 2024/0024508 A1 | 1/2024 | Bee et al. |
| 2024/0335560 A1 | 10/2024 | Kirn et al. |
| 2024/0343791 A1 | 10/2024 | Dong et al. |

FOREIGN PATENT DOCUMENTS

| | | |
|---|---|---|
| CN | 103492574 A | 1/2014 |
| CN | 104994882 A | 10/2015 |
| CN | 106414487 A | 2/2017 |
| CN | 107074969 A | 8/2017 |
| EP | 2101807 B1 | 5/2016 |
| JP | 2017-510297 A | 4/2017 |
| WO | WO-92/022653 A1 | 12/1992 |
| WO | WO-96/037234 A1 | 11/1996 |
| WO | WO-97/09442 A1 | 3/1997 |
| WO | WO-98/10088 A1 | 3/1998 |
| WO | WO-98/45331 A2 | 10/1998 |
| WO | WO-00/28004 A1 | 5/2000 |
| WO | WO-01/059142 A1 | 8/2001 |
| WO | WO-2003/042397 A2 | 5/2003 |
| WO | WO-2004/113493 A2 | 12/2004 |
| WO | WO-2005/017149 A1 | 2/2005 |
| WO | WO-2005/033321 A2 | 4/2005 |
| WO | WO-05/073384 A2 | 8/2005 |
| WO | WO-06/12414 A2 | 2/2006 |
| WO | WO-2006/017325 A2 | 2/2006 |
| WO | WO-2006/110689 A2 | 10/2006 |
| WO | WO-2008/077077 A2 | 6/2008 |
| WO | WO-2011/104307 A2 | 9/2011 |
| WO | WO-2012/115980 A1 | 8/2012 |
| WO | WO-2013/173129 A2 | 11/2013 |
| WO | WO-2014/043480 A1 | 3/2014 |
| WO | WO-2014/178078 A2 | 11/2014 |
| WO | WO-2015/054653 A2 | 4/2015 |
| WO | WO-2015/123715 A1 | 8/2015 |
| WO | WO-2015/138616 A1 | 9/2015 |
| WO | WO-2015/142963 A1 | 9/2015 |
| WO | WO-2016/040441 A1 | 3/2016 |
| WO | WO-2017/040528 A1 | 3/2017 |
| WO | WO-2017/050825 A1 | 3/2017 |
| WO | WO-2017/075119 A1 | 5/2017 |
| WO | WO-2017/100791 A1 | 6/2017 |
| WO | WO-2017/117464 A1 | 7/2017 |
| WO | WO-2017/147265 A1 | 8/2017 |
| WO | WO-2017/180936 A1 | 10/2017 |
| WO | WO-2017/181021 A1 | 10/2017 |
| WO | WO-2017/218974 A2 | 12/2017 |
| WO | WO-2017/218981 A2 | 12/2017 |
| WO | WO-2019/067540 A1 | 4/2019 |
| WO | WO-2019/079496 A2 | 4/2019 |
| WO | WO-2019/104279 A1 | 5/2019 |
| WO | WO-2019/116349 A1 | 6/2019 |
| WO | WO-2019/126329 A1 | 6/2019 |
| WO | WO-2019/164854 A1 | 8/2019 |
| WO | WO-2020/097372 A1 | 5/2020 |
| WO | WO-2020/206098 A1 | 10/2020 |
| WO | WO-2020/219868 A1 | 10/2020 |
| WO | WO-2021/046245 A1 | 3/2021 |
| WO | WO-2021/071835 A1 | 4/2021 |
| WO | WO-2021/076794 A1 | 4/2021 |
| WO | WO-2021/108530 A1 | 6/2021 |
| WO | WO-2021/231808 A2 | 11/2021 |
| WO | WO-2021/255589 A1 | 12/2021 |
| WO | WO-2021/255590 A1 | 12/2021 |
| WO | WO-2022/018516 A1 | 1/2022 |
| WO | WO-2022/051537 A1 | 3/2022 |
| WO | WO-2022/076549 A1 | 4/2022 |
| WO | WO-2022/076591 A1 | 4/2022 |
| WO | WO-2022/076595 A1 | 4/2022 |
| WO | WO-2022/119839 A1 | 6/2022 |
| WO | WO-2022/240778 A1 | 11/2022 |
| WO | WO-2023/280157 A1 | 1/2023 |
| WO | WO-2023/284879 A1 | 1/2023 |
| WO | WO-2023/150142 A1 | 8/2023 |
| WO | WO-2023/155918 A1 | 8/2023 |
| WO | WO-2024/002076 A1 | 1/2024 |
| WO | WO-2024/222934 A1 | 10/2024 |

OTHER PUBLICATIONS

Ahn, S. et al., Intraocular pharmacokinetics of ranibizumab in vitrectomized versus nonvitrectomized eyes, *Invest Ophthalmol Vis Sci.*, 55(1):567-573 (2014).

Akil, O. et al., Dual AAV-mediated gene therapy restores hearing in a DFNB9 mouse model, *Proc Natl Acad Sci USA*, 116(10):4496-4501 (2019).

Akil, O. et al., Restoration of hearing in the VGLUT3 knockout mouse using virally mediated gene therapy, *Neuron*, 75(2):283-293 (2012).

Al-Moyed, H. et al., A dual-AAV approach restores fast exocytosis and partially rescues auditory function in deaf otoferlin knock-out mice, *EMBO Mol Med.*, 11(1):e9396 (2019).

Andersen, J. et al., Herpesvirus-Mediated Gene Delivery into the Rat Brain: Specificity and Efficiency of the Neuron-Specific Enolase Promoter, Cell Mol. Neurobiol., 13(5):503-515 (1993).

Andres-Mateos, E. et al., Optimized surgical approach leads to highly efficient AAV gene transfer to inner hair cells in rhesus

(56) References Cited

OTHER PUBLICATIONS macaque, *American Society of Gene and Cell Therapy Annual Meeting*, 22:676 (2019).
Ansari, S. et al., Surgery for vestibular schwannomas: a systematic review of complications by approach, *Neurosurg Focus*, 33(3):E14 (2012).
Arbuthnot, P. et al., In vitro and in vivo hepatoma cell-specific expression of a gene transferred with an adenoviral vector, Hum Gene Ther., 7(13):1503-1514 (1996).
Askew, C. et al., Tmc gene therapy restores auditory function in deaf mice, *Sci Transl Med.*, 7(295):295ra108 (2015).
Asokan, A. et al., The AAV Vector Toolkit: Poised at the Clinical Crossroads, Molecular Therapy, 20(4):699-708 (2012).
AveXis. 2019. Zolgensma US prescribing information. US Food and Drug Administration. https://www.fda.gov/media/126109/download. Accessed Aug. 31, 2020.
Bakri, S. J. et al., Pharmacokinetics of Intravitreal Ranibizumab (Lucentis), American Academy of Ophthalmology, 14(12):2179-2182 (2007).
Banaszynski, L. A. et al., A rapid, reversible, and tunable method to regulate protein function in living cells using synthetic small molecules, Cell, 126(5): 995-1004 (2012).
Bankoti, K. et al., Advances and challenges in adeno-associated viral inner-ear gene therapy for sensorineural hearing loss, Molecular Therapy: Methods & Clinical Development, 21:209-236 (2021).
Bartoli. M. et al., Noninvasive Monitoring of Therapeutic Gene Transfer in Animal Models of Muscular Dystrophies, Gene Ther. 13:20-28 (2006).
Batt, D. and Carmichael, G., Characterization of the polyomavirus late polyadenylation signal, Mol Cell Biol., 15(9):4783-4790 (1995).
Batt, D. B. and Carmichael, G. G., Characterization of the polyomavirus late polyadenylation signal, Mol. Cell Biol., 15(9):4783-4790 (1995).
Bennett, J. et al., AAV2 gene therapy readministration in three adults with congenital blindness, *Sci Transl Med.*, 4(120):120ra15 (2012).
Bohne, B. and Harding, G., Degeneration in the cochlea after noise damage: primary versus secondary events, Am J Otol., 21(4):505-509 (2000).
Bonne, N. et al., An allograft mouse model for the study of hearing loss secondary to vestibular schwannoma growth, *J Neurooncol.*, 129(1):47-56 (2016).
Boshart, M. et al., A very strong enhancer is located upstream of an immediate early gene of human cytomegalovirus, Cell, 41(2):521-530 (1985).
Brastianos, P. and Batchelor, T., VEGF inhibitors in brain tumors, Clin Adv Hematol Oncol., 7(11):753-768 (2009).
Bulankina, A. and Moser, T., Neural circuit development in the mammalian cochlea, *Physiology (Bethesda)*, 27(2):100-112 (2012).
Carlson, M. et al., A cross-sectional survey of the North American Skull Base Society: current practice patterns of vestibular schwannoma evaluation and management in North America, *J Neurol Surg B Skull Base*, 79(3):289-296 (2018).
Carlson, M. et al., Long-term quality of life in patients with vestibular schwannoma: an international multicenter cross-sectional study comparing microsurgery, stereotactic radiosurgery, observation, and nontumor controls, *J Neurosurg.*, 122(4):833-842 (2015).
Carneiro, A. et al., Vascular endothelial growth factor plasma levels before and after treatment of neovascular age-related macular degeneration with bevacizumab or ranibizumab, *Acta Ophthalmol.*, 90(1):e25-e30 (2012).
Carvalho, L. et al., Synthetic adeno-associated viral vector efficiently targets mouse and nonhuman primate retina in vivo, *Hum Gene Ther.*, 29(7):771-784 (2018).
Casset, F. et al., A peptide mimetic of an anti-CD4 monoclonal antibody by rational design, Biochem. Biophys. Res. Commun., 307(1):198-205 (2003).
Caye-Thomasen, P. et al. Immunohistochemical demonstration of vascular endothelial growth factor in vestibular schwannomas correlates to tumor growth rate, Laryngoscope, 113(12):2129-2134 (2003).
Caye-Thomasen, P. et al., VEGF and VEGF receptor-1 concentration in vestibular schwannoma homogenates correlates to tumor growth rate, Otol Neurotol., 26(1):98-101 (2005).
Chamney, S. et al., A mutation in the Norrie disease gene (NDP) associated with familial exudative vitreoretinopathy, Eye, 25(12):1658 (2011).
Chen, C. et al., mRNA decay mediated by two distinct AU-rich elements from c-fos and granulocyte-macrophage colony-stimulating factor transcripts: different deadenylation kinetics and uncoupling from translation, Mol Cell Biol., 15(10):5777-5788 (1995).
Chen, H. and Cleck, J., Adverse effects of anticancer agents that target the VEGF pathway, Nat Rev Clin Oncol., 6(8):465-477 (2009).
Chen, J. et al., A cerebellopontine angle mouse model for the investigation of tumor biology, hearing, and neurological function in NF2-related vestibular schwannoma, *Nat Protoc.*, 14(2):541-555 (2019).
Chen, J. et al., Expression of rat bone sialoprotein promoter in transgenic mice, J Bone Miner Res., 11(5):654-664 (1996).
Chen, Q. et al., An AU-rich element in the 3' untranslated region of the spinach chloroplast petD gene participates in sequence-specific RNA-protein complex formation, Mol Cell Biol., 15(4):2010-2018 (1995).
Chen, X. et al., HSV amplicon-mediated neurotrophin-3 expression protects murine spiral ganglion neurons from cisplatin-induced damage, *Mol Ther.*, 3(6):958-963 (2001).
Chen, Y. et al., Selection and Analysis of an Optimized Anti-VEGF Anitbody: Crystal Structure of an Affinity-matured Fab in Complex and Antigen, J. Mol. Biol., 293:865-881 (1999).
Chien, W. et al., Gene therapy restores hair cell stereocilia morphology in inner ears of deaf whirler mice, *Mol Ther.*, 24(1):17-25 (2016).
Christoforidis, J. et al., PET/CT imaging of I-124-radiolabeled bevacizumab and ranibizumab after intravitreal injection in a rabbit model, *Invest Ophthalmol Vis Sci.*, 52(8):5899-5903 (2011).
Clinicaltrials.gov. 2020a. NCT02132130: Safety, Tolerability and Efficacy for CGF166 in Patients with Unilateral or Bilateral Severe-to-profound Hearing Loss. National Institutes of Health. Accessed Aug. 31, 2020.
Clinicaltrials.gov. 2020b. NCT03066258: RGX-314 gene therapy for neovascular AMD trial. National Institutes of Health. Accessed Aug. 31, 2020.
Clinicaltrials.gov. 2020c. NCT03748784: ADVM-022 Intravitreal Gene Therapy for Wet Amd (Optic). National Institutes of Health. Accessed Aug. 31, 2020.
Clinicaltrials.gov. 2020d. NCT04418427: ADVM-022 Intravitreal Gene Therapy for DME (Infinity). National Institutes of Health. Accessed Aug. 31, 2020.
Colella, P. et al., Emerging issues in AAV-mediated in vivo gene therapy, *Mol Ther Methods Clin Dev.*, 8:87-104 (2018).
Cotten, M. et al., High-efficiency receptor-mediated delivery of small and large (48 kilobase gene constructs using the endosome-disruption activity of defective or chemically inactivated adenovirus particles, P.N.A.S. U.S.A., 89(13):6094-98 (1992).
Cromie, K. et al., Nanobodies and their Use in GPCR Drug Discovery, Curr. Top. Med. Chem., 15:2543-2557 (2016).
Curiel, D. T., High-efficiency gene transfer employing adenovirus-polylysine-DNA complexes, Nat Immun., 13(2-3):141-64 (1994).
Dai, C. et la., Rhesus cochlear and vestibular functions are pre-served after inner ear injection of saline volume sufficient for gene therapy delivery, J Assoc Res Otolaryngol., 18(4):601-617 (2017).
De Felipe, P. and Izqierdo, M., Tricistronic and tetracistronic retroviral vectors for gene transfer, Hum Gene Ther, 11(13):1921-1931 (2000).
De Felipe, P. et al., Use of the 2A sequence from foot-and-mouth disease virus in the generation of retroviral vectors for gene therapy, Gene Ther., 6(2):198-208 (1999).
De Fougerolles, A., Delivery vehicles for small interfering RNA in vivo, Hum Gene Ther., 19(2):125-132 (2008).
De Genst, E. et al., Antibody repertoire development in camelids, Dev Comp Immunol., 30(1-2):187-198 (2006).

(56) References Cited

OTHER PUBLICATIONS

De Meyer., T. et al., Nanobody-based products as research and diagnostic tools, Trends Biotechnol., 32(5):263-270 (2014).
Digiammarino, E. et al., Design and generation of DVD-Ig™ molecules for dual-specific targeting, Methods Mol Biol., 899:145-156 (2012).
Dilwali, S. et al., Secreted factors from human vestibular schwannomas can cause cochlear damage, Sci Rep., 5:18599 (2015).
Dinh, C. et al., A xenograft model of vestibular schwannoma and hearing loss, Otol Neurotol., 39(5):e362-e369 (2018).
Dmitriev, I. et al., An adenovirus vector with genetically modified fibers demonstrates expanded tropism via utilization of a coxsackievirus and adenovirus receptor-independent cell entry mechanism, J Virol., 72(12):9706-9713 (1998).
Doherty, J. and Friedman, R., Controversies in building a management algorithm for vestibular schwannomas, Curr Opin Otolaryngol Head Neck Surg., 14(5):305-313 (2006).
Failla, C. et al., Positive and Negative Regulation of Angiogenesis by Soluble Vascular Endothelial Growth Factor Receptor-1, Int J Mol Sci., 19(5):1306 (2018).
Fath, S. et al., Multiparameter RNA and Codon Optimization: A Stardardized Tool to Access and Enhance Autologous Mammalian Gene Expression, PLoS One, 6(3):e17596, 14 pages (2011).
FDA, Applying human factors and usability engineering to medical devices—guidance for industry and Food and Drug Administration staff. In, edited by Food and Drug Administration and Center for Devices and Radiological Health, 49 pages (Feb. 2016).
FDA, Design and analysis of shedding studies for virus or bacteria-based gene therapy and oncolytic products—guidance for industry. In, edited by Food and Drug Administration and Center for Biologics Evaluation and Research, 19 pages (Aug. 2015).
FDA, Evaluation of devices used with Regenerative Medicine Advanced Therapies—guidance for industry. In, edited by Food and Drug Administration, Center for Biologics Evaluation and Research, Center for Devices and Radiological Health and Office of Combination Products, 14 pages (Feb. 2019).
FDA, Principles of premarket pathways for combination products guidance for industry and FDA staff—draft guidance. In, edited by Food and Drug Administration, Office of Combination Products, Center for Biologics Evaluation and Research, Center for Drug Evaluation and Research and Center for Devices and Radiological Health, 24 pages (Feb. 2019).
FDA, Use of International Standard ISO 10993-1, "Biological evaluation of medical devices—Part 1: Evaluation and testing within a risk management process"—guidance for industry and Food and Drug Administration staff. In, edited by Food and Drug Administration and Center for Devices and Radiological Health, 68 pages (Sep. 2020).
Ferrara, N. et al., Bevacizumab (Avastin), a humanized anti-VEGF monoclonal antibody for cancer therapy, Biochem Biophys Res Commun., 333(2):328-335 (2005).
Fisher, K. et al., Transduction with recombinant adeno-associated virus for gene therapy is limited by leading-strand synthesis, J Virol., 70(1):520-532 (1996).
Flotte, T. et al., A phase I study of an adeno-associated virus-CFTR gene vector in adult CF patients with mild lung disease, Hum Gene Ther., 7(9):1145-1159 (1996).
Flotte, Terence R., Birth of a new therapeutic platform: 47 years of adeno-associated virus biology from virus discovery to licensed gene therapy, Mol Ther., 21(11):1976-1981 (2013).
Francis, S. et al., The adeno-associated viral Anc80 vector efficiently transduces inner ear cells in cynomolgus macaques (*Macaca fascicularis*), Association for Research in Otolaryngology Midwinter Meeting, 43:685 (2020).
Fujioka, M. et al., Inflammatory and immune responses in the cochlea: potential therapeutic targets for sensorineural hearing loss, Front Pharmacol., 5:287 (2014).
Furler, S. et al., Recombinant AAV vectors containing the foot and mouth disease virus 2A sequence confer efficient bicistronic gene expression in cultured cells and rat substantia nigra neurons, Gene Ther., 8(11):864-873 (2001).
Gaffen, S.L. and Liu, K.D., Overview of interleukin-2 function, production and clinical applications, Cytokine, 28:109-123 (2004).
Gao, G. et al., Clades of Adeno-associated viruses are widely disseminated in human tissues, J. Virol.. 78(12): 6381-6388 (2004).
Gao, X. et al., Anti-VEGF treatment improves neurological function and augments radiation response in NF2 schwannoma model, Proc Natl Acad Sci USA, 112(47):14676-14681 (2015).
Gao, Y. et al., The adeno-associated viral AAVAnc80 vector efficiently transduces inner ear cells in olive baboons (*Papio anubis*), Association for Research in Otolaryngology Midwinter Meeting, 43:680 (2020).
Garber, K., Bispecific antibodies rise again, Nat Rev Drug Discov., 13(11):799-801 (2014).
Gaudreault, J. et al., Preclinical pharmacokinetics of ranibizumab (rhuFabV2) after a single intravitreal administration, Invest Ophthalmol Vis Sci., 46(2):726-733 (2005).
Gehlhausen, J. et al., A murine model of neurofibromatosis type 2 that accurately phenocopies human schwannoma formation, Hum Mol Genet., 24(1):1-8 (2015).
Genentech. 2017. Lucentis US prescribing information. US Food and Drug Administration. https://www.accessdata.fda.gov/drugsatfda_docs/label/2017/125156s114lbl.pdf., 7 pages, Accessed Aug. 31, 2020.
Giovannini, M. et al., Conditional biallelic Nf2 mutation in the mouse promotes manifestations of human neurofibromatosis type 2, Genes Dev., 14(13):1617-1630 (2000).
Giovannini, M.et al., Schwann cell hyperplasia and tumors in transgenic mice expressing a naturally occurring mutant NF2 protein, Genes Dev., 13(8):978-986 (1999).
Glasscock, M. et al., Twenty-five years of experience with stapedectomy, Laryngoscope, 105(9 Pt 1):899-904 (1995).
Golfinos, J. et al., A matched cohort comparison of clinical outcomes following microsurgical resection or stereotactic radiosurgery for patients with small- and medium-sized vestibular schwannomas, J Neurosurg., 125(6):1472-1482 (2016).
Gossen, M. and Bujard, H., Tight control of gene expression in mammalian cells by tetracycline-responsive promoters, Proc Natl Acad Sci USA, 89(12):5547-5551 (1992).
Gossen, M. et al., Transcriptional activation by tetracyclines in mammalian cells, Science, 268(5218):1766-1769 (1995).
Gutmann, D. and Giovannini, M., Mouse models of neurofibromatosis 1 and 2, Neoplasia, 4(4):279-290 (2002).
Gyorgy, B. et al., Gene transfer with AAV9-PHP.B rescues hearing in a mouse model of Usher Syndrome 3A and transduces hair cells in a non-human primate, Mol Ther Methods Clin Dev., 13:1-13 (2019).
Halpin, C. et al., Self-processing 2A-polyproteins—a system for co-ordinate expression of multiple proteins in transgenic plants, Plant J., 17(4):453-45 (1999).
Hamernik, R. et al., Anatomical correlates of impulse noise-induced mechanical damage in the cochlea, Hear Res., 13(3):229-247 (1984).
Hanna, R. et al., Nephrotoxicity induced by intravitreal vascular endothelial growth factor inhibitors: emerging evidence, Kidney Int., 96(3):572-580 (2019).
Hansal, S. et al., Induction of antigen-specific hyporesponsiveness by transplantation of hemopoietic cells containing an MHC class I transgene regulated by a lymphocyte-specific promoter, J Immunol., 161(3):1063-1068 (1998).
Harvey, D. and Caskey, C., Inducible control of gene expression: prospects for gene therapy, Curr Opin Chem Biol., 2(4):512-518 (1998).
Haryadi, R. et al., Optimization of Heavy Chain and Light Chain Signal Peptides for High Level Expression of Therapeutic Antibodies in CHO Cells, PLOS One, 16 pages (2015).
Heidel, J. et al., Aministration in non-human primates of escalating intravenous doses of targeted nanoparticles containing ribonucleotide reductase subunit M2 siRNA, Proc Natl Acad Sci USA, 104(14):5715-5721 (2007).

(56) References Cited

OTHER PUBLICATIONS

Hellen, C. and Sarnow, P., Internal ribosome entry sites in eukaryotic mRNA molecules, Genes Dev., 15(13):1593-1612 (2001).
Huang, V. et al., Improvement in patient-reported hearing after treatment with bevacizumab in people with neurofibromatosis type 2, Otol Neurotol., 39(5):632-638 (2018).
Huang, X. et al., Spontaneous tumour shrinkage in 1261 observed patients with sporadic vestibular schwannoma, J Laryngol Otol., 127(8):739-743 (2013).
Hudry, E. et al., Efficient gene transfer to the central nervous system by single-stranded Anc80L65, Mol Ther Methods Clin Dev., 10:197-209 (2018).
Hu-Lieskovan, S. et al., Sequence-specific knockdown of EWS-FLI1 by targeted, nonviral delivery of small interfering RNA inhibits tumor growth in a murine model of metastatic Ewing's sarcoma, Cancer Res., 65(19):8984-8992 (2005).
Husseman, J. and Raphael, Y., Gene Therapy in the Inner Ear Using Adenovirus Vectors, Adv. Otorhinolaryngol., 66:37-51 (2009).
Hutton-Smith, L. et al., A mechanistic model of the intravitreal pharmacokinetics of large molecules and the pharmacodynamic suppression of ocular vascular endothelial growth factor levels by ranibizumab in patients with neovascular age-related macular degeneration, Mol Pharm., 13(9):2941-2950 (2016).
Ikeda, Y. et al., Efficient gene transfer to kidney mesenchymal cells using a synthetic adeno-associated viral vector, J Am Soc Nephrol., 29(9):2287-2297 (2018).
International Search Report for PCT/US2018/066512 (AAV-Mediated Delivery of Therapeutic Antibodies To the Inner Ear, filed Dec. 19, 2018), received from ISA/KR, 7 pages (Apr. 17, 2019).
International Search Report for PCT/US2021/061205, 6 pages (Mar. 31, 2022).
International Search Report for PCT/US2023/012083, filed Feb. 1, 2023, 7 pages, (mailed Jul. 18, 2023).
Isgrig, K. et al., AAV2.7m8 is a powerful viral vector for inner ear gene therapy, Nat. Commun., 10(1):427 (2019).
Ito, T. et al., SLC26A4 mutation testing for hearing loss associated with enlargement of the vestibular aqueduct, World J. Otorhinolaryngol., 3(2):26-34 (2013).
Iwamoto, M. et al., A general chemical method to regulate protein stability in the mammalian central nervous system. Chem Biol., 17(9): 981-988 (2010).
Jakob, C. et al., Structure reveals function of the dual variable domain immunoglobulin (DVD- Ig™) molecule, Mabs, (3):358-363 (2013).
Jung, J. et al., Secretion of soluble vascular endothelial growth factor receptor 1 (sVEGFR1/sFlt1) requires Arf1, Arf6, and Rab11 GTPases, PLoS One, 7(9):e44572, 11 pages (2012).
Kanaan, N. M. et al., Rationally Engineered AAV Capsids Improve Transduction and Volumetric Spread in the CNS, Mol. Ther. Nucleic Acids, 8:184-197 (2017).
Kapurch, J. et al., Temporal lobe gliosarcoma after gamma knife radiosurgery for vestibular schwannoma, Otol Neurotol., 37(8):1143-1147 (2016).
Karajannis, M. et al., Sustained imaging response and hearing preservation with low-dose bevacizumab in sporadic vestibular schwannoma, Neuro Oncol., 21(6):822-824 (2019).
Karch-Georges, A. et al., MRI of endolymphatic hydrops in patients with vestibular schwannomas: a case-controlled study using non-enhanced T2-weighted images at 3 Teslas, Eur Arch Otorhinolaryngol., 276(6):1591-1599 (2019).
Kaul, V. and Cosetti, M., Management of vestibular schwannoma (including NF2): facial nerve considerations, Otolaryngol Clin North Am., 51(6):1193-1212 (2018).
Kelleher, Z. T. and Vos, J. M., Long-term episomal gene delivery in human lymphoid cells using human and avian adenoviral-assisted transfection, Biotechniques, 17(6):1110-17 (1994).
Kendall, R. et al,. Identification of a Natural Soluble Form of the Vascular Endothelial Growth Factor Receptor, FLT-1, and Its Heterodimerization with KDR, Biochem Biophys Res Commun. 226:324-328 (1996).

Kendall. R. et al., Identification of a natural soluble form of the vascular endothelial growth factor receptor, FLT-1, and its heterodimerization with KDR, Biochem Biophys Res Commun, 226(2):324-328 (1996).
Kendall., R. and Thomas, K., Inhibition of vascular endothelial cell growth factor activity by an endogenously encoded soluble receptor, Proc Natl Acad Sci USA, 90(22):10705-10709 (1993).
Kijanka, M. et al., Nanobody-based cancer therapy of solid tumors, Nanomedicine (Lond)., 10(1):161-174 (2015).
Killeen, D. et al., Long-term effects of bevacizumab on vestibular schwannoma volume in neurofibromatosis type 2 patients, J Neurol Surg B Skull Base, 80(5):540-546 (2019).
Kim, H. et al., FcRn receptor-mediated pharmacokinetics of therapeutic IgG in the eye, Mol Vis., 15:2803-2812 (2009).
Kim, M. et al., Methionine sulfoxide reductase B3-targeted in utero gene therapy rescues hearing function in a mouse model of congenital sensorineural hearing loss, Antioxid Redox Signal, 24(11):590-602 (2016).
Kim, M. et al., Targeted gene delivery into the mammalian inner ear using synthetic serotypes of adeno-associated virus vectors, Mol Ther Methods Clin Dev., 13:197-204 (2019).
Kirchmann, M. et al., Ten-year follow-up on tumor growth and hearing in patients observed with an intracanalicular vestibular schwannoma, Neurosurgery, 80(1):49-56 (2017).
Klettner, A. and Roider, J., Comparison of bevacizumab, ranibizumab, and pegaptanib in vitro: efficiency and possible additional pathways, Invest Ophthalmol Vis Sci., 49(10):4523-4527 (2008).
Klump, H. et al., Retroviral vector-mediated expression of HoxB4 in hematopoietic cells using a novel coexpression strategy, Gene Ther., 8(10):811-817 (2001).
Koen, N. et al., Location of small intracanalicular vestibular schwannomas based on magnetic resonance imaging, Otolaryngol Head Neck Surg., 162(2):211-214 (2020).
Kondziolka, D. et al., The newly diagnosed vestibular schwannoma: radiosurgery, resection, or observation?, Neurosurg Focus, 33(3):E8 (2012).
Konishi, T. et al., Effects of chemical alteration in the endolymph on the cochlear potentials, Acta Otolaryngol., 62(4):393-404 (1966).
Koutsimpelas, D. et al., Expression of vascular endothelial growth factor and basic fibroblast growth factor in sporadic vestibular schwannomas correlates to growth characteristics, Otol Neurotol., 28(8):1094-1099 (2007).
Koutsimpelas, D. et al., The VEGF/VEGF-R axis in sporadic vestibular schwannomas correlates with irradiation and disease recurrence, ORL J Otorhinolaryngol Relat Spec., 74(6):330-338 (2012).
Kovaleva, M. et al., Shark variable new antigen receptor biologics—a novel technology platform for therapeutic drug development, Expert Opin Biol Ther., 14(10):1527-1539 (2014).
Krah, S. et al., Single-domain antibodies for biomedical applications, Immunopharmacol Immunotoxicol., 38(1):21-28 (2016).
Kshettry, V. et al., Incidence of vestibular schwannomas in the United States, J Neurooncol., 124(2):223-228 (2015).
Kujawa, S. and Liberman, M. et al., Synaptopathy in the noise-exposed and aging cochlea: Primary neural degeneration in acquired sensorineural hearing loss, Hear Res., 330(Pt B):191-199 (2015).
Landegger, L. et al., A synthetic AAV vector enables safe and efficient gene transfer to the mammalian inner ear, Nat Biotechnol., 35(3):280-284 (2017).
Leabman, M. et al., Effects of altered Fc?R binding on antibody pharmacokinetics in cynomolgus monkeys, Mabs, 5(6):896-903 (2013).
Lees, K. et al., Natural history of sporadic vestibular schwannoma: a volumetric study of tumor growth, Otolaryngol Head Neck Surg., 159(3):535-542 (2018).
Levitt, N. et al., Definition of an efficient synthetic poly(A) site, Genes Dev., 3(7):1019-1025 (1989).
Li, S. et al., Effective electrophoretic mobilities and charges of anti-VEGF proteins determined by capillary zone electrophoresis, J Pharm Biomed Anal., 55(3):603-607 (2011).
Li, W. et al., Engineering and selection of shuffled AAV genomes: a new strategy for producing targeted biological nanoparticles, Mol. Ther. 16(7):1252-1260 (2008).

(56) References Cited

OTHER PUBLICATIONS

Lichtenbeld, H. et al., Effect of local anti-VEGF antibody treatment on tumor microvessel permeability, *Microvasc Res.*, 57(3):357-362 (1999).
Litovsky, Ruth, Development of the auditory system, *Handb Clin Neurol.*, 129:55-72 (2015).
Littman, T. et al., The quinoxalinediones DNOX, CNOX and two related congeners suppress hair cell-to-auditory nerve transmission, *Hear Res.*, 40(1-2):45-53 (1989).
Liu, H. et al., Current strategies for drug delivery to the inner ear, Acta Pharmaceutica Sinica B, 3(2):86-96 (2013).
Liu, Y. et al., AAV8-antiVEGFfab Ocular Gene Transfer for Neovascular Age-Related Macular Degeneration, Molecular Therapy, 26(2):542-549 (2017).
Liu, Y. et al., Promoter effects of adeno-associated viral vector for transgene expression in the cochlea in vivo, Experimental and Molecular Medicine, 39(2): 170-175 (2007).
London, N.R. et al., The role of vascular endothelial growth factor and vascular stability in diseases of the ear, The Laryngoscope, 124:E340-E346 (2014).
Lu, V. et al., Efficacy and safety of bevacizumab for vestibular schwannoma in neurofibromatosis type 2: a systematic review and meta-analysis of treatment outcomes, *J Neurooncol.*, 144(2):239-248 (2019).
Lysaght, A. et al., Proteome of human perilymph, *J Proteome Res.*, 10(9):3845-3851 (2011).
MacCallum, R.M. et al., Antibody-antigen interactions: contact analysis and binding site topography, J. Mol. Biol., 262(5):732-745 (1996).
MacKeith, S. et al., Trends in acoustic neuroma management: a 20-year review of the oxford skull base clinic, *J Neurol Surg B Skull Base*, 74(4):194-200 (2013).
Magari, S. et al., Pharmacologic control of a humanized gene therapy system implanted into nude mice, J Clin Invest., 100(11):2865-2872 (1997).
Mahmud, M. et al., Histopathology of the inner ear in unoperated acoustic neuroma, *Ann Otol Rhinol Laryngol.*, 112(11):979-986 (2003).
Maier, P. et al., Retroviral vectors for gene therapy, Future Microbiol., 5(10):1507-1523 (2010).
Manley, Geoffrey A., Comparative auditory neuroscience: understanding the evolution and function of ears, *J Assoc Res Otolaryngol.*, 18(1):1-24 (2017).
Mattion, N. et al., Foot-and-mouth disease virus 2A protease mediates cleavage in attenuated Sabin 3 poliovirus vectors engineered for delivery of foreign antigens, J Virol., 70(11):8124-8127 (1996).
McClatchey, A. et al., Mice heterozygous for a mutation at the Nf2 tumor suppressor locus develop a range of highly metastatic tumors, *Genes Dev.*, 12(8):1121-1133 (1998).
McClatchey, A. et al., The Nf2 tumor suppressor gene product is essential for extraembryonic development immediately prior to gastrulation, *Genes Dev.*, 11(10):1253-1265 (1997).
Miyazaki, J. et al., Expression vector system based on the chicken beta-actin promoter directs efficient production of interleukin-5, *Gene*, 79(2):269-277 (1989).
Morrison, S. et al., Chimeric human antibody molecules: mouse antigen-binding domains with human constant region domains, Proc Natl Acad Sci USA, 81(21):6851-6855 (1984).
Mujic-Delic, A. et al., GPCR-targeting nanobodies: attractive research tools, diagnostics, and therapeutics, Trends Pharmacol Sci., 35(5):247-255 (2014).
Murillo, O. et al., Liver expression of a miniATP7B gene results in long-term restoration of copper homeostasis in a Wilson disease model in mice, *Hepatology*, 70(1):108-126 (2019).
Muyldermans, S. et al., Recognition of antigens by single-domain antibody fragments: the superfluous luxury of paired domains, Trends Biochem Sci., 26(4):230-235 (2001).
Muyldermans, S., Nanobodies: natural single-domain antibodies, Ann. Rev. Biochem. 82:775-797 (2013).
Muyldermans, S., Single domain camel antibodies: current status, J. Biotechnol., 74(4):277-302 (2001).
Muzyczka, N., Use of Adeno-Associated Virus as a General Transduction Vector for Mammalian Cells, Curr. Top Microbiol. Immunol., 158:97-129 (1992).
Naganawa, S. et al., Endolympathic hydrops in patients with vestibular schwannoma: visualization by non-contrast-enhanced 3D Flair, *Neuroradiology*, 53(12):1009-1015 (2011).
Niwa, H. et al., Efficient selection for high-expression transfectants with a novel eukaryotic vector, *Gene*, 108(2):193-199 (1991).
No Author Listed, High-dose AAV gene therapy deaths, *Nat Biotechnol.*, 38(8):910 (2020).
No, D. et al., Ecdysone-inducible gene expression in mammalian cells and transgenic mice, Proc Natl Acad Sci USA, 93(8):3346-3351 (1996).
Nuttall, A. et al., Acute perilymphatic perfusion of the guinea pig cochlea, *Hear Res.*, 6(2):207-221 (1982).
Omichi, R. et al., Hair cell transduction efficiency of single- and dual-AAV serotypes in adult murine cochleae, Mol Ther Methods Clin Dev., 17:1167-1177 (2020).
Orban, T. et al., Applying a "double-feature" promoter to identify cardiomyocytes differentiated from human embryonic stem cells following transposon-based gene delivery, *Stem Cells*, 27(5):1077-1087 (2009).
Orkin, S. et al., Thalassemia due to a mutation in the cleavage-polyadenylation signal of the human beta-globin gene, EMBO J., 4(2):453-456 (1985).
Ostrom, Q. et al., CBTRUS statistical report: primary brain and other central nervous system tumors diagnosed in the United States in 2011-2015, *Neuro Oncol.*, 20(suppl_4):iv1-iv86 (2018).
Paldor, I. et al., Growth rate of vestibular schwannoma, *J Clin Neurosci.*, 32:1-8 (2016).
Pan, B. et al., Gene therapy restores auditory and vestibular function in a mouse model of Usher syndrome type 1c, *Nat Biotechnol.*, 35(3):264-272 (2017).
Papadopoulos, N. et al., Binding and neutralization of vascular endothelial growth factor (VEGF) and related ligands by VEGF Trap, ranibizumab and bevacizumab, *Angiogenesis*, 15(2):171-185 (2012).
Pararas, E. et al., Kinetics of reciprocating drug delivery to the inner ear, *J Control Release*, 152(2):270-277 (2011).
Parente, V. and Corti, S., Advances in spinal muscular atrophy therapeutics, *Ther Adv Neurol Disord.*, 11:1-13 (2018).
Pedrosa, C. et al., Determinants and impact of headache after acoustic neuroma surgery, *Am J Otol.*, 15(6):793-797 (1994).
Pelletier, J. et al., Cap-independent translation of poliovirus mRNA is conferred by sequence elements within the 5' noncoding region., Mol. Cell. Biol. 8(3):1103-1112 (1988).
Peris-Celda, M. et al., Main symptom that led to medical evaluation and diagnosis of vestibular schwannoma and patient-reported tumor size: cross-sectional study in 1,304 patients, *J Neurol Surg B Skull Base*, 80(3):316-322 (2019).
Peyre, M. et al., Conservative management of bilateral vestibular schwannomas in neurofibromatosis type 2 patients: hearing and tumor growth results, *Neurosurgery*, 72(6):907-914 (2013).
Piccioli, P. et al., Neuroantibodies: ectopic expression of a recombinant anti-substance P antibody in the central nervous system of transgenic mice, Neuron, 15(2):373-384 (1995).
Piccioli, P. et al., Neuroantibodies: molecular cloning of a monoclonal antibody against substance P for expression in the central nervous system, Proc Natl Acad Sci USA, 88(13):5611-5615 (1991).
Plotkin, S. et al., Bevacizumab for progressive vestibular schwannoma in neurofibromatosis type 2: a retrospective review of 31 patients, Otol Neurotol., 33(6):1046-1052 (2012).
Plotkin, S. et al., Hearing improvement after bevacizumab in patients with neurofibromatosis type 2, *N Engl J Med.*, 361(4):358-367 (2009).
Plotkin, S. et al., Multicenter, prospective, phase II and biomarker study of high-dose bevacizumab as induction therapy in patients with neurofibromatosis type 2 and progressive vestibular schwannoma, *J Clin Oncol.*, 37(35):3446-3454 (2019).

(56) References Cited

OTHER PUBLICATIONS

Poulin, K. et al., Retargeting of adenovirus vectors through genetic fusion of a single-chain or single-domain antibody to capsid protein IX, J Virol., 84(19):10074-10086 (2010).
Proudfoot, N. et al., Integrating mRNA processing with transcription, Cell, 108(4):501-512 (2002).
Pryadkina, M. et al., A Comparison of AAV Strategies Distinguishes Overlapping Vectors for Efficient Systemic Delivery of the 6.2 Kb Dysferlin Coding Sequence, Meth. Clin. Devel. 2:15009 (2015).
Quesnel, A. et al., Otosclerosis: temporal bone pathology, *Otolaryngol Clin North Am.*, 51(2):291-303 (2018).
Rahbarizadeh, F. et al., Nanobody; an old concept and new vehicle for immunotargeting, Immunol Invest., 40(3):299-338 (2011).
Rask-Andersen, H. et al., Perilymph/modiolar communication routes in the human cochlea, *Ear Hear.*, 27(5):457-465 (2006).
Reid, C. et al., Development of an inducible anti-VEGF rAAV gene therapy strategy for the treatment of wet AMD, Scientific Reports, 8(1): p. 11763 (2018).
Remenschneider, A. et al., Is the cause of sensorineural hearing loss in patients with facial schwannomas multifactorial?, *Laryngoscope*, 127(7):1676-1682 (2017).
Reznitsky, M. et al., Epidemiology of vestibular schwannomas— prospective 40-year data from an unselected national cohort, *Clin Epidemiol.*, 11:981-986 (2019).
Roesch, S. et al., Functional Testing of SLC26A4 Variants-Clinical and Molecular Analysis of a Cohort with Enlarged Vestibular Aqueduct from Austria, Int. J. Mol. Sci. 19(1):209 (2018).
Ronzitti, G. et al., Human immune responses to adeno-associated virus (AAV) Vectors, *Front Immunol.*, 11:670 (2020).
Roosli, C. et al., Dysfunction of the cochlea contributing to hearing loss in acoustic neuromas: an underappreciated entity, *Otol Neurotol.*, 33(3):473-480 (2012).
Rozema, D. et al., Dymanic PolyConjugates for targeted in vivo delivery of siRNA to hepatocytes, Proc Natl Acad Sci USA, 104(32):12982-12987 (2007).
Rudikoff, S. et al., Single amino acid substitution altering antigen-binding specificity, Proc. Natl. Acad. Sci. USA, 79:1979-1983 (1982).
Russell, S. et al., Efficacy and safety of voretigene neparvovec (AAV2-hRPE65v2) in patients with RPE65-mediated inherited retinal dystrophy: a randomised, controlled, open-label, phase 3 trial, *Lancet*, 390(10097):849-860 (2017).
Ryan, A et al., Cellular targeting for cochlear gene therapy, Adv Otorhinolaryngol., 66:99-115 (2009).
Ryan, M. and Drew, J., Foot-and-mouth disease virus 2A oligopeptide mediated cleavage of an artificial polyprotein, EMBO J., 13(4):928-933 (1994).
Saito, K. et al., Expression of Ki-67 antigen and vascular endothelial growth factor in sporadic and neurofibromatosis type 2-associated schwannomas, *Clin Neuropathol.*, 22(1):30-34 (2003).
Sampath, P. et al., Facial nerve injury in acoustic neuroma (vestibular schwannoma) surgery: etiology and prevention, *J Neurosurg.*, 87(1):60-66 (1997).
Sandig, V. et al., HBV-derived promoters direct liver-specific expression of an adenovirally transduced LDL receptor gene, Gene Ther., 3(11):1002-1009 (1996).
Sanofi-Aventis US. 2020. Zaltrap US prescribing information. US Food and Drug Administration. https://www.accessdata.fda.gov/drugsatfda_docs/label/2020/125418s047lbl.pdf. Accessed Aug. 31, 2020.
Sardhara, J. et al., Postoperative tinnitus after vestibular schwannoma surgery: a neglected entity, *Neurol India*, 68(2):333-339 (2020).
Schek, N. et al.,Definition of the Upstream Efficiency Element of the Simian Virus 40 Late Polyadenylation Signal by Using in Vitro Analyses, Mol. Cell Biol., 12(12):5386-5393 (1992).
Schmidt-Erfurth, Ursula, Clinical safety of ranibizumab in age-related macular degeneration, *Expert Opin Drug Saf.*, 9(1):149-165 (2010).
Schnurman, Z. et la., Volumetric growth rates of untreated vestibular schwannomas, *J Neurosurg.*, 1-7 (2019).
Seol, H. et al., Optimal extent of resection in vestibular schwannoma surgery: relationship to recurrence and facial nerve preservation, *Neurol Med Chir* (Tokyo), 46(4):176-181 (2006).
Sharma, A. et al., Transduction efficiency of AAV 2/6, 2/8 and 2/9 vectors for delivering genes in human corneal fibroblasts, Brain Res Bull., 81(2-3):273 (2010).
Shepherd, R. et al., Cochlear pathology following reimplantation of a multichannel scala tympani electrode array in the macaque, *Am J Otol.*, 16(2):186-199 (1995).
Shu, Y. et al., Adenovirus vectors target several cell subtypes of mammalian inner ear in vivo, *Neural Plast.*, 2016:1-8 (2016).
Shu, Y. et al., Identification of Adeno-Associated Viral Vectors That Target Neonatal and Adult Mammalian Inner Ear Cell Subtypes, Hum Gene Ther., 27(9):687-99 (2016).
Skolnick, J. and Fetrow, U.S., From genes to protein structure and function: novel applications of computational approaches in the genomic era, Trends Biotechnol., 18(1):34-39 (2000).
Slattery, W. et al., Vestibular schwannoma growth rates in neurofibromatosis type 2 natural history consortium subjects, *Otol Neurotol.*, 25(5):811-817 (2004).
Spark Therapeutics. 2017. Luxturna US prescribing information. US Food and Drug Administration. https://www.fda.gov/media/109906/download, 16 pages, Accessed Aug. 31, 2020.
Sridhar, T. et al., A novel cholinergic "slow effect" of efferent stimulation on cochlear potentials in the guinea pig, *J Neurosci.*, 15(5 Pt 1):3667-3678 (1995).
Srinivasan, M. et al., Effect of fixatives and tissue processing on the content and integrity of nucleic acids, *Am J Pathol.*, 161(6):1961-1971 (2002).
Stein, G. et al., The osteocalcin gene: a model for multiple parameters of skeletal-specific transcriptional control, Mol Biol Rep., 24(3):185-196 (1997).
Sullivan, J. et al., Convective forces increase rostral delivery of intrathecal radiotracers and antisense oligonucleotides in the cynomolgus monkey nervous system, *J Transl Med.*, 18(1):309 (2020).
Suzuki, J. et al., Cochlear gene therapy with ancestral AAV in adult mice: complete transduction of inner hair cells without cochlear dysfunction, *Sci Rep.*, 7:45524, pp. 1-11 (2017).
Suzuki, J. et al., Round-window delivery of neurotrophin 3 regenerates cochlear synapses after acoustic overexposure, Sci Rep., 6:24907, 11 pages (2016).
Szymanski, P. et al., Development and validation of a robust and versatile one-plasmid regulated gene expression system, Mol Ther., 15(7):1340-1347 (2007).
Talaei, S. et la., Dye tracking following posterior semicircular canal or round window membrane injections suggests a role for the cochlea aqueduct in modulating distribution, *Front Cell Neurosci.*, 13:471, 16 pages (2019).
Tandon, V. et al., Microfabricated infuse-withdraw micropump component for an integrated inner-ear drug-delivery platform, *Biomed Microdevices*, 17(2):37 (2015).
Tandon, V. et al., Microfabricated reciprocating micropump for intracochlear drug delivery with integrated drug/fluid storage and electronically controlled dosing, *Lab Chip.*, 16(5):829-846 (2016).
Tao, Y. et al., Delivery of adeno-associated virus vectors in adult mammalian inner-ear cell subtypes without auditory dysfunction, *Hum Gene Ther.*, 29(4):492-506 (2018).
Thein, S. et al., The polyadenylation site mutation in the alpha-globin gene cluster, Blood, 71(2):313-319 (1988).
Tian, Y. et al., Creation of a transgenic mouse for hair-cell gene targeting by using a modified bacterial artificial chromosome containing Prestin, Dev Dyn., 231(1):199-203 (2004).
Timmers, A. et al., Ocular inflammatory response to intravitreal injection of adeno-associated virus vector: relative contribution of genome and capsid, *Hum Gene Ther.*, 31(1-2):80-89 (2020).
Torres Maldonado, S. et al., Recent trends in vestibular schwannoma management: an 11-year analysis of the National Cancer Database, *Otolaryngol Head Neck Surg.*, 161(1):137-143 (2019).
Trapani, I., et al., Effective delivery of large genes to the retina by dual AAV vectors, EMBO Mol Med., 6(2):194-211 (2014).

(56) References Cited

OTHER PUBLICATIONS

Tschudi, D. et al., Conservative management of unilateral acoustic neuromas, *Am J Otol.*, 21(5):722-728 (2000).
Vajdos, F.F. et al., Comprehensive functional maps of the antigen-binding site of an anti-ErbB2 antibody obtained with shotgun scanning mutagenesis, J. Mol. Biol., 320(2)415-428 (2002).
Valentini, C. et al., Inner Ear Gene Delivery: Vectors and Routes, Hearing Balance Commun., 18(4):278-285 (2020).
Van Audenhove, I. and Gettemans, J., Nanobodies as Versatile Tools to Understand, Diagnose, Visualize and Treat Cancer, EBioMedicine, 8:40-48 (2016).
Van Bockstaele, F. et al., The development of nanobodies for therapeutic applications, Curr Opin Investig Drugs, 10(11):1212-1224 (2009).
Vincke, C. and Muyldermans, S. Introduction to heavy chain antibodies and derived Nanobodies, Methods Mol Biol., 911:15-26 (2012).
Vitosevic, K. et al., Effect of formalin fixation on por amplification of DNA isolated from healthy autopsy tissues, *Acta Histochem*, 120(8):780-788 (2018).
Wang, D. et al., Adeno-associated virus vector as a platform for gene therapy delivery, *Nat Rev Drug Discov.*, 18(5):358-378 (2019).
Wang, L. et al., Single stranded adeno-associated virus achieves efficient gene transfer to anterior segment in the mouse eye, *PLoS One*, 12(8):e0182473, pp. 1-12 (2017).
Wang, Y. et al., Ligand-inducible and liver-specific target gene expression in transgenic mice, Nat Biotechnol., 15(3):239-243 (1997).
Wang, Y., et al., Positive and negative regulation of gene expression in eukaryotic cells with an inducible transcriptional regulator, Gene Ther., 4(5):432-441 (1997).
Wen, H. et al., Characterization of human sclera barrier properties for transscleral delivery of bevacizumab and ranibizumab, *J Pharm Sci.*, 102(3):892-903 (2013).
Wenzel, G. et al., Helper-dependent adenovirus-mediated gene transfer into the adult mouse cochlea, *Otol Neurotol.*, 28(8):1100-1108 (2007).
Wesolowski, J. et al., Single domain antibodies: promising experimental and therapeutic tools in infection and immunity, Med Microbiol Immunol., 198(3):157-174 (2009).
Wolf, A. et al., Risk of radiation-associated intracranial malignancy after stereotactic radiosurgery: a retrospective, multicentre, cohort study, *Lancet Oncol.*, 20(1):159-164 (2019).
Wong, H. et al., Anti-vascular endothelial growth factor therapies as a novel therapeutic approach to treating neurofibromatosis-related tumors, *Cancer Res.*, 70(9):3483-3493 (2010).
Woychik, R. et al., Requirement for the 3' flanking region of the bovine growth hormone gene for accurate polyadenylylation, Proc Natl Acad Sci USA, 81(13):3944-3948 (1984).
Wright, C. et al., Ototoxicity of neomycin and polymyxin B following middle ear application in the chinchilla and baboon, *Am J Otol.*, 8(6):495-499 (1987).
Written Opinion for PCT/US2018/066512 (AAV-Mediated Delivery of Therapeutic Antibodies To the Inner Ear, filed Dec. 19, 2018), received from ISA/KR, 19 pages (Apr. 17, 2019).
Written Opinion for PCT/US2021/061205, 10 pages (Mar. 31, 2022).
Written Opinion for PCT/US2023/012083, filed Feb. 1, 2023, 9 pages, (mailed Jul. 18, 2023).
Wu, H. et al. Humanization of a Murine Monoclonal Antibody by Simultaneous Optimization of Framework and CDR Residues, J. Mol. Biol., 294:151-162 (1999).
Wu, H. et al., Humanization of a murine monoclonal antibody by simultaneous optimization of framework and CDR residues, J. Mol. Biol., 294(1):151-162 (1999).
Xenaki, K. et al., Antibody or antibody fragments: implications for molecular imaging and targeted therapy of solid tumors, *Front Immunol.*, 8:1287 (2017).
Xiao, W. et al., Gene therapy vectors based on adeno-associated virus type 1, J. Virol., 73(5):3994-4003 (1999).
Yang, J. et al., Comparison of binding characteristics and in vitro activities of three inhibitors of vascular endothelial growth factor A, *Mol Pharm.*, 11(10):3421-3430 (2014).
Yoshimoto, Yuhei, Systematic review of the natural history of vestibular schwannoma, *J Neurosurg.*, 103(1):59-63 (2005).
Yoshimura, H. et al., Enhanced viral-mediated cochlear gene delivery in adult mice by combining canal fenestration with round window membrane inoculation, *Sci Rep.*, 8(1):2980, pp. 1-10 (2018).
Yuan, F. et al., Time-dependent vascular regression and permeability changes in established human tumor xenografts induced by an anti-vascular endothelial growth factor/vascular permeability factor antibody, *Proc Natl Acad Sci USA*, 93(25):14765-14770 (1996).
Zhang, H. et al., Adenovirus-adeno-associated virus hybrid for large-scale recombinant adeno-associated virus production, Human Gene Therapy, 20(9):922-929 (2009).
Zhang, L. et al., Alteration in the IL-2 signal peptide affects secretion of proteins in vitro and in vivo, J. Gene Med., 7(3):354-365 (2005).
Zhao, Y. et al., Targeting the cMET pathway augments radiation response without adverse effect on hearing in NF2 schwannoma models, *Proc Natl Acad Sci USA*, 115(9):E2077-E2084 (2018).
Zheng, J. et al., Prestin is the motor protein of cochlear outer hair cells, Nature, 405(6783):149-155 (2000).
Zinn, E. et al., In silico reconstruction of the viral evolutionary lineage yields a potent gene therapy vector, *Cell Rep.*, 12(6):1056-1068 (2015).
GenBank: AOZ48529.1, Bevacizumab light chain [synthetic construct], 3 pages, (2016).
Kang, T.H. and Jung, S.T., Boosting therapeutic potency of antibodies by taming Fc domain functions, Exp. Mol. Med., 51(11):1-9 (2019).
Mautner, V.F. et al., Bevacizumab induces regression of vestibular schwannomas in patients with neurofibromatosis type 2, Neuro. Oncol., 12(1):14-18 (2010).
Sacheli, R. et al., Gene transfer in inner ear cells: a challenging race, Gene Ther., 20(3):237-247 (2013).
Hoyng, S.A. et al., Gene delivery to rat and human Schwann cells and nerve segments: a comparison of AAV 1-9 and lentiviral vectors, Gene Ther., 22(10):767-780 (2015).
Stone, I.M. et al., Adeno-associated virus-mediated gene transfer to hair cells and support cells of the murine cochlea, Mol. Ther., 11(6):843-848 (2005).

\* cited by examiner

Avastin / Bevacizumab

Lucentis / Ranibizumab

Ranibizumab.T2A.tGFP

Eylea / Aflibercept

| Loading Sample ID | KD (M) | KD Error | ka (1/Ms) | ka Error | kdis (1/s) | kdis Error |
|---|---|---|---|---|---|---|
| anti-hVEGF MmAb | <1.0E-12 | <1.0E-12 | 2.32E+05 | 7.60E+02 | <1.0E-07 | 1.34E-07 |
| anti-hVEGF MmAb in CM | <1.0E-12 | <1.0E-12 | 2.86E+05 | 8.54E+02 | <1.0E-07 | 1.27E-07 |
| Bevacizumab | <1.0E-12 | 1.32E-12 | 1.62E+05 | 1.43E+03 | <1.0E-07 | 2.14E-07 |
| Parental | N/A | N/A | N/A | N/A | N/A | N/A |

Figure 4C

SEQUENCE LISTING

```
Sequence total quantity: 61
SEQ ID NO: 1                moltype = AA   length = 412
FEATURE                     Location/Qualifiers
source                      1..412
                            mol_type = protein
                            organism = Homo sapiens
                            note = Human
SEQUENCE: 1
MTDRQTDTAP SPSYHLLPGR RRTVDAAASR GQGPEPAPGG GVEGVGARGV ALKLFVQLLG    60
CSRFGGAVVR AGEAEPSGAA RSASSGREEP QPEEGEEEEE KEEERGPQWR LGARKPGSWT   120
GEAAVCADSA PAARAPQALA RASGRGGRVA RRGAEESGPP HSPSRRGSAS RAGPGRASET   180
MNFLLSWVHW SLALLLYLHH AKWSQAAPMA EGGGQNHHEV VKFMDVYQRS YCHPIETLVD   240
IFQEYPDEIE YIFKPSCVPL MRCGGCCNDE GLECVPTEES NITMQIMRIK PHQGQHIGEM   300
SFLQHNKCEC RPKKDRARQE KKSVRGKGKG QKRKRKKSRY KSWSVYVGAR CCLMPWSLPG   360
PHPCGPCSER RKHLFVQDPQ TCKCSCKNTD SRCKARQLEL NERTCRCDKP RR           412

SEQ ID NO: 2                moltype = DNA   length = 1239
FEATURE                     Location/Qualifiers
source                      1..1239
                            mol_type = unassigned DNA
                            organism = Homo sapiens
                            note = Human
SEQUENCE: 2
ctgacggaca gacagacaga caccgccccc agcccagct accacctcct ccccggccgg     60
cggcggacag tggacgcggc ggcgagccgc gggcaggggc cggagcccgc gcccggaggc   120
ggggtggagg gggtcggggc tcgcggcgtc gcactgaaac ttttcgtcca acttctgggc   180
tgttctcgct tcggaggagc cgtggtccgc gcggggggaag ccgagccgag cggagccgcg   240
agaagtgcta gctcgggccg ggaggagccg cagccggagg aggaagaag                300
aaggaagagg agaggggggcc gcagtggcga ctcggcgctc ggaagccggg ctcatgacg    360
ggtgaggcgg cggtgtgcgc agacagtgct ccagccgcgc gcgctcccca ggccctggcc   420
cgggcctcgg gccggggagg aagagtagct cgccgaggcg ccgaggagag cgggccgccc   480
cacagcccga gccggagagg gagcgcgagc cgcgccggcc ccgtcgggc ctccgaaacc    540
atgaactttc tgctgtcttg ggtgcattgg agccttgcct tgctgctcta cctccaccat   600
gccaagtggt cccaggctgc acccatggca gaaggaggag ggcagaatca tcacgaagtg   660
gtgaagttca tggatgtcta tcagcgcagc tactgccatc caatcgagac cctggtggac   720
atcttccagg agtaccctga tgagatcgag tacatcttca agccatcctg tgtgcccctg   780
atgcgatgcg gggctgctg caatgacgag ggcctggagt gtgtgcccac tgaggagtcc   840
aacatcacca tgcagattat gcggatcaaa cctcaccaag gccagcacat aggagagatg   900
agcttcctac agcacaacaa atgtgaatgc agaccaaaga aagatagagc aagacaagaa   960
aaaaaatcag ttcgaggaaa gggaaagggg caaaaacgaa agcgcaagaa atcccggtat  1020
aagtcctgga gcgtgtacgt tggtgcccgc tgctgtctaa tgccctggag cctccctggc  1080
ccccatccct gtgggccttg ctcagagcgg agaaagcatt tgtttgtaca agatccgcag  1140
acgtgtaaat gttcctgcaa aaacacagac tcgcgttgca aggcgaggca gcttgagtta  1200
aacgaacgta cttgcagatg tgacaagccg aggcggtga                         1239

SEQ ID NO: 3                moltype = AA   length = 389
FEATURE                     Location/Qualifiers
source                      1..389
                            mol_type = protein
                            organism = Homo sapiens
                            note = Human
SEQUENCE: 3
MTDRQTDTAP SPSYHLLPGR RRTVDAAASR GQGPEPAPGG GVEGVGARGV ALKLFVQLLG    60
CSRFGGAVVR AGEAEPSGAA RSASSGREEP QPEEGEEEEE KEEERGPQWR LGARKPGSWT   120
GEAAVCADSA PAARAPQALA RASGRGGRVA RRGAEESGPP HSPSRRGSAS RAGPGRASET   180
MNFLLSWVHW SLALLLYLHH AKWSQAAPMA EGGGQNHHEV VKFMDVYQRS YCHPIETLVD   240
IFQEYPDEIE YIFKPSCVPL MRCGGCCNDE GLECVPTEES NITMQIMRIK PHQGQHIGEM   300
SFLQHNKCEC RPKKDRARQE KKSVRGKGKG QKRKRKKSRP CGPCSERRKH LFVQDPQTCK   360
CSCKNTDSRC KARQLELNER TCRCDKPRR                                     389

SEQ ID NO: 4                moltype = DNA   length = 1170
FEATURE                     Location/Qualifiers
source                      1..1170
                            mol_type = unassigned DNA
                            organism = Homo sapiens
                            note = Human
SEQUENCE: 4
ctgacggaca gacagacaga caccgccccc agcccagct accacctcct ccccggccgg     60
cggcggacag tggacgcggc ggcgagccgc gggcaggggc cggagcccgc gcccggaggc   120
ggggtggagg gggtcggggc tcgcggcgtc gcactgaaac ttttcgtcca acttctgggc   180
tgttctcgct tcggaggagc cgtggtccgc gcggggggaag ccgagccgag cggagccgcg   240
agaagtgcta gctcgggccg ggaggagccg cagccggagg aggggaggga ggaagaagag   300
aaggaagagg agaggggggcc gcagtggcga ctcggcgctc ggaagccggg ctcatgacg    360
ggtgaggcgg cggtgtgcgc agacagtgct ccagccgcgc gcgctcccca ggccctggcc   420
cgggcctcgg gccggggagg aagagtagct cgccgaggcg ccgaggagag cgggccgccc   480
cacagcccga gccggagagg gagcgcgagc cgcgccggcc ccgtcgggc ctccgaaacc    540
atgaactttc tgctgtcttg ggtgcattgg agccttgcct tgctgctcta cctccaccat   600
gccaagtggt cccaggctgc acccatggca gaaggaggag ggcagaatca tcacgaagtg   660
```

-continued

```
gtgaagttca tggatgtcta tcagcgcagc tactgccatc caatcgagac cctggtggac    720
atcttccagg agtaccctga tgagatcgag tacatcttca agccatcctg tgtgcccctg    780
atgcgatgcg ggggctgctg caatgacgag ggcctggagt gtgtgcccac tgaggagtcc    840
aacatcacca tgcagattat gcggatcaaa cctcaccaag gccagcacat aggagagatg    900
agcttcctac agcacaacaa atgtgaatgc agaccaaaga aagatagagc aagacaagaa    960
aaaaaatcag ttcgaggaaa gggaaagggg caaaaacgaa agcgcaagaa atcccgtccc   1020
tgtgggcctt gctcagagcg gagaaagcat ttgtttgtac aagatccgca gacgtgtaaa   1080
tgttcctgca aaaacacaga ctcgcgttgc aaggcgaggc agcttgagtt aaacgaacgt   1140
acttgcagat gtgacaagcc gaggcggtga                                    1170

SEQ ID NO: 5              moltype = AA  length = 214
FEATURE                   Location/Qualifiers
REGION                    1..214
                          note = Bevacizumab light chain variable domain
source                    1..214
                          mol_type = protein
                          organism = synthetic construct
SEQUENCE: 5
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 6              moltype = AA  length = 453
FEATURE                   Location/Qualifiers
REGION                    1..453
                          note = Bevacizumab heavy chain variable domain
source                    1..453
                          mol_type = protein
                          organism = synthetic construct
SEQUENCE: 6
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 7              moltype = AA  length = 214
FEATURE                   Location/Qualifiers
REGION                    1..214
                          note = Ranibizumab light chain variable domain
source                    1..214
                          mol_type = protein
                          organism = synthetic construct
SEQUENCE: 7
DIQLTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 8              moltype = AA  length = 231
FEATURE                   Location/Qualifiers
REGION                    1..231
                          note = Ranibizumab heavy chain variable domain
source                    1..231
                          mol_type = protein
                          organism = synthetic construct
SEQUENCE: 8
EVQLVESGGG LVQPGGSLRL SCAASGYDFT HYGMNWVRQA PGKGLEWVGW INTYTGEPTY    60
AADFKRRFTF SLDTSKSTAY LQMNSLRAED TAVYYCAKYP YYYGTSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH L            231

SEQ ID NO: 9              moltype = AA  length = 22
FEATURE                   Location/Qualifiers
REGION                    1..22
                          note = Signal peptide
source                    1..22
                          mol_type = protein
                          organism = synthetic construct
SEQUENCE: 9
MEFFKKTALA ALVMGFSGAA LA                                             22

SEQ ID NO: 10             moltype = AA  length = 22
FEATURE                   Location/Qualifiers
REGION                    1..22
```

```
                      note         = Signal peptide
source                1..22
                      mol_type     = protein
                      organism     = synthetic construct
SEQUENCE: 10
MKYLLPTAAA GLLLLAAQPA MA                                               22

SEQ ID NO: 11         moltype = DNA   length = 17
FEATURE               Location/Qualifiers
source                1..17
                      mol_type     = unassigned DNA
                      organism     = Homo sapiens
                      note         = Human
SEQUENCE: 11
aaataaaata cgaaatg                                                     17

SEQ ID NO: 12         moltype = AA    length = 431
FEATURE               Location/Qualifiers
REGION                1..431
                      note         = Aflibercept
source                1..431
                      mol_type     = protein
                      organism     = synthetic construct
SEQUENCE: 12
SDTGRPFVEM YSEIPEIIHM TEGRELVIPC RVTSPNITVT LKKFPLDTLI PDGKRIIWDS       60
RKGFIISNAT YKEIGLLTCE ATVNGHLYKT NYLTHRQTNT IIDVVLSPSH GIELSVGEKL      120
VLNCTARTEL NVGIDFNWEY PSSKHQHKKL VNRDLKTQSG SEMKKFLSTL TIDGVTRSDQ      180
GLYTCAASSG LMTKKNSTFV RVHEKDKTHT CPPCPAPELL GGPSVFLFPP KPKDTLMISR      240
TPEVTCVVVD VSHEDPEVKF NWYVDGVEVH NAKTKPREEQ YNSTYRVVSV LTVLHQDWLN      300
GKEYKCKVSN KALPAPIEKT ISKAKGQPRE PQVYTLPPSR DELTKNQVSL TCLVKGFYPS      360
DIAVEWESNG QPENNYKTTP PVLDSDGSFF LYSKLTVDKS RWQQGNVFSC SVMHEALHNH      420
YTQKSLSLSP G                                                          431

SEQ ID NO: 13         moltype = AA    length = 206
FEATURE               Location/Qualifiers
source                1..206
                      mol_type     = protein
                      organism     = Homo sapiens
                      note         = Human
SEQUENCE: 13
APMAEGGGQN HHEVVKFMDV YQRSYCHPIE TLVDIFQEYP DEIEYIFKPS CVPLMRCGGC       60
CNDEGLECVP TEESNITMQI MRIKPHQGQH IGEMSFLQHN KCECRPKKDR ARQEKKSVRG      120
KGKGQKRKRK KSRYKSWSVY VGARCCLMPW SLPGPHPCGP CSERRKHLFV QDPQTCKCSC      180
KNTDSRCKAR QLELNERTCR CDKPRR                                          206

SEQ ID NO: 14         moltype = AA    length = 186
FEATURE               Location/Qualifiers
source                1..186
                      mol_type     = protein
                      organism     = Homo sapiens
                      note         = Human
SEQUENCE: 14
PVSQPDAPGH QRKVVSWIDV YTRATCQPRE VVVPLTVELM GTVAKQLVPS CVTVQRCGGC       60
CPDDGLECVP TGQHQVRMQI LMIRYPSSQL GEMSLEEHSQ CECRPKKKDS AVKPDRAATP      120
HHRPQPRSVP GWDSAPGAPS PADITHPTPA PGPSAHAAPS TTSALTPGPA AAADAAASS       180
VAKGGA                                                                186

SEQ ID NO: 15         moltype = AA    length = 116
FEATURE               Location/Qualifiers
source                1..116
                      mol_type     = protein
                      organism     = Homo sapiens
                      note         = Human
SEQUENCE: 15
AHYNTEILKS IDNEWRKTQC MPREVCIDVG KEFGVATNTF FKPPCVSVYR CGGCCNSEGL       60
QCMNTSTSYL SKTLFEITVP LSQGPKPVTI SFANHTSCRC MSKLDVYRQV HSIIRR         116

SEQ ID NO: 16         moltype = AA    length = 117
FEATURE               Location/Qualifiers
source                1..117
                      mol_type     = protein
                      organism     = Homo sapiens
                      note         = Human
SEQUENCE: 16
FAATFYDIET LKVIDEEWQR TQCSPRETCV EVASELGKST NTFFKPPCVN VFRCGGCCNE       60
ESLICMNTST SYISKQLFEI SVPLTSVPEL VPVKVANHTG CKCLPTAPRH PYSIIRR        117

SEQ ID NO: 17         moltype = AA    length = 687
FEATURE               Location/Qualifiers
```

```
source                  1..687
                        mol_type = protein
                        organism = Homo sapiens
                        note = Human
SEQUENCE: 17
MVSYWDTGVL LCALLSCLLL TGSSSGSKLK DPELSLKGTQ HIMQAGQTLH LQCRGEAAHK   60
WSLPEMVSKE SERLSITKSA CGRNGKQFCS TLTLNTAQAN HTGFYSCKYL AVPTSKKKET  120
ESAIYIFISD TGRPFVEMYS EIPEIIHMTE GRELVIPCRV TSPNITVTLK KFPLDTLIPD  180
GKRIIWDSRK GFIISNATYK EIGLLTCEAT VNGHLYKTNY LTHRQTNTII DVQISTPRPV  240
KLLRGHTLVL NCTATTPLNT RVQMTWSYPD EKNKRASVRR RIDQSNSHAN IFYSVLTIDK  300
MQNKDKGLYT CRVRSGPSFK SVNTSVHIYD KAFITVKHRK QQVLETVAGK RSYRLSMKVK  360
APPSPEVVWL KDGLPATEKS ARYLTRGYSL IIKDVTEEDA GNYTILLSIK QSNVFKNLTA  420
TLIVNVKPQI YEKAVSSFPD PALYPLGSRQ ILTCTAYGIP QPTIKWFWHP CNHNHSEARC  480
DFCSNNEESF ILDADSNMGN RIESITQRMA IIEGKNKMAS TLVVADSRIS GIYICIASNK  540
VGTVGRNISF YITDVPNGFH VNLEKMPTEG EDLKLSCTVN KFLYRDVTWI LLRTVNNRTM  600
HYSISKQKMA ITKEHSITLN LTIMNVSLQD SGTYACRARN VYTGEEILQK KEITIRGEHC  660
NKKAVFSRIS KFKSTRNDCT TQSNVKH                                      687

SEQ ID NO: 18           moltype = DNA  length = 2064
FEATURE                 Location/Qualifiers
source                  1..2064
                        mol_type = unassigned DNA
                        organism = Homo sapiens
                        note = Human
SEQUENCE: 18
atggtcagct actgggacac cggggtcctg ctgtgcgcgc tgctcagctg tctgcttctc   60
acaggatcta gttcaggttc aaaattaaaa gatcctgaac tgagtttaaa aggcacccag  120
cacatcatgc aagcaggcca gacactgcat ctccaatgca gggggaagc agcccataaa  180
tggtctcttgc ctgaaatggt gagtaaggaa agcgaaaggc tgagcataac taatctgcc  240
tgtcgaagaa atggcaaaca attctgcagt acttaacct tgaacacagc tcaagcaaac  300
cacactggct tctacagctg caaatatcta gctgtaccta cttcaaagaa gaaggaaaca  360
gaatctgcaa tctatatatt tattagtgat acaggtagac ctttcgtaga gatgtacagt  420
gaaatccccg aaattataca catgactgaa ggaagggagc tcgtcattcc ctgccgggtt  480
acgtcaccta acatcactgt tactttaaaa agtttccac ttgacacttt gatccctgat  540
ggaaaacgca taatctggga cagtagaaag ggcttcatca tatcaaatgc aacgtacaaa  600
gaaatagggc ttctgacctg tgaagcaaca gtcaatgggc atttgtataa gacaaactat  660
ctcacacatc gacaaaccaa tacaatcata gatgtccaaa taagcacacc acgcccagtc  720
aaattactta gaggccatac tcttgtcctc aattgtactg ctaccactcc cttgaacacg  780
agagttcaaa tgacctggag ttaccctgat gaaaaaaata gagagcttc cgtaaggcga  840
cgaattgacc aaagcaattc ccatgccaac atattctaca gtgttcttac tattgacaaa  900
atgcagaaca aagacaaagg actttatact tgtcgtgtaa ggagtggacc atcattcaaa  960
tctgttaaca cctcagtgca tatatatgat aaagcattca tcactgtgaa acatcgaaaa 1020
cagcaggtgc ttgaaaccgt agctggcaag cggtcttcac ctgctctctat gaaagtgaag 1080
gcatttccct cgccggaagt tgtatggtta aaagatgggt tacctgcgac tgagaaatct 1140
gctcgctatt tgactcgtgg ctactcgtta attatcaagg acgtaactga gaggatgca 1200
gggaattata caatcttgct gagcataaaa cagtcaaatg tgtttaaaaa cctcactgcc 1260
actctaattg tcaatgtgaa accccagatt tacgaaaagg ccgtgtcatc gtttccagac 1320
ccggctctct acccactggg cagcagacaa atcctgactt gtaccgcata tggtatccca 1380
caacctacaa tcaagtggtt ctggcacccc tgtaaccata atcattccga agcaaggtgt 1440
gacttttgtt ccaataatga agagtccttt atcctggatg ctgacagcaa catgggaaac 1500
agaattgaga gcatcactca gcgcatggca ataatagaag gaaagaataa gatggctagc 1560
accttggttg tggctgactc tagaatttct ggaatctaca tttgcatagc ttccaataaa 1620
gttgggactg tgggaagaaa cataagcttt tatatcacag atgtgccaaa tgggtttcat 1680
gttaacttgg aaaaaatgcc gacggaagga gaggacctga actgtcttg cacagttaac 1740
aagttcttat acagagacgt tacttggatt ttactgcgga cagttaataa cagaacaatg 1800
cactacagta ttagcaagca aaaaatggcc atcactaagg agcactccat cactcttaat 1860
cttaccatca tgaatgtttc cctgcaagat tcaggcacct atgcctgcag agccaggaat 1920
gtatacacag gggaagaaat cctccagaag aaagaaatta caatcagagg tgagcactgc 1980
aacaaaaagg ctgtttttctc tcggatcctcc aaatttaaaa gcacaaggaa tgattgtacc 2040
acacaaagta atgtaaaaca ttaa                                        2064

SEQ ID NO: 19           moltype = AA  length = 733
FEATURE                 Location/Qualifiers
source                  1..733
                        mol_type = protein
                        organism = Homo sapiens
                        note = Human
SEQUENCE: 19
MVSYWDTGVL LCALLSCLLL TGSSSGSKLK DPELSLKGTQ HIMQAGQTLH LQCRGEAAHK   60
WSLPEMVSKE SERLSITKSA CGRNGKQFCS TLTLNTAQAN HTGFYSCKYL AVPTSKKKET  120
ESAIYIFISD TGRPFVEMYS EIPEIIHMTE GRELVIPCRV TSPNITVTLK KFPLDTLIPD  180
GKRIIWDSRK GFIISNATYK EIGLLTCEAT VNGHLYKTNY LTHRQTNTII DVQISTPRPV  240
KLLRGHTLVL NCTATTPLNT RVQMTWSYPD EKNKRASVRR RIDQSNSHAN IFYSVLTIDK  300
MQNKDKGLYT CRVRSGPSFK SVNTSVHIYD KAFITVKHRK QQVLETVAGK RSYRLSMKVK  360
APPSPEVVWL KDGLPATEKS ARYLTRGYSL IIKDVTEEDA GNYTILLSIK QSNVFKNLTA  420
TLIVNVKPQI YEKAVSSFPD PALYPLGSRQ ILTCTAYGIP QPTIKWFWHP CNHNHSEARC  480
DFCSNNEESF ILDADSNMGN RIESITQRMA IIEGKNKMAS TLVVADSRIS GIYICIASNK  540
VGTVGRNISF YITDVPNGFH VNLEKMPTEG EDLKLSCTVN KFLYRDVTWI LLRTVNNRTM  600
HYSISKQKMA ITKEHSITLN LTIMNVSLQD SGTYACRARN VYTGEEILQK KEITIRDQEA  660
```

```
PYLLRNLSDH TVAISSSTTL DCHANGVPEP QITWFKNNHK IQQEPELYTS TSPSSSSSSP    720
LSSSSSSSSS SSS                                                      733

SEQ ID NO: 20           moltype = DNA  length = 2202
FEATURE                 Location/Qualifiers
source                  1..2202
                        mol_type = unassigned DNA
                        organism = Homo sapiens
                        note = Human
SEQUENCE: 20
atggtcagct actgggacac cggggtcctg ctgtgcgcgc tgctcagctg tctgcttctc    60
acaggatcta gttcaggttc aaaattaaaa gatcctgaac tgagtttaaa aggcacccag   120
cacatcatgc aagcaggcca gacactgcat ctccaatgca ggggggaagc agcccataaa   180
tggtctttgc ctgaaatggt gagtaaggaa agcgaaaggc tgagcataac taaatctgcc   240
tgtggaagaa atggcaaaca attctgcagt actttaacct gaacacagc tcaagcaaac    300
cacactggct tctacagctg caaatatcta gctgtaccta cttcaaagaa gaaggaaaca   360
gaatctgcaa tctatatatt tattagtgat acaggtagac ttcgtaga gatgtacagt    420
gaaatccccg aaattataca catgactgaa ggaagggagc tcgtcattcc ctgccgggtt   480
acgtcaccta acatcactgt tactttaaaa agtttccac ttgacacttt gatccctgat    540
ggaaaacgca taatctggga cagtagaaag ggcttcatca tatcaaatgc aacgtacaaa   600
gaaatagggc ttctgacctg tgaagcaaca gtcaatgggc atttgtataa acaaactat    660
ctcacacatc gacaaaccaa tacaatcata gatgtccaaa taagcacacc acgcccagtc   720
aaattactta gaggccatac tcttgtcctc aattgtactg ctaccactcc cttgaacacg   780
agagttcaaa tgacctggag ttaccctgat gaaaaaaata gagagcttc cgtaaggcga    840
cgaattgacc aaagcaattc ccatgccaac atattctaca gtgttcttac tattgacaaa   900
atgcagaaca aagacaaagg acttatact tgtcgtgtaa gagagtggac atcattcaaa    960
tctgttaaca cctcagtgca tatatatgat aaagcattca tcactgtgaa acatcgaaaa  1020
cagcaggtgc ttgaaaccgt agctggcaag cggtcttacc ggctctctat gaaagtgaag  1080
gcatttccct cgccggaagt tgtatggtta aaagatgggt tacctgcgac tgagaaatct  1140
gctcgctatt tgactcgtgg ctactcgtta attatcaagg acgtaactga agaggatgca  1200
gggaattata caatcttgct gagcataaaa cagtcaaatg tgtttaaaaa cctcactgcc  1260
actctaattg tcaatgtgaa accccagatt tacgaaaagg ccgtgtcatc gtttccagac  1320
ccggctctct acccactggg cagcagacaa atcctgactt gtaccgcata tggtatccct  1380
caacctacaa tcaagtggtt ctggcacccc tgtaaccata atcattccga agcaaggtgt  1440
gacttttgtt ccaataatga agagtccttt atcctggatg ctgacagcaa catgggaaac  1500
agaattgaga gcatcactca gcgcatggca ataatagaag gaagaataa gatggctagc  1560
accttggttt ggctgactc tagaattct ggaatctaca tttgcatagc ttccaataaa   1620
gttgggactg tgggaagaaa cataagcttt tatatcacag atgtgccaaa tgggtttcat  1680
gttaacttgg aaaaaatgcc gacggaagga gaggacctga aactgtcttg cacagttaac  1740
aagttcttat acagagacgt tacttggatt ttactgcgga cagttaataa cagaacaatg  1800
cactacagta ttagcaagca aaaaatggcc atcactaagg agcactccat cactcttaat  1860
cttaccatca tgaatgtttc cctgcaagat tcaggcacct atgcctgcag agccaggaat  1920
gtatacacag gggaagaaat cctccagaag aaagaaatta caatcagaga tcaggaagac  1980
ccatacctcc tgcgaaacct cagtgatcac acagtggcca tcagcagttc caccacttta  2040
gactgtcatg ctaatggtgt ccccgagcct cagatcactt ggtttaaaaa caaccacaaa  2100
atacaacaag agcctgaact gtatacatca acgtcaccat cgtcatcgtc atcatccaca  2160
ttgtcatcat catcatcatc gtcatcatca tcatcatcat ag                     2202

SEQ ID NO: 21           moltype = AA  length = 541
FEATURE                 Location/Qualifiers
source                  1..541
                        mol_type = protein
                        organism = Homo sapiens
                        note = Human
SEQUENCE: 21
MVSYWDTGVL LCALLSCLLL TGSSSGSKLK DPELSLKGTQ HIMQAGQTLH LQCRGEAAHK    60
WSLPEMVSKE SERLSITKSA CGRNGKQFCS TLTLNTAQAN HTGFYSCKYL AVPTSKKKET   120
ESAIYIFISD TGRPFVEMYS EIPEIIHMTE GRELVIPCRV TSPNITVTLK KFPLDTLIPD   180
GKRIIWDSRK GFIISNATYK EIGLLTCEAT VNGHLYKTNY LTHRQTNTII DVQISTPRPV   240
KLLRGHTLVL NCTATTPLNT RVQMTWSYPD EKNKRASVRR RIDQSNSHAN IFYSVLTIDK   300
MQNKDKGLYT CRVRSGPSFK SVNTSVHIYD KAFITVKHRK QQVLETVAGK RSYRLSMKVK   360
AFPSPEVVWL KDGLPATEKS ARYLTRGYSL IIKDVTEEDA GNYTILLSIK QSNVFKNLTA   420
TLIVNVKPQI YEKAVSSFPD PALYPLGSRQ ILTCTAYGIP QPTIKWFWHP CNHNHSEARC   480
DFCSNNEESF ILDADSNMGN RIESITQRMA IIEGKNKLPP ANSSFMLPPT SFSSNYFHFL   540
P                                                                   541

SEQ ID NO: 22           moltype = DNA  length = 1626
FEATURE                 Location/Qualifiers
source                  1..1626
                        mol_type = unassigned DNA
                        organism = Homo sapiens
                        note = Human
SEQUENCE: 22
atggtcagct actgggacac cggggtcctg ctgtgcgcgc tgctcagctg tctgcttctc    60
acaggatcta gttcaggttc aaaattaaaa gatcctgaac tgagtttaaa aggcacccag   120
cacatcatgc aagcaggcca gacactgcat ctccaatgca ggggggaagc agcccataaa   180
tggtctttgc ctgaaatggt gagtaaggaa agcgaaaggc tgagcataac taaatctgcc   240
tgtggaagaa atggcaaaca attctgcagt actttaacct gaacacagc tcaagcaaac    300
cacactggct tctacagctg caaatatcta gctgtaccta cttcaaagaa gaaggaaaca   360
```

```
                                                            -continued gaatctgcaa tctatatatt tattagtgat acaggtagac ctttcgtaga gatgtacagt    420
gaaatccccg aaattataca catgactgaa ggaagggagc tcgtcattcc ctgccgggtt    480
acgtcaccta acatcactgt tactttaaaa aagtttccac ttgacacttt gatccctgat    540
ggaaaacgca taatctggga cagtagaaag ggcttcatca tatcaaatgc aacgtacaaa    600
gaaataggc  ttctgacctg tgaagcaaca gtcaatggca atttgtataa gacaaactat    660
ctcacacatc gacaaaccaa tacaatcata gatgtccaaa taagcacacc acgcccagtc    720
aaattactta gaggccatac tcttgtcctc aattgtactg ctaccactcc cttgaacacg    780
agagttcaaa tgacctggag ttaccctgat gaaaaaata agagagcttc cgtaaggcga    840
cgaattgacc aaagcaattc ccatgccaac atattctaca gtgttcttac tattgacaag    900
atgcagaaca aagacaaagg acttatact tgtcgtgtaa ggagtggacc atcattcaa     960
tctgttaaca cctcagtgca tatatatgat aaagcattca tcactgtgaa acatcgaaaa   1020
cagcaggtgc ttgaaaccgt agctggcaag cggtcttacc ggctctctat gaaagtgaag   1080
gcatttccct cgcggaagt tgtatggtta aagatgggt tacctgcgac tgagaaatct    1140
gctcgctatt tgactctgg ctactcgtta attatcaagg acgtaactga agaggatgca   1200
gggaattata caatcttgct gagcataaaa cagtcaaatg tgtttaaaaa cctcactgcc   1260
actctaattg tcaatgtgaa accccagatt tacgaaaagg ccgtgtcatc gtttccagac   1320
ccggctctct acccactggg cagcagacaa atcctgactt gtaccgcata tggtatccct   1380
caacctacaa tcaagtggtt ctggcaccc tgtaaccata atcattccga agcaaggtgt   1440
gactttgtt ccaataatga agagtccttt atcctggatg ctgacagcaa catgggaaac   1500
agaattgaga gcatcactca gcgcatggca ataatagaag gaaagaataa gcttccacca   1560
gctaacagtt ctttcatgtt gccacctaca agcttctctt ccaactactt ccatttcctt   1620
ccgtga                                                              1626

SEQ ID NO: 23          moltype = AA   length = 732
FEATURE                Location/Qualifiers
source                 1..732
                       mol_type = protein
                       organism = Homo sapiens
                       note = Human
SEQUENCE: 23
SKLKDPELSL KGTQHIMQAG QTLHLQCRGE AAHKWSLPEM VSKESERLSI TKSACGRNGK     60
QFCSTLTLNT AQANHTGFYS CKYLAVPTSK KKETESAIYI FISDTGRPFV EMYSEIPEII   120
HMTEGRELVI PCRVTSPNIT VTLKKFPLDT LIPDGKRIIW DSRKGFIISN ATYKEIGLLT   180
CEATVNGHLY KTNYLTHRQT NTIIDVQIST PRPVKLLRGH TLVLNCTATT PLNTRVQMTW   240
SYPDEKNKRA SVRRRIDQSN SHANIFYSVL TIDKMQNKDK GLYTCRVRSG PSFKSVNTSV   300
HIYDKAFITV KHRKQQVLET VAGKRSYRLS MKVKAFPSPE VVWLKDGLPA TEKSARYLTR   360
GYSLIIKDVT EEDAGNYTIL LSIKQSNVFK NLTATLIVNV KPQIYEKAVS SFPDPALYPL   420
GSRQILTCTA YGIPQPTIKW FWHPCNHNHS EARCDFCSNN EESFILDADS NMGNRIESIT   480
QRMAIIEGKN KMASTLVVAD SRISGIYICI ASNKVGTVGR NISFYITDVP NGFHVNLEKM   540
PTEGEDLKLS CTVNKFLYRD VTWILLRTVN NRTMHYSISK QKMAITKEHS ITLNLTIMNV   600
SLQDSGTYAC RARNVYTGEE ILQKKEITIR DQEAPYLLRN LSDHTVAISS STTLDCHANG   660
VPEPQITWFK NNHKIQQEPG IILGPGSSTL FIERVTEEDE GVYHCKATNQ KGSVESSAYL   720
TVQGTSDKSN LE                                                      732

SEQ ID NO: 24          moltype = AA   length = 737
FEATURE                Location/Qualifiers
source                 1..737
                       mol_type = protein
                       organism = Mus sp.
                       note = Mouse
SEQUENCE: 24
YGSGSKLKVP ELSLKGTQHV MQAGQTLFLK CRGEAAHSWS LPTTVSQEDK RLSITPPSAC     60
GRDNRQFCST LTLDTAQANH TGLYTCRYLP TSTSKKKKAE SSIYIFVSDA GSPFIEMHTD   120
IPKLVHMTEG RQLIIPCRVT SPNVTVTLKK FPFDTLTPDG QRITWDSRRG FIIANATYKE   180
IGLLNCEATV NGHLYQTNYL THRQTNTILD VQIRPPSPVR LHGQTLVLN CTATTELNTR   240
VQMSWNYPGK ATKRASIRQR IDRSHSNNV FHSVLKINNV ESRDKGLYTC RVKSGSSFQS    300
FNTSVHYEK GFISVKHRKQ PVQETTAGRR SYRLSMKVKA FPSPEIVWLK DGSPATLKSA    360
RYLVHGYSLI IKDVTTEDAG DYTILLGIKQ SRLFKNLTAT LIVNVKPQIY EKSVSSLPSP   420
PLYPLGSRQV LTCTVYGIPR PTITWLWHPC HHNHSKERYD FCTENEESFI LDPSSNLGNR   480
IESISQRMTV IEGTNKTVST LVVADSQTPG IYSCRAFNKI GTVERNIKFY VTDVPNGFHV   540
SLEKMPAEGE DLKLSCVVNK FLYRDITWIL LRTVNNRTMH HSISKQKMAT TQDYSITLNL   600
VIKNVSLEDS GTYACRARNI YTGEDILRKT EVLVRDSEAP HLLQNLSDYE VSISGSTTLD   660
CQARGVPAPQ ITWFKNNHKI QQEPGIILGP GNSTLFIERV TEEDEGVYRC RATNQKGAVE   720
SAAYLTVQGT SDKSNLE                                                 737

SEQ ID NO: 25          moltype = AA   length = 736
FEATURE                Location/Qualifiers
source                 1..736
                       mol_type = protein
                       organism = Rattus sp.
                       note = Rat
SEQUENCE: 25
YCSGSKLKGP ELSLKGTQHV MQAGQTLFLK CRGEAAHSWS LPTTVSQEDK KLSVTRSACG     60
RNNRQFCSTL TLNMAQANHT GLYSCRYLPK STSKEKKMES AIYIFVSDAG SPFIEMHSDI   120
PKLVHMTEGR ELIIPCRVTS PNITVTLKKF PFDALTPDGQ RIAWDSRRGF IIANATYKEI   180
GLLTCEATVN GHLYQTSYLT HRQTNTILDV QISPPSPVRF LRGQTLVLNC TVTTDLNTRV   240
QMSWNYPGKA TKRASIRQRI DQSNPHSNVF HSVLKINNVE SRDKGLYTCR VKSGSSFRTF   300
NTSVHVYEKG FISVKHRKQQ VQETIAGKRS HRLSMKVKAF PSPEVVWLKD GVPATEKSAR   360
YSVHGYSLII KDVTAEDAGD YTILLGIKQS KLFRNLTATL IVNVKPQIYE KSVSSLPSPP   420
```

```
LYPLGSRQVL TCTVYGIPQP TIKWLWHPCH YNHSKERNDF CFGSEESFIL DSSSNIGNRI    480
EGITQRMMVI EGTNKTVSTL VVADSRTPGS YSCKAFNKIG TVERDIRFYV TDVPNGFHVS    540
LEKIPTEGED LKLSCVVSKF LYRDITWILL RTVNNRTMHH SISKQKMATT QDYSITLNLV    600
IKNVSLEDSG TYACRARNIY TGEEILRKTE VLVRDLEAPL LLQNLSDHEV SISGSTTLDC    660
QARGVPAPQI TWFKNNHKIQ QEPGIILGPG NSTLFIERVT EEDEGVYRCR ATNQKGVVES    720
SAYLTVQGTS DKSNLE                                                   736

SEQ ID NO: 26           moltype = AA  length = 745
FEATURE                 Location/Qualifiers
source                  1..745
                        mol_type = protein
                        organism = Homo sapiens
                        note = Human
SEQUENCE: 26
ASVGLPSVSL DLPRLSIQKD ILTIKANTTL QITCRGQRDL DWLWPNNQSG SEQRVEVTEC    60
SDGLFCKTLT IPKVIGNDTG AYKCFYRETD LASVIYVYVQ DYRSPFIASV SDQHGVVYIT   120
ENKNKTVVIP CLGSISNLNV SLCARYPEKR FVPDGNRISW DSKKGFTIPS YMISYAGMVF   180
CEAKINDESY QSIMYIVVVV GYRIYDVVLS PSHGIELSVG EKLVLNCTAR TELNVGIDFN   240
WEYPSSKHQH KKLVNRDLKT QSGSEMKKFL STLTIDGVTR SDQGLYTCAA SSGLMTKKNS   300
TFVRVHEKPF VAFGSGMESL VEATVGERVR IPAKYLGYPP PEIKWYKNGI PLESNHTIKA   360
GHVLTIMEVS ERDTGNYTVI LTNPISKEKQ SHVVSLVVYV PPQIGEKSLI SPVDSYQYGT   420
TQTLTCTVYA IPPPHHIHWY WQLEEECANE PSQAVSVTNP YPCEEWRSVE DFQGGNKIEV   480
NKNQFALIEG KNKTVSTLVI QAANVSALYK CEAVNKVGRG ERVISFHVTR GPEITLQPDM   540
QPTEQESVSL WCTADRSTFE NLTWYKLGPQ PLPIHVGELP TPVCKNLDTL WKLNATMFSN   600
STNDILIMEL KNASLQDQGD YVCLAQDRKT KKRHCVVRQL TVLERVAPTI TGNLENQTTS   660
IGESIEVSCT ASGNPPPQIM WFKDNETLVE DSGIVLKDGN RNLTIRRVRK EDEGLYTCQA   720
CSVLGCAKVE AFFIIEGAQE KTNLE                                         745

SEQ ID NO: 27           moltype = AA  length = 743
FEATURE                 Location/Qualifiers
source                  1..743
                        mol_type = protein
                        organism = Mus sp.
                        note = Mouse
SEQUENCE: 27
ASVGLPGDFL HPPKLSTQKD ILTILANTTL QITCRGQRDL DWLWPNAQRD SEERVLVTEC    60
GGGDSIFCKT LTIPRVVGND TGAYKCSYRD VDIASTVYVY VRDYRSPFIA SVSDQHGIVY   120
ITENKNKTVV IPCRGSISNL NVSLCARYPE KRFVPDGNRI SWDSEIGFTL PSYMISYAGM   180
VFCEAKINDE TYQSIMYIVV VVGYRIYDVI LSPPHEIELS AGEKLVLNCT ARTELNVGLD   240
FTWHSPPSKS HHKKIVNRDV KPFPGTVAKM FLSTLTIESV TKSDQGEYTC VASSGRMIKR   300
NRTFVRVHTK PFIAFGSGMK SLVEATVGSQ VRIPVKYLSY PAPDIKWYRN GRPIESNYTM   360
IVGDELTIME VTERDAGNYT VILTNPISME KQSHMVSLVV NVPPQIGEKA LISPMDSYQY   420
GTMQTLTCTV YANPPLHHIQ WYWQLEEEACS YRPGQTSPYA CKEEWRHVEF QGGNKIEVTK  480
NQYALIEGKN KTVSTLVIQA ANVSALYKCE AINKAGRGER VISFHVIRGP EITVQPAAQP   540
TEQESVSLLC TADRNTFENL TWYKLGSQAT SVHMGESLTP VCKNLDALWK LNGTMFSNST   600
NDILIVAFQN ASLQDQGDYV CSAQDKKTKK RHCLVKQLII LERMAPMITG NLENQTTTIG   660
ETIEVTCPAS GNPTPHITWF KDNETLVEDS GIVLRDGNRN LTIRRVRKED GGLYTCQACN   720
VLGCARAETL FIIEGAQEKT NLE                                           743

SEQ ID NO: 28           moltype = AA  length = 741
FEATURE                 Location/Qualifiers
source                  1..741
                        mol_type = protein
                        organism = Rattus sp.
                        note = Rat
SEQUENCE: 28
ASVGLPGDSL HPPKLSTQKD ILTILANTTL QITCRGQRDL DWLWPNTPRD SEERVLVTEC    60
GDSIFCKTLT VPRVVGNDTG AYKCFYRDTD VSSIVYVYVQ DHRSPFIASV SDEHGIVYIT   120
ENKNKTVVIP CRGSISNLNV SLCARYPEKR FVPDGNRISW DSEKGFTIPS YMISYAGMVF   180
CEAKINDETY QSIMYIVLVV GYRIYDVVLS PPHEIELSAG EKLVLNCTAR TELNVGLDFS   240
WQFPSSKHQH KKIVNRDVKS LPGTVAKMPL STLTIDSVTK SDQGEYTCTA YSGLMTKKNK   300
TFVRVHTKPF IAFGSGMKSL VEATVGSQVR IPVKYLSYPA PDIKWYRNGR PIESNYTMIV   360
GDELTIMEVS ERDAGNYTVI LTNPISMEKQ SHMVSLVVNV PPQIGEKALI SPMDSYQYGT   420
MQTLTCTVYA NPPLHHIQWY WQLEEECSYR PSQTNPYTCK EWRHVKDFQG GNKIEVTKNQ   480
YALIEGKNKT VSTLVIQAAY VSALYKCEAI NKAGRGERVI SFHVIRGPEI TVQPATQPTE   540
RESMSLLCTA DRNTFENLTW YKLGSQATSV HMGESLTPVC KNLDALWKLN GTVFSNSTND   600
ILIVAFQNAS LQDQGNYVCS AQDKKTKKRH CLVKQLVILE RMAPMITGNL ENQTTTIGET   660
IEVVCPTSGN PTPLITWFKD NETLVEDSGI VLKDGNRNLT IRRVRKEDGG LYTCQACNVL   720
GCARAETLFI IEGVQEKTNL E                                             741

SEQ ID NO: 29           moltype = AA  length = 756
FEATURE                 Location/Qualifiers
source                  1..756
                        mol_type = protein
                        organism = Homo sapiens
                        note = Human
SEQUENCE: 29
YSMTPPTLNI TEESHVIDTG DSLSISCRGQ HPLEWAWPGA QEAPATGDKD SEDTGVVRDC    60
EGTDARPYCK VLLLHEVHAN DTGSYVCYYK YIKARIEGTT AASSYVFVRD FEQPFINKPD   120
```

```
TLLVNRKDAM WVPCLVSIPG LNVTLRSQSS VLWPDGQEVV WDDRRGMLVS TPLLHDALYL    180
QCETTWGDQD FLSNPFLVHI TGNELYDIQL LPRKSLELLV GEKLVLNCTV WAEFNSGVTF    240
DWDYPGKQAE RGKWVPERRS QQTHTELSSI LTIHNVSQHD LGSYVCKANN GIQRFRESTE    300
VIVHENPFIS VEWLKGPILE ATAGDELVKL PVKLAAYPPP EFQWYKDGKA LSGRHSPHAL    360
VLKEVTEAST GTYTLALWNS AAGLRRNISL ELVVNVPPQI HEKEASSPSI YSRHSRQALT    420
CTAYGVPLPL SIQWHRPWT  PCKMFAQRSL RRRQQQDLMP QCRDWRAVTT QDAVNPIESL    480
DTWTEFVEGK NKTVSKLVIQ NANVSAMYKC VVSNKVGQDE RLIYFYVTTI PDGFTIESKP    540
SEELLEGQPV LLSCQADSYK YEHLRWYRLN LSTLHDAHGN PLLLDCKNVH LFATPLAASL    600
EEVAPGARHA TLSLSIPRVA PEHEGHYVCE VQDRRSHDKH CHKKYLSVQA LEAPRLTQNL    660
TDLLVNVSDS LEMQCLVAGA HAPSIVWYKD ERLLEEKSGV DLADSNQKLS IQRVREEDAG    720
RYLCSVCNAK GCVNSSASVA VEGSEDKGSM EIVILV                             756

SEQ ID NO: 30           moltype = AA   length = 751
FEATURE                 Location/Qualifiers
source                  1..751
                        mol_type = protein
                        organism = Mus sp.
                        note = Mouse
SEQUENCE: 30
YSMTPPTLNI TEDSYVIDTG DSLSISCRGQ HPLEWTWPGA QEVLTTGGKD SEDTRVVHDC    60
EGTEARPYCK VLLLAQTHAN NTGSYHCYYK YIKARIEGTT AASTYVFVRD FKHPFINKPD    120
TLLVNRKDSM WVPCLVSIPG LNITLRSQSS ALHPDGQEVL WDDRRGMRVP TQLLRDALYL    180
QCETTWGDQN FLSNLFVVHI TGNELYDIQL YPKKSMELLV GEKLVLNCTV WAEFDSGVTF    240
DWDYPGKQAE RAKWVPERRS QQTHTELSSI LTIHNVSQND LGPYVCEANN GIQRFRESTE    300
VIVHEKPFIS VEWLKGPVLE ATAGDELVKL PVKLAAYPPP EFQWYKDRKA VTGRHNPHAL    360
VLKEVTEASA GVYTLALWNS AAGLRQNISL ELVVNVPPHI HEKEASSPSI YSRHSRQTLT    420
CTAYGVPQPL SVQWHRPWT  PCKTFAQRSL RRRQQRDGMP QCRDWKEVTT QDAVNPIESL    480
DSWTEFVEGK NKTVSKLVIQ DANVSAMYKC VVVNKVGQDE RLIYFYVTTI PDGFSIESEP    540
SEDPLEGQSV RLSCRADNYT YEHLRWYRLN LSTLHDAQGN PLLLDCKNVH LFATPLEANL    600
EEAEPGARHA TLSLNIPRVA PEDEGDYVCE VQDRRSQDKH CHKKYLSVQA LEAPRLTQNL    660
TDLLVNVSDS LEMRCPVAGA HVPSIVWYKD ERLLEEKSGI DLADSNQRLS IQRVREEDAG    720
RYLCSVCNAK GCVNSSASVA VEGSEDKGSM E                                  751

SEQ ID NO: 31           moltype = AA   length = 751
FEATURE                 Location/Qualifiers
source                  1..751
                        mol_type = protein
                        organism = Rattus sp.
                        note = Rat
SEQUENCE: 31
YSMTPPTLNI TEDSYVIDTG DSLSISCRGQ HPLEWTWRGA QEVLTTGGKD SEDTQVVQDC    60
EGTEARPYCK VLSLAQTHAN NTGSYYCYYK YIKARIEGTT AASTYVFVRD FEQPFINKPD    120
TLLVNRKDSM WVPCLVSIPG LNITLRSQSS VLHPDGQEVL WDDRRGMRVP TLLLRDALYL    180
QCETTWGDQD FLSNPFLVHI TGNELYDIQL YPKKSLELLV GEKLVLNCTV WAEFDSGVTF    240
DWDYPGKQAE RAKWVPERRS QQTHTELSSI LTIHNVSQHD LGPYVCEANN GIQQFRESTE    300
VIVHEKPFIS VEWLKGPVLE ATAGDEMVKL PVKLAAYPPP EFQWYKDRKA VTGRHNPHAL    360
VLKEVTEASA GVYTLALWNS AAGLRQNISL ELVVNVPPHI HEKEASSPSI YSRHSRQTLT    420
CTTYGVPQPL SVQWHRPWT  PCKTFAQRSL RRRQPRDGMP QCRDWKEVTT QDAVNPIESL    480
DTWTESVEGK NKTVSKLVIQ DANVSAMYKC VVFNKVGQDE RLIYFYVTTI PDGFSIESEP    540
SEDPLEGQSV RLSCRADNYT YEHLRWYRLN LSTLHDAQGN PLLLDCKNVH LFATPLEANL    600
EEAEPGARHA TLSLNIPRVA PEDEGDYVCE VQDRRSQDKH CHKKYLSVQA LEAPRLTQNL    660
TDLLVNVRTS LEMRCPVAGA HVPSIVWYKD ERLLEEKSGI DLADSNQRLS IQRVREEDAG    720
RYLCSVCNAK GCVNSSASVA VEGSEDKGSM E                                  751

SEQ ID NO: 32           moltype = AA   length = 220
FEATURE                 Location/Qualifiers
source                  1..220
                        mol_type = protein
                        organism = Homo sapiens
                        note = Human
SEQUENCE: 32
PCPAPELLGG PSVFLFPPKP KDTLMISRTP EVTCVVVDVS HEDPEVKFNW YVDGVEVHNA    60
KTKPREEQYN STYRVVSVLT VLHQDWLNGK EYKCKVSNKA LPAPIEKTIS KAKGQPREPQ    120
VYTLPPSRDE LTKNQVSLTC LVKGFYPSDI AVEWESNGQP ENNYKTTPPV LDSDGSFFLY    180
SKLTVDKSRW QQGNVFSCSV MHEALHNHYT QKSLSLSPGK                         220

SEQ ID NO: 33           moltype = AA   length = 223
FEATURE                 Location/Qualifiers
source                  1..223
                        mol_type = protein
                        organism = Homo sapiens
                        note = Human
SEQUENCE: 33
VECPPCPAPP VAGPSVFLFP PKPKDTLMIS RTPEVTCVVV DVSHEDPEVQ FNWYVDGVEV    60
HNAKTKPREE QFNSTFRVVS VLTVVHQDWL NGKEYKCKVS NKGLPAPIEK TISKTKGQPR    120
EPQVYTLPPS REEMTKNQVS LTCLVKGFYP SDIAVEWESN GQPENNYKTT PPMLDSDGSF    180
FLYSKLTVDK SRWQQGNVFS CSVMHEALHN HYTQKSLSLS PGK                     223

SEQ ID NO: 34           moltype = AA   length = 223
```

```
FEATURE          Location/Qualifiers
source           1..223
                 mol_type = protein
                 organism = Homo sapiens
                 note = Human
SEQUENCE: 34
TCPRCPAPEL LGGPSVFLFP PKPKDTLMIS RTPEVTCVVV DVSHEDPEVQ FKWYVDGVEV    60
HNAKTKPREE QFNSTFRVVS VLTVLHQDWL NGKEYKCKVS NKALPAPIEK TISKTKGQPR   120
EPQVYTLPPS REEMTKNQVS LTCLVKGFYP SDIAVEWESS GQPENNYKTT PPMLDSDGSF   180
FLYSKLTVDK SRWQQGNIFS CSVMHEALHN RFTQKSLSLS PGK                     223

SEQ ID NO: 35           moltype = DNA  length = 4474
FEATURE                 Location/Qualifiers
misc_feature            1..4474
                        note = pITR.CBA.Bevacizumab
source                  1..4474
                        mol_type = other DNA
                        organism = synthetic construct
SEQUENCE: 35
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtgacatt gattattgac tagttattaa tagtaatcaa    180
ttacggggtc attagttcat agcccatata tggagttccg cgttacataa cttacggtaa    240
atggcccgcc tggctgaccg cccaacgacc cccgcccatt gacgtcaata atgacgtatg    300
ttcccatagt aacgccaata gggactttcc attgacgtca atgggtggac tatttacggt    360
aaactgccca cttggcagta catcaagtgt atcatatgcc aagtacgccc cctattgacg    420
tcaatgacgg taaatggccc gcctggcatt atgcccagta catgacctta tgggactttc    480
ctacttggca gtacatctac gtattagtca tcgctattac catgggtcga ggtgagcccc    540
acgttctgct tcactctccc catctcccce cctccccac cccaattttt gtatttattt     600
attttttaat tattttgtgc agcgatgggg gcggggggg gggggcgcg cgccaggcgg     660
ggcggggcgg ggcgagggc ggggcgggc gaggcggaga ggtgcggcgg cagccaatca    720
gagcggcgcg ctccgaaagt ttccttttat ggcgaggcgg cggcggcggc ggccctataa    780
aaagcgaagc gcgcggcggg cgggagtcgc tgcgttgcct tcgccccgtg cccgctccg     840
cgccgcctcg cgccgcccgc cccggctctg actgaccgcg ttactcccac aggtgagcgg    900
gcgggacggc ccttctcctc cgggctgtaa ttagcgcttg gtttaatgac ggctcgtttc    960
ttttctgtgg ctgcgtgaaa gccttaaagg gctccgggag ggccctttgt gcgggggga   1020
gcggctcggg gggtgcgtgc gtgtgtgtgt gcgtgggga gcgccgcgtgc ggcccgcgct  1080
gcccggcggc tgtgagcgct gcgggcgcgg cgcggggctt tgtgcgctcc gcgtgtgcgc   1140
gaggggagcg cggccggggg ccgtgcgtg gggctgcgag gggaacaaag                1200
gctgcgtgcg gggtgtgtgc gtgggggggt gagcaggggg tgtgggcgcg gcggtcgggc   1260
tgtaaccccc cctgcaccc ccctccccga gttgctgagc acggcccggc ttcgggtgcg   1320
gggctccgtg cggggcgtgg cgcggggctc gccgtgccgg gcggggggtg gcggcaggtg    1380
ggggtgcgtg gcggggcggg gccgcctcgg gccgggagga gtcggggga ggggcgcggc   1440
ggccccgga gcgccggcgg ctgtcgaggc gcggcgagcc gcagccattg cctttttatgt   1500
taatcgtgcg agagggcgca gggacttcct ttgtcccaaa tctgtgcgga gccgaaatct    1560
gggaggcgc gccgcacccc ctctagcggg cgcggggcga agcggtgcgg cgccggcagg    1620
aaggaaatgg gcggggaggg ccttcgtgcg tcgccgcgcc gccgtcccct tctccctctc    1680
cagcctcggg gctgtccgcg ggggacggc tgccttcggg ggggacgggg cagggcgggg    1740
ttcggcttct ggcgtgtgac cggcggctct agagcctctg ctaaccatgt tcatgccttc    1800
ttcttttttcc tacagctcct gggcaacgtg ctggttattg tgaccggtgc caccatgtac    1860
cggatgcagc tgctgagctg tatcgccctg tctctggcc tggtcaccaa ttctgaggtg    1920
cagctggtgg aatctggcgg cggacttgtt caacctggcg gctctctgag actgagctgt    1980
gccgcttctg gctacacctt caccaactac ggcatgaact gggtccgaca ggcccctggc    2040
aaaggccttg aatgggtcgg atggatcaac acctacaccg gcgagccaac atacgccgcc    2100
gacttcaagc ggagattcac cttcagcctg gacaccagca agaccaccgc ctacctgcag    2160
atgaacagcc tgagagccga ggacaccgcc gtgtactact gcgccaagta tccccactac    2220
tacggcagca gccactggta ctttgacgtg tggggacagg gcacactggt cacagtgtct    2280
agcgcctcta caagggccc cagcgttttc ccactggctc ctagcagcaa gtctaccagc    2340
ggaggaacag ccgctctggg ctgtctggtc aaggactact tcccgagcc tgtgaccgtg    2400
tcctggaatt ctggcgctct gacaagcggc gtgcacacct tccagctgt gctgcaaagc    2460
agcggcctgt actctctgag cagcgtcgtg acagtgccaa gcagctctct gggcacccag    2520
acctacatct gcaatgtgaa ccacaagcct agcaacacca aggtggacaa gaaggtggaa    2580
cccaagagct gcgacaagac ccacacctgt cctccatgtc ctgctccaga actgctcggc    2640
ggaccttccg tgttcctgtt tcctccaaag cctaaggaca cctgatgat cagcagaacc    2700
cctgaagtga cctgcgtggt ggtggatgtg tcccacgagg atcccgaagt gaagttcaat    2760
tggtacgtgg acggcgtgga agtgcacaac gccaagacca gcctagaga gaacagtac    2820
aacagcacct acagagtggt gtccgtgctg accgtgctgc accaggattg gctgaacggc    2880
aaagagtaca agtgcaaggt gtccaacaag gccctgcct ctcctatcga gaaaaccatc    2940
agcaaggcca agggccagcc tagggaaccc caggtttaca cactgcctcc aagccggaa    3000
gagatgacca gaaccaggt gtccctgacc tgcctcgtga agggcttcta cccttccgat    3060
atcgccgtgg aatgggagag caatggccag ccagagaaca actacaagac aaccctcct    3120
gtgctggaca gcgacggctc attcttcctg tacagcaagc tgacagtgga caagtccaga    3180
tggcagcagg gcaacgtgtt cagctgcagc gtgatgcacg aggccctgca caaccactac    3240
acccagaagt ctctgagcct gtctccgggc aagcgaaa aagcctc gaaagc           3300
agaggcagcc tgcttacatg tggcgacgtg gaagagaacc ccggacctat gtatagaatg    3360
cagctcctgt cctgcattgc cctgagcctg gctctcgtga ccaacagcga catccagatg    3420
acacagagcc cagcagcct gtctgcctct gtggagacag agtgaccat cacctgtagc    3480
gccagccagg acatctccaa ctacctgaac tggtatcagc aaaagcccgg caaggcccct    3540
aaggtgctga tctacttcac aagcagcctg cactccggcg tgcccagcag attttctggc    3600
```

```
tctggcagcg gcaccgactt caccctgacc atatctagcc tgcagcctga ggacttcgcc   3660
acctactact gccagcagta cagcaccgtg ccttggacat ttggccaggg cacaaaggtg   3720
gaaatcaagc ggactgtggc cgctcctagc gtgttcatct ttccacctag cgacgagcag   3780
ctgaagtctg gcacagcctc tgtcgtgtgc ctgctgaaca acttctaccc cagagaagcc   3840
aaggtgcagt ggaaagtgga caatgccctg cagagccgga acagccaaga gagcgtgaca   3900
gagcaggact ccaaggatag cacctatagc ctgagcagca ccctgacact gagcaaggcc   3960
gactacgaga agcacaaagt gtacgcctgc gaagtgaccc accagggcct ttctagccct   4020
gtgaccaaga gcttcaaccg gggcgaatgt taagagctcg ctgatcagcc tcgactgtgc   4080
cttctagttg ccagccatct gttgtttgcc cctcccccgt gccttccttg accctggaag   4140
gtgccactcc cactgtcctt tcctaataaa atgaggaaat tgcatcgcat tgtctgagta   4200
ggtgtcattc tattctgggg ggtggggtgg ggcaggacag caaggggag gattgggaag   4260
acaatagcag gcatgctggg gatgcggtgg gctctatgga agcttgaatt cagctgacgt   4320
gcctcggacc gctaggaacc cctagtgatg gagttggcca ctccctctct gcgcgctcgc   4380
tcgctcactg aggccgggcg accaaaggtc gcccgacgcc cgggctttgc ccgggcggcc   4440
tcagtgagcg agcgagcgcg cagctgcctg cagg                               4474

SEQ ID NO: 36           moltype = DNA  length = 144
FEATURE                 Location/Qualifiers
misc_feature            1..144
                        note = ITR sequence
source                  1..144
                        mol_type = other DNA
                        organism = synthetic construct
SEQUENCE: 36
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggccgcac gcgt                                          144

SEQ ID NO: 37           moltype = DNA  length = 1671
FEATURE                 Location/Qualifiers
misc_feature            1..1671
                        note = CBA sequence
source                  1..1671
                        mol_type = other DNA
                        organism = synthetic construct
SEQUENCE: 37
gacattgatt attgactagt tattaatagt aatcaattac ggggtcatta gttcatagcc   60
catatatgga gttccgcgtt acataactta cggtaaatgg cccgcctggc tgaccgccca   120
acgacccccg cccattgacg tcaataatga cgtatgttcc catagtaacg ccaatagggα   180
ctttccattg acgtcaatgg gtggactatt tacggtaaac tgcccacttg gcagtacatc   240
aagtgtatca tatgccaagt acgccccta ttgacgtcaa tgacggtaaa tggcccgcct   300
ggcattatgc ccagtacatg accttatggg actttcctac ttggcagtac atctacgtat   360
tagtcatcgc tattaccatg gtcgaggtg agccccacgt tctgcttcac tctccccatc   420
tcccccccct ccccaccccc aattttgtat ttatttattt tttaattatt ttgtgcagcg   480
atgggggcgg ggggggggg ggcgcgcgcc aggcggggcg gggcggggcg aggggcgggg   540
cggggcgagg cggagaggtg cggcggcagc caatcagagc ggcgcgctcc gaaagtttcc   600
ttttatgcg aggccggcc ggccggcc ctataaaaag cgaagcgcgc ggcgggcggg   660
agtcgctgcg ttgccttcgc cccgtgcccc gctccgcgcc gcctcgcgcc gcccgccccg   720
gctctgactg accgcgttac tcccacaggt gagcgggcgg gacggccctt ctcctccggg   780
ctgtaattag cgcttggttt aatgacggct cgtttctttt ctgtggctgc gtgaaagcct   840
taaagggctc cggagggcc ctttgtgcgg gggagcgg ctcggggggt gcgtgcgtgt   900
gtgtgtgcgt ggggagcgcc gcgtgcggcc cgcgctgccc ggcggctgtg agcgctgcgg   960
gcgcggcgcg gggctttgtg cgctccgcgt gtgcgcgagg ggagcgcggc cggggcggt   1020
gccccgcggt gcgggggggc tgcgagggga caaaggctg cgtgcggggt gtgtgcgtgg   1080
ggggtgagc aggggtgtg ggcgcggcgg tcgggctgta acccccccct gcacccccct   1140
ccccgagttg ctgagcacgg cccggcttcg ggtgcgggc tccgtacggg gcgtggcgcg   1200
gggctcgccg tgccgggcgg ggggtggcgg caggtggggg tgccgggcgg ggcggggccg   1260
cctcgggcc gggaggggctc gggggagggg cgcggcggcc cccggagcgc cggcggctgt   1320
cgaggcgcgg cgagccgcag ccattgcctt ttatggtaat cgtgcgagag ggcgcaggga   1380
cttcctttgt cccaaatctg tgcggagccg aaatctggga gccgccgcg caccccctct   1440
agcgggcgcg gggcgaagcg gtgcggcgcc ggcaggaagg aaatgggcgg gagggccttt   1500
cgtgcgtcgc cgcgccgccg tccccttctc cctctccagc ctcggggctg tccgcggggg   1560
gacggctgcc ttcggggggg acggggcagg gcggggttcg gcttctggcg tgtgaccggc   1620
ggctctagag cctctgctaa ccatgttcat gccttcttct ttttcctaca g            1671

SEQ ID NO: 38           moltype = DNA  length = 39
FEATURE                 Location/Qualifiers
misc_feature            1..39
                        note = spacer
source                  1..39
                        mol_type = other DNA
                        organism = synthetic construct
SEQUENCE: 38
ctcctgggca acgtgctggt tattgtgacc ggtgccacc                           39

SEQ ID NO: 39           moltype = DNA  length = 60
FEATURE                 Location/Qualifiers
misc_feature            1..60
                        note = IL-2 secretion signal sequence
```

```
source                  1..60
                        mol_type = other DNA
                        organism = synthetic construct
SEQUENCE: 39
atgtaccgga tgcagctgct gagctgtatc gccctgtctc tggccctggt caccaattct  60

SEQ ID NO: 40           moltype = DNA  length = 1359
FEATURE                 Location/Qualifiers
misc_feature            1..1359
                        note = Sequence encoding heavy chain of bevacizumab
source                  1..1359
                        mol_type = other DNA
                        organism = synthetic construct
SEQUENCE: 40
gaggtgcagc tggtggaatc tggcggcgga cttgttcaac ctggcggctc tctgagactg   60
agctgtgccg cttctggcta caccttcacc aactacggca tgaactgggt ccgacaggcc  120
cctggcaaag gccttgaatg ggtcggatgg atcaacacct acaccggcga gccaaacatac 180
gccgccgact tcaagcggag attcaccttc agcctggaca ccagcaagtc caccgcctac  240
ctgcagatga acagcctgag agccgaggac accgccgtgt actactgcgc caagtatccc  300
cactactacg gcagcagcca ctggtacttt gactgtgggg acagggcac actggtcaca  360
gtgtctagcg cctctacaaa gggccccagc gttttccac tggctcctag cagcaagtct  420
accagcggag aacagccgc tctggctgt ctggtcaagg actactttcc cgagcctgtg  480
accgtgtcct ggaattctgg cgctctgaca agcggcgtgc acaccttttcc agctgtgctg  540
caaagcagcg gcctgtactc tctgagcagc gtcgtgacag tgccaagcag ctctctgggc  600
acccagacct acatctgcaa tgtgaaccac aagcctagca caccaaggt ggacaagaag  660
gtggaaccca gagctgcga caagacccac acctgtcctc catgtcctgc tccagaactg  720
ctcggcggac cttccgtgtt cctgtttcct ccaaagccta aggacaccct gatgatcagc  780
agaacccctg aagtgacctg cgtggtggtg gatgtgtccc acgaggatcc cgaagtgaag  840
ttcaattggt acgtggacgg cgtggaagtg cacaacgcca agaccaagcc tagagaggaa  900
cagtacaaca gcacctacag agtggtgtcc gtgctgaccg tgctgcacca ggattggctg  960
aacggcaaag agtacaagtg caaggtgtcc aacaaggccc tgcctgctcc tatcgaaaa  1020
accatcagca aggccaaggg ccagcctagg aacccagg tttacacact gcctccaagc  1080
cgggaagaga tgaccaagaa ccaggtgtcc ctgacctgcc tcgtgaaggg cttctacect  1140
tccgatatcg ccgtggaatg ggagagcaat ggccagccag agaacaacta caagacaacc  1200
cctcctgtgc tggacagcga cggctcattc ttcctgtaca gcaagctgac agtggacaag  1260
tccagatggc agcagggcaa cgtgttcagc tgcagcgtga tgcacgaggc cctgcacaac  1320
cactacaccc agaagtctct gagcctgtct cctggcaag                        1359

SEQ ID NO: 41           moltype = DNA  length = 12
FEATURE                 Location/Qualifiers
misc_feature            1..12
                        note = Linker sequence
source                  1..12
                        mol_type = other DNA
                        organism = synthetic construct
SEQUENCE: 41
cggaagagaa ga                                                       12

SEQ ID NO: 42           moltype = DNA  length = 63
FEATURE                 Location/Qualifiers
misc_feature            1..63
                        note = T2A sequence
source                  1..63
                        mol_type = other DNA
                        organism = synthetic construct
SEQUENCE: 42
ggctctggcg aaggcagagg cagcctgctt acatgtggcg acgtggaaga gaaccccgga  60
cct                                                                63

SEQ ID NO: 43           moltype = DNA  length = 60
FEATURE                 Location/Qualifiers
misc_feature            1..60
                        note = IL-2 secretion signal sequence
source                  1..60
                        mol_type = other DNA
                        organism = synthetic construct
SEQUENCE: 43
atgtatagaa tgcagctcct gtcctgcatt gccctgagcc tggctctcgt gaccaacagc  60

SEQ ID NO: 44           moltype = DNA  length = 645
FEATURE                 Location/Qualifiers
misc_feature            1..645
                        note = Sequence encoding light chain of bevacizumab
source                  1..645
                        mol_type = other DNA
                        organism = synthetic construct
SEQUENCE: 44
gacatccaga tgacacagag ccccagcagc ctgtctgcct ctgtgggaga cagagtgacc  60
atcacctgta gcgccagcca ggacatctcc aactacctga actggtatca gcaaaagccc 120
```

```
ggcaaggccc ctaaggtgct gatctacttc acaagcagcc tgcactccgg cgtgcccagc    180
agattttctg gctctggcag cggcaccgac ttcaccctga ccatatctag cctgcagcct    240
gaggacttcg ccacctacta ctgccagcag tacagcaccg tgccttggac atttggccag    300
ggcacaaagg tggaaatcaa gcggactgtg gccgctccta gcgtgttcat ctttccacct    360
agcgacgagc agctgaagtc tggcacagcc tctgtcgtgt gcctgctgaa caacttctac    420
cccagagaag ccaaggtgca gtggaaagtg gacaatgccc tgcagagcgg caacagccaa    480
gagagcgtga cagagcagga ctccaaggat agcacctata gcctgagcag cacccctgaca   540
ctgagcaagg ccgactacga gaagcacaaa gtgtacgcct gcgaagtgac caccagggc    600
ctttctagcc ctgtgaccaa gagcttcaac cggggcgaat gttaa                    645

SEQ ID NO: 45           moltype = DNA  length = 21
FEATURE                 Location/Qualifiers
misc_feature            1..21
                        note = Linker sequence
source                  1..21
                        mol_type = other DNA
                        organism = synthetic construct
SEQUENCE: 45
gagctcgctg atcagcctcg a                                               21

SEQ ID NO: 46           moltype = DNA  length = 225
FEATURE                 Location/Qualifiers
misc_feature            1..225
                        note = Bovine growth hormone polyA tail sequence
source                  1..225
                        mol_type = other DNA
                        organism = synthetic construct
SEQUENCE: 46
ctgtgccttc tagttgccag ccatctgttg tttgccccctc cccgtgcct tccttgaccc     60
tggaaggtgc cactcccact gtcctttcct aataaaatga ggaaattgca tcgcattgtc    120
tgagtaggtg tcattctatt ctggggggtg ggtgggcca ggacagcaag ggggaggatt    180
gggaagacaa tagcaggcat gctggggatg cggtgggctc tatgg                    225

SEQ ID NO: 47           moltype = DNA  length = 34
FEATURE                 Location/Qualifiers
misc_feature            1..34
                        note = Linker sequence
source                  1..34
                        mol_type = other DNA
                        organism = synthetic construct
SEQUENCE: 47
aagcttgaat tcagctgacg tgcctcggac cgct                                 34

SEQ ID NO: 48           moltype = DNA  length = 141
FEATURE                 Location/Qualifiers
misc_feature            1..141
                        note = ITR
source                  1..141
                        mol_type = other DNA
                        organism = synthetic construct
SEQUENCE: 48
aggaacccct agtgatggag ttggccactc cctctctgcg cgctcgctcg ctcactgagg     60
ccgggcgacc aaaggtcgcc cgacgcccgg gctttgcccg gcggcctca gtgagcgagc    120
gagcgcgcag ctgcctgcag g                                              141

SEQ ID NO: 49           moltype = AA  length = 20
FEATURE                 Location/Qualifiers
REGION                  1..20
                        note = IL-2 signal sequence
source                  1..20
                        mol_type = protein
                        organism = synthetic construct
SEQUENCE: 49
MYRMQLLSCI ALSLALVTNS                                                 20

SEQ ID NO: 50           moltype = AA  length = 21
FEATURE                 Location/Qualifiers
REGION                  1..21
                        note = T2A sequence
source                  1..21
                        mol_type = protein
                        organism = synthetic construct
SEQUENCE: 50
GSGEGRGSLL TCGDVEENPG P                                               21

SEQ ID NO: 51           moltype = DNA  length = 3814
FEATURE                 Location/Qualifiers
misc_feature            1..3814
                        note = pITR.CBA.lucentis
```

| source | 1..3814 |
| --- | --- |
| | mol_type = other DNA |
| | organism = synthetic construct |

SEQUENCE: 51

```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggccgcac gcgtgacatt gattattgac tagttattaa tagtaatcaa   180
ttacggggtc attagttcat agcccatata tggagttccg cgttacataa cttacggtaa   240
atggcccgcc tggctgaccg cccaacgacc cccgcccatt gacgtcaata atgacgtatg   300
ttcccatagt aacgccaata gggactttcc attgacgtca atgggtggac tatttacggt   360
aaactgccca cttggcagta catcaagtgt atcatatgcc aagtacgccc cctattgacg   420
tcaatgacgg taaatggccc gcctggcatt atgcccagta catgacctta tgggactttc   480
ctacttggca gtacatctac gtattagtca tcgctattac catgggtcga ggtgagcccc   540
acgttctgct tcactctccc catctccccc ccctcccac ccccaatttt gtatttattt   600
attttttaat tattttgtgc agcgatgggg gcggggggg gggggcgcg cgccaggcgg   660
ggcggggcgg ggcgagggc ggggcgggc gaggcgaga ggtgcggcgg cagccaatca   720
gagcggcgcg ctccgaaagt ttcctttat ggcgaggcg cggcggcggc ggccctaaa   780
aaagcgaagc gcgcggcggg cgggagtcgc tgcgttgcct tcgcccgtg ccccgctccg   840
cgccgcctcg cgccgcccgc cccggctctg actgaccgcg ttactccac aggtgagcgg   900
gcgggacggc ccttctcctc cgggctgtaa ttagcgcttg gtttaatgac ggctcgttc   960
ttttctgtgg ctgcgtgaaa gccttaaagg gctccggag ggccctttgt gcgggggga  1020
gcggctcggg ggtgcgtgc gtgtgtgtgt gcgtgggag ccgcgtgc gcccgcgct  1080
gcccggcggc tgtgagcgct gcgggcgcgg cgcgggctt tgtgcgctcc gcgtgtgcgc  1140
gagggagcg cggccggg cggtgcccg cggtgcggg gggctgcgag gggaacaaag  1200
gctgcgtgcg gggtgtgtgc gtggggggt gagcagggg tgtgggcgcg gcggtcgggc  1260
tgtaaccccc ccctgcaccc ccctcccga gttgctgaca acggcccggc ttcgggtccg  1320
gggctccgtg cggggcgtgg gcgcgggctc gccgtgccgg gcggggggtg gcggcaggtg  1380
ggggtgccgg gcggggcggg gccgcctcgg gccggggagg gctcgggga ggggcgcggc  1440
ggcccccgga gcgccggcgg ctgtcgaggc gcggcgagcc gcagccattg ccttttatgg  1500
taatcgtgcg agagggcgca gggacttcct ttgtcccaaa tctgtgcgga gccgaaatct  1560
gggaggcgcc gccgcacccc ctctagcggg cgcgggcga agcggtgcgg cgccggcagg  1620
aaggaaatgg gcggggaggg ccttcgtgcg tcgccgcgcc gccgtcccct tctccctctc  1680
cagcctcggg gctgtccgcg gggggacggc tgccttcggg ggggacgggg cagggcgggg  1740
ttcggcttct ggcgtgtgac cggcggctct agagcctctg ctaaccatgt tcatgccttc  1800
ttcttttttcc tacagctcct gggcaacgtg ctggttattg tgaccggtgc caccatgtac  1860
cggatgcagc tgctgagctg tatcgccctg tctctggccc tggtcaccaa ttctgaggtg  1920
cagctggtgg aatctggcgg cggacttgtt caacctggcg gctctctgag actgagctgt  1980
gccgcttctg gctacgactt cacccactac ggcatgaact gggtccgaca ggcccctggc  2040
aaaggccttg aatgggtcgg atggatcaac acctacaccg gcgagccaac atacgccgcc  2100
gacttcaagc ggagattcac cttcagcctg gacaccagca gagcaccgc ctacctgcag  2160
atgaacagcc tgagagccga ggacaccgcc gtgtactact gcgccaagta tccctactac  2220
tacggcacca gccactggta ctttgacgtg tggggacagg gcacactggt cacagtgtct  2280
agcgcctcta caaagggccc cagcgttttc ccactgcca ctagcagcaa gtctaccagc  2340
ggaggaacag ccgctctggg ctgtctggtc aaggactact tccccgagcc tgtgaccgtg  2400
tcctggaatt ctggcgctct gacaagcggg gtgcacacct ttccagctgt gctgcaaagc  2460
agcggcctgt actctctgag cagcgtcgtg acagtgccaa gcagctctct gggcacccag  2520
acctacatct gcaatgtgaa ccacaagcct agcaacaca agtggacaa gaaggtggaa  2580
cccaagagct gcgacaagac ccacaccggc aagcggaaga gaaggctc tggcgaaggc  2640
agaggcagcc tgcttacatg tggcgacgtg aagagaacc ccggacctat gtatagaatg  2700
cagctcctgt cctgcattgc cctgagcctg gctctcgtga ccaacagcga catccagctg  2760
acacagagcc ccagcagcct gtctgcctct gtgggagaca gagtgaccat cacctgtagg  2820
gccagcagg acatctccaa ctacctgaac tggtatcagc aaaagccgg caaggcccct  2880
aaggtgctga tctacttcac aagcagcctg cactccggcg tgcccagcag attttctggc  2940
tctggcagcg gcaccgactt caccctgacc atatctagcc tgcagcctga ggacttcgcc  3000
acctactact gccagcagta cagcaccgtg ccttggacgt tggccaggg acaaaaggtg  3060
gaaatcaagc ggactgtggc cgctcctagc gtgttcatct ttccacctag cgacgagcag  3120
ctgaagtctg gcacagcctc tgtcgtgtgc ctgctgaaca acttctaccc cagagaagcc  3180
aaggtgcagt ggaagtggaa caatgcctg cagagcggaa acagccaaga gagcgtgaca  3240
gagcaggact ccaaggatag cacctatagc ctgagcagca cctgcactt gacgcaaggcc  3300
gactacgaga agcacaaagt gtacgcctgc gaagtgaccc accagggcct ttctagccct  3360
gtgaccaaga gcttcaaccg gggcgaatgt taagagctcg ctgatcagcc tcgactgtgc  3420
cttctagttg ccagccatct gttgtttgcc cctcccccgt gccttccttg accctggaag  3480
gtgccactcc cactgtcctt tcctaataaa atgaggaaat tgcatcgcat tgtctgagta  3540
ggtgtcattc tattctgggg gtggggtgg gcaggacaga caagggggag gattgggaa  3600
acaatagcag gcatgctggg gatgcggtgg gctctatggg agcttgaatt cagctgacgt  3660
gcctcggacc gctaggaacc cctagtgatg gagttggcca ctccctctct gcgcgctcgc  3720
tcgctcactg aggccgggcg accaaaggtc gcccgacgcc cgggctttgc ccgggcggcc  3780
tcagtgagcg agcgagcgcg cagctgcctg cagg                               3814
```

| SEQ ID NO: 52 | moltype = DNA length = 699 |
| --- | --- |
| FEATURE | Location/Qualifiers |
| misc_feature | 1..699 |
| | note = Sequence encoding ranibizumab heavy chain |
| source | 1..699 |
| | mol_type = other DNA |
| | organism = synthetic construct |

SEQUENCE: 52

```
gaggtgcagc tggtggaatc tggcggcgga cttgttcaac tggcggctc tctgagactg    60
agctgtgccc ttctggcta cgacttcacc cactacggca tgaactgggt ccgacaggcc   120
```

```
cctggcaaag gccttgaatg ggtcggatgg atcaacacct acaccggcga gccaacatac    180
gccgccgact tcaagcggag attcaccttc agcctggaca ccagcaagag caccgcctac    240
ctgcagatga acagcctgag agccgaggac accgccgtgt actactgcgc caagtatccc    300
tactactacg gcaccagcca ctggtacttt gacgtgtggg gacagggcac actggtcaca    360
gtgtctagcg cctctacaaa gggccccagc gtttccccac tggctcctag cagcaagtct    420
accagcggag gaacagccgc tctgggctgt ctggtcaagg actactttcc cgagcctgtg    480
accgtgtcct ggaattctgg cgctctgaca agcggcgtgc acacctttcc agctgtgctg    540
caaagcagcg gcctgtactc tctgagcagc gtcgtgacag tgccaagcag ctctctgggc    600
acccagacct acatctgcaa tgtgaaccac aagcctagca caccaaggt ggacaagaag    660
gtggaaccca agagctgcga caagacccac accggcaag                          699

SEQ ID NO: 53            moltype = DNA   length = 645
FEATURE                  Location/Qualifiers
misc_feature             1..645
                         note = Sequence encoding ranibizumab light chain
source                   1..645
                         mol_type = other DNA
                         organism = synthetic construct
SEQUENCE: 53
gacatccagc tgacacagag ccccagcagc ctgtctgcct ctgtgggaga cagagtgacc    60
atcacctgta gcgccagcca ggacatctcc aactacctga ctggtatca gcaaaagccc    120
ggcaaggccc ctaaggtgct gatctacttc acaagcagcc tgcactccgg cgtgcccagc    180
agatttctg gctctggcag cggcaccgac ttcaccctga ccatatctag cctgcagcct    240
gaggacttcg ccacctacta ctgccagcag tacagcaccg tgccttggac atttggccag    300
ggcacaaagg tggaaatcaa gcggactgtg gccgctccta gcgtgttcat cttcccacct    360
agcgacgagc agctgaagtc tggcacagcc tctgtcgtgt gcctgctgaa caacttctac    420
cccagagaag ccaaggtgca gtggaaagtg gacaatgccc tgcagagcgg caacagccaa    480
gagagcgtga cagagcagga ctccaaggat agcacctata gcctgagcag caccctgaca    540
ctgagcaagg ccgactacga gaagcacaaa gtgtacgcct gcgaagtgac ccaccagggc    600
cttttctagcc ctgtgaccaa gagcttcaac cggggcgaat gttaa                    645

SEQ ID NO: 54            moltype = AA   length = 233
FEATURE                  Location/Qualifiers
REGION                   1..233
                         note = Ranibizumab Heavy Chain
source                   1..233
                         mol_type = protein
                         organism = synthetic construct
SEQUENCE: 54
EVQLVESGGG LVQPGGSLRL SCAASGYDFT HYGMNWVRQA PGKGLEWVGW INTYTGEPTY    60
AADFKRRFTF SLDTSKSTAY LQMNSLRAED TAVYYCAKYP YYYGTSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TGK           233

SEQ ID NO: 55            moltype = DNA   length = 4573
FEATURE                  Location/Qualifiers
misc_feature             1..4573
                         note = pITR.CBA.Lucentis.tGFP
source                   1..4573
                         mol_type = other DNA
                         organism = synthetic construct
SEQUENCE: 55
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact    120
aggggttcct gcggccgcac gcgtgacatt gattattgac tagttattaa tagtaatcaa    180
ttacggggtc attagttcat agcccatata tggagttccg cgttacataa cttacggtaa    240
atggcccgcc tggctgaccg cccaacgacc cccgcccatt gacgtcaata atgacgtatg    300
ttcccatagt aacgccaata gggactttcc attgacgtca atgggtggac tatttacggt    360
aaactgccca cttggcagta catcaagtgt atcatatgcc aagtacgccc cctattgacg    420
tcaatgacgg taaatggccc gcctggcatt atgcccagta catgacctta tgggactttc    480
ctacttggca gtacatctac gtattagtca tcgctattac catgggtcga ggtgagcccc    540
acgttctgct tcactctccc catctccccc cctccccac cccaatttt gtatttattt    600
attttttaat tattttgtgc agcgatgggg gcgggggggg ggggggcgcg cgccaggcgg    660
ggcggggcgg ggcgaggggc ggggcggggc gaggcggaga ggtgcggcgg cagccaatca    720
gagcggcgcg ctccgaaagt ttccttttat ggcgaggcgg cggcggcggc ggccctataa    780
aaagcgaagc gcgcggcggg cgggagtcgc tgcgttgcct tcgccccgtg ccccgctccg    840
cgccgcctcg cgccgcccgc cccggctctg actaccgcg ttactccac aggtgagcgg    900
gcgggacggc ccttctcctc cgggctgtaa ttagcgcttg gtttaatgac ggctcgtttc    960
ttttctgtgg ctgcgtgaaa gccttaaagg gctccggag gcgggggga gggggggga    1020
gcggctcggg ggtcgtgtgc gtgtgtgtgt gcgtggggga cgcgcgtgc ggcccgcgct    1080
gcccggcggc tgtgagcgct gcgggcgcgg cgcggggctt tgtgcgctcc gcgtgtgcgc    1140
gagggggagcg cggccgggg cggtgccccg cggtgcgggg gggctgcgag gggaacaaag    1200
gctgcgtgcg gggtgtgtgc gtggggggt gagcagggg tgtgggcgcg gcggtcgggc    1260
tgtaaccggg ccctgccacc ccctccccga gttgctgagc aagttgggg ttcggggga    1320
gggctccgtc cggggctggg gcgcgggctc gccgtgccgg gcgggggtg cggcaggtg    1380
gggtgccgg gcggggcggg gccgcctcgg gccggggagg gctcggggga ggggcgcggc    1440
ggcccccgga gcgccggcgg ctgtcgaggc gcggcgagcc gcagccattg ccttttatgg    1500
taatcgtgcg agaggggcgca gggacttcct ttgtcccaaa tctgtgcgga gccgaaatct    1560
gggaggcgcc gccgcacccc ctctagcggg cgcggggcga agcggtgcgg cgccggcagg    1620
```

```
aaggaaatgg gcggggaggg ccttcgtgcg tcgccgcgcc gccgtcccct tctccctctc 1680
cagcctcggg gctgtccgcg gggggacggg tgccttcggg ggggacgggg cagggcgggg 1740
ttcggcttct ggcgtgtgac cggcggctct agagcctctg ctaaccatgt tcatgccttc 1800
ttcttttttcc tacagctcct gggcaacgtg ctggttattg tgaccggtgc caccatgtac 1860
cggatgcagc tgctgagctg tatcgccctg tctctggccc tggtcaccaa ttctgaggtg 1920
cagctggtgg aatctggcgg cggacttgtt caacctggcg gctctctgag actgagctgt 1980
gccgcttctg gctacgactt cacccactac ggcatgaact gggtccgaca ggcccctggc 2040
aaaggccttg aatgggtcgg atggatcaac acctacaccg gcgagccaac atacgccgcc 2100
gacttcaagc ggagattcac cttcagcctg gacaccagca agagcaccgc ctacctgcag 2160
atgaacagcc tgagagccga ggacaccgcc gtgtactact gcgccaagta tccctactac 2220
tacggcacca gccactggta ctttgacgtg tggggacagg gcacactggt cacagtgtct 2280
agcgcctcta caaagggccc cagcgttttc ccactggctc ctagcagcaa gtctaccagc 2340
ggaggaacag ccgctctggg ctgtctggtc aaggactact ttcccgagcc tgtgaccgtg 2400
tcctggaatt ctggcgctct gacaagcggc gtgcacacct tccagctgt gctgcaaagc 2460
agcggcctgt actctctgag cagcgtcgtg acagtgccaa gcagctctct gggcacccag 2520
acctacatct gcaatgtgaa ccacaagcct agcaacacca aggtgacaa gaaggtggaa 2580
cccaagagct gcgacaagac ccacaccggc aagcggaaga agagggctc tggcgaaggc 2640
agaggcagcc tgcttacatg tggcgacgtg gaagagaacc ccggacctat gtatagaatg 2700
cagctcctgt cctgcattgc cctgagcctg gctctcgtga ccaacagcga catccagctg 2760
acacagagcc ccagcagcct gtctgcctct gtgggagaca gagtgaccat cacctgtagc 2820
gccagccagg acatctccaa ctacctgaac tggtatcagc aaaagcccgg caaggcccct 2880
aaggtgctga tctacttcac aagcagcctg cactccggca tgcccagcag attttctggc 2940
tctggcagcg gcaccgactt caccctgacc atatctagcc tgcagcctga ggacttcgcc 3000
acctactact gccagcagta cagcaccgtg ccttggacat ttggccaggg cacaaaggtg 3060
gaaatcaagc ggactgtggc cgctcctagc gtgttcatct ttccacctag cgacgagcag 3120
ctgaagtctg gcacagcctc tgtcgtgtgc ctgctgaaca acttctaccc cagagaagcc 3180
aaggtgcagt ggaaagtgga caatgccctg cagagcggca acagccaaga gagcgtgaca 3240
gagcaggact ccaaggatag cacctatagc ctgagcagca ccctgacact gagcaaggcc 3300
gactacgaga agcacaaagt gtacgcctgc gaagtgaccc accagggcct ttctagccct 3360
gtgaccaaga gcttcaaccg gggcgaatgt ggctccggaa agggcagagg aagtctgcta 3420
acatgcggtg acgtcgagga gaatcctggc ccaatggagg gcgacgagag cggcctgccc 3480
gccatggaga tcgagtgccg catcaccggc accctgaacg gcgtggagtt cgagctggtg 3540
ggcggcggag agggcacccc cgagcagggc cgcatgacca acaagatgaa gagcaccaaa 3600
ggcgccctga ccttcagccc ctacctgctg agccacgtga tgggctacgg cttctaccac 3660
ttcggcacct accccgacgg ctacgaagac cccttcctgc acgccatcaa caacggcgcc 3720
tacaccaaca cccgcatcga gaagtacgag gacggcggcg tgctgcacgt gagcttcagc 3780
taccgctacg aggccggccg cgtgatcggc gacttcaagg tgatgggcac cggcttcccc 3840
gaggacagcg tgatcttcac cgacaagatc atccgcagca acgccaccgt ggagcacctg 3900
cacccatgg gcgataacga tctggatggc agcttcaccc gcaccttcag cctgcgcgaa 3960
ggcggctact acagctccgt ggtggacagc cacatgcact tcaagagcgc catccacccc 4020
agcatcctgc agaacggggg ccccatgttc gccttccgcc gcgtggagga ggatcacagc 4080
aacaccgagc tgggcatcgt ggagtaccag cacgccttca gaccccgga tgcagatgcc 4140
ggtgaagaat aagagctcgc tgatcagcct cgactgtgcc ttctagttgc cagccatctg 4200
ttgtttgccc ctccccgtg ccttccttga ccctggaagg tgccactccc actgtcctt 4260
cctaataaaa tgaggaaatt gcatcgcatt gtctgagtag gtgtcattct attctgggg 4320
gtggggtggg gcaggacagc aagggggagg attgggaaga caatagcagg catgctggg 4380
atgcggggtg ctctatggaa gcttgaattc agctgacgtg cctcggaccg ctaggaaccc 4440
ctagtgatgg agttgccac tccctctctg cgcgctcgct cgctcactga ggccgggcga 4500
ccaaaggtcg cccgacgccc gggctttgcc cgggcggcct cagtgagcga gcgagcgcgc 4560
agctgcctgc agg                                                    4573

SEQ ID NO: 56          moltype = DNA  length = 642
FEATURE                Location/Qualifiers
misc_feature           1..642
                       note = Sequence encoding ranibizumab light chain
source                 1..642
                       mol_type = other DNA
                       organism = synthetic construct
SEQUENCE: 56
gacatccagc tgacacagag ccccagcagc ctgtctgcct ctgtgggaga cagagtgacc 60
atcacctgta gcgccagcca ggacatctcc aactacctga ctggtatca gcaaaagccc 120
ggcaaggccc ctaaggtgct gatctacttc acaagcagcc tgcactccgg cgtgcccagc 180
agattttctg gctctggcag cggcaccgac ttcaccctga ccatatctag cctgcagcct 240
gaggacttcg ccacctacta ctgccagcag tacagcaccg tgccttggac atttggccag 300
ggcacaaagg tggaaatcaa gcggactgtg gccgctccta gcgtgttcat ctttccacct 360
agcgacgagc agctgaagtc tggcacagcc tctgtcgtgt gcctgctgaa caacttctac 420
cccagagaag ccaaggtgca gtggaaagtg gacaatgccc tgcagagcgg caacagccaa 480
gagagcgtga cagagcagga ctccaaggat agcacctata gcctgagcag caccctgaca 540
ctgagcaagg ccgactacga gaagcacaaa gtgtacgcct gcgaagtgac ccaccagggc 600
ctttctagcc ctgtgaccaa gagcttcaac cggggcgaat gt                    642

SEQ ID NO: 57          moltype = DNA  length = 63
FEATURE                Location/Qualifiers
misc_feature           1..63
                       note = Linker sequence
source                 1..63
                       mol_type = other DNA
                       organism = synthetic construct
SEQUENCE: 57
```

```
ggctccggag agggcagagg aagtctgcta acatgcggtg acgtcgagga gaatcctggc   60
cca                                                                  63

SEQ ID NO: 58          moltype = DNA  length = 699
FEATURE                Location/Qualifiers
misc_feature           1..699
                       note = Sequence encoding Turbo GFP
source                 1..699
                       mol_type = other DNA
                       organism = synthetic construct
SEQUENCE: 58
atggagagcg acgagagcgg cctgcccgcc atggagatcg agtgccgcat caccggcacc   60
ctgaacggcg tggagttcga gctggtgggc ggcggagagg gcaccccga gcagggccgc   120
atgaccaaca agatgaagag caccaaaggc gccctgacct tcagccctca cctgctgagc   180
cacgtgatgg gctacggctt ctaccacttc ggcacctacc ccagcggcta cgagaacccc   240
ttcctgcacg ccatcaacaa cggcggctac accaacaccc gcatcgagaa gtacgaggac   300
ggcggcgtgc tgcacgtgag cttcagctac cgctacgagg ccggccgcgt gatcggcgac   360
ttcaaggtga tgggcaccgg cttccccgag gacagcgtga tcttcaccga caagatcatc   420
cgcagcaacg ccaccgtgga gcacctgcac cccatgggcg ataacgatct ggatggcagc   480
ttcacccgca ccttcagcct gcgcgacggc ggctactaca gctccgtggt ggacagccac   540
atgcacttca gagcgccat ccaccccagc atcctgcaga acgggggccc catgttcgcc   600
ttccgccgcg tggaggagga tcacagcaac accgagctgg gcatcgtgga gtaccagcac   660
gccttcaaga cccccggatg cagatgccggt gaagaataa                         699

SEQ ID NO: 59          moltype = AA  length = 232
FEATURE                Location/Qualifiers
REGION                 1..232
                       note = Turbo GFP
source                 1..232
                       mol_type = protein
                       organism = synthetic construct
SEQUENCE: 59
MESDESGLPA MEIECRITGT LNGVEFELVG GGEGTPEQGR MTNKMKSTKG ALTFSPYLLS   60
HVMGYGFYHF GTYPSGYENP FLHAINNGGY TNTRIEKYED GGVLHVSFSY RYEAGRVIGD   120
FKVMGTGFPE DSVIFTDKII RSNATVEHLH PMGDNDLDGS FTRTFSLRDG GYYSSVVDSH   180
MHFKSAIHPS ILQNGGPMFA FRRVEEDHSN TELGIVEYQH AFKTPDADAG EE           232

SEQ ID NO: 60          moltype = DNA  length = 3631
FEATURE                Location/Qualifiers
misc_feature           1..3631
                       note = pITR.CBA.Eylea
source                 1..3631
                       mol_type = other DNA
                       organism = synthetic construct
SEQUENCE: 60
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggccgcac gcgtgacatt gattattgac tagttattaa tagtaatcaa   180
ttacggggtc attagttcat agcccatata tggagttccg cgttacataa cttacggtaa   240
atggcccgcc tggctgaccg cccaacgacc cccgcccatt gacgtcaata atgacgtatg   300
ttcccatagt aacgccaata gggactttcc attgacgtca atgggtggac tatttacggt   360
aaactgccca cttggcagta catcaagtgt atcatatgcc aagtacgccc cctattgacg   420
tcaatgacgg taaatggccc gcctggcatt atgcccagta catgacctta tgggactttc   480
ctacttggca gtacatctac gtattagtca tcgctattac catgggtcga ggtgagcccc   540
acgttctgct tcactctccc catctccccc cctccccac ccccaatttt gtatttattt   600
attttttaat tattttgtgc agcgatgggg gcgggggggg gggggcgcg cgccaggcgg   660
ggcggggcgg ggcgaggggc ggggcggggc gaggcggaga ggtgcggcgg cagccaatca   720
gagcggcgcg ctccgaaagt tcctttttat ggcgaggcgg cggcggcggc ggccctaaa   780
aaagcgaagc gcgcggcggg cgggagtcgc tgcgttgcct tccgcccgtg ccccgctccg   840
cgccgcctcg cgccgcccgc cccggctctg actgaccgcg ttactcccac aggtgagcgg   900
gcgggacggc ccttctcctc cgggctgtaa ttagcgcttg gtttaatgac ggctcgtttc   960
ttttctgtgg ctgcgtgaaa gccttaaagg gctccgggag ggccctttgt gcgggggga  1020
gcggctcggg ggtgcgtgc gtgtgtgtgt gcgtgggggag cgccgcgtgc ggcccgcgct  1080
gcccggcggc tgtgagcgct gcgggcgcgg cgcgggctt tgtgcgctcc gcgtgtgcgc  1140
gaggggagcc cggccggggg cggtgccccg cggtggcggc gggctgcgag gggaacaaag  1200
gctgcgtgcg gggtgtgtgc gtgggggggt gagcaggggg tgtgggcgcg gcggtcgggc  1260
tgtaaccccc ccctgcaccc cctcccga gttgctgagc acggcccggc ttcgggtgcg  1320
gggctccgtg cggggcgtgg cgcggggctc gccgtgccgg gcggggggtg gcggcaggtg  1380
gggtgcgcgc ggcggtcgcg ccgcctcgg gccggggga ggggcgcggc  1440
ggccccccgga gcgccggcgg ctgtcgaggc gcggcgagcc gcagccattg ccttttatgg  1500
taatcgtgcg agagggcgca gggacttcct ttgtcccaaa tctgtgcgga ccgaaatct  1560
gggaggcgcc gccgcacccc ctctagcggg cgcggggcga agcggtgcgg cgccggcagg  1620
aagaaatgg gcgggaggg ccttcgtgcg tcgccgcgcc gccgtcccct tctccctctc  1680
ccggcgcgg gctgtccgcg ggggacggc tgccttcggg gggacggg caggggcga  1740
ttcggcttct ggcgtgtgac cggcggctct agagcctcctg ctaaccatgt tcatgccttc  1800
ttctttttcc tacagctcct gggcaacgtg ctggttattg tgaccggtgc caccatgtac  1860
cggatgcagc tgctgagctg tatcgccctg tctctggccc tggtcaccaa ttctagcgat  1920
accgcagac ccttcgtgga aatgtacagc gagatccccg agatcatcca catgaccgag  1980
ggcagagagc tggtcatccc ctgcagagtg acaagcccca acatcaccgt gactctgaag  2040
```

```
aagttccctc tggacacact gatccccgac ggcaagagaa tcatctggga cagccggaag    2100
ggcttcatca tcagcaacgc cacctacaaa gagatcggcc tgctgacctg tgaagccacc    2160
gtgaatggcc acctgtacaa gaccaactac ctgacacaca gacagaccaa caccatcatc    2220
gacgtggtgc tgagccctag ccacggcatt gaactgtctg tgggcgagaa gctggtgctg    2280
aactgtaccg ccagaaccga gctgaacgtg ggcatcgact tcaactggga gtaccccagc    2340
agcaagcacc agcacaagaa actggtcaac cgggacctga aaacccagag cggcagcgag    2400
atgaagaaat tcctgagcac cctgaccatc gacggcgtga ccagatctga ccagggcctg    2460
tacacatgtg ccgccagctc tggcctgatg accaagaaaa acagcacctt cgtgcgggtg    2520
cacgagaagg acaagaccca cacctgtcct ccatgtcctg ctccagaact gctcggcgga    2580
ccttccgtgt tcctgtttcc tccaaagcct aaggacaccc tgatgatcag cagaacccct    2640
gaagtgacct gcgtggtggt ggatgtgtcc cacgaggatc ccgaagtgaa gttcaattgg    2700
tacgtggacg gcgtggaagt gcacaacgcc aagaccaagc ctagagagga acagtacaat    2760
agcacctaca gagtggtgtc cgtgctgacc gtgctgcacc aggattggct gaacggcaaa    2820
gagtacaagt gcaaggtgtc caacaaggcc ctgcctgctc ctatcgagaa aaccatctcc    2880
aaggccaagg gccagcctag ggaacccag gtttacacac tgcctccaag cagggacgag    2940
ctgacaaaga accaggtgtc cctgacctgc ctggtcaagg gcttctaccc ttccgatatc    3000
gccgtggaat gggagagcaa tggccagcct gagaacaact acaagacaac ccctcctgtg    3060
ctggacacg acggctcatt cttcctgtac agcaagctga cagtggacaa gagcagatgg    3120
cagcagggca acgtgttcag ctgcagcgtg atgcacgagg ccctgcacaa ccactacacc    3180
cagaagtccc tgagcctgtc tcctggataa gagctcgctg atcagcctcg actgtgcctt    3240
ctagttgcca gccatctgtt gtttgccct ccccgtgcc ttccttgacc ctggaaggtg    3300
ccactcccac tgtcctttcc taataaaatg aggaaattgc atcgcattgt ctgagtaggt    3360
gtcattctat tctgggggggt ggggtgggc aggacagcaa gggggaggat tgggaagaca    3420
atagcaggca tgctggggat gcggtgggct ctatggaagc ttgaattcag ctgacgtgcc    3480
tcggaccgct aggaacccct agtgatggag ttggccactc cctctctgcg cgctcgctcg    3540
ctcactgagg ccgggcgacc aaaggtcgcc cgacgcccgg gctttgcccg ggcggcctca    3600
gtgagcgagc gagcgcgcag ctgcctgcag g                                    3631

SEQ ID NO: 61          moltype = DNA  length = 1296
FEATURE                Location/Qualifiers
misc_feature           1..1296
                       note = Sequence encoding aflibercept
source                 1..1296
                       mol_type = other DNA
                       organism = synthetic construct
SEQUENCE: 61
agcgataccg gcagaccctt cgtggaaatg tacagcgaga tccccgagat catccacatg      60
accgagggca gagagctggt catccctgc agagtgacaa gccccaacat caccgtgact     120
ctgaagaagt tccctctgga cacactgatc cccgacgca agagaatcat ctgggacagc     180
cggaagggct tcatcatcag caacgccacc tacaaagaga tcggcctgct gacctgtgaa     240
gccaccgtga atggccacct gtacaagacc aactacctga cacacagaca gaccaacacc     300
atcatcgacg tggtgctgag ccctagccac ggcattgaac tgtctgtggg cgagaagctg     360
gtgctgaact gtaccgccag aaccgagctg aacgtggca tcgacttcaa ctgggagtac     420
cccagcagca agcaccagca caagaaactg gtcaacgg acctgaaaac ccagagcggc     480
agcgagatga gaaattcct gagcaccctg accatcgacg gcgtgaccag atctgaccag     540
ggcctgtaca catgtgccgc cagctctggc ctgatgacca agaaaacag caccttcgtg     600
cgggtgcacg agaaggacaa gacccacacc tgtcctccat gtcctgctcc agaactgctc     660
ggcggacctt ccgtgttcct gtttcctcca aagcctaagg acaccctgat gatcagcaga     720
acccctgaag tgacctgcgt ggtggtggat gtgtcccacg aggatcccga agtgaagttc     780
aattggtacg tggacggcgt ggaagtgcac aacgccaaga ccaagcctag agaggaacag     840
tacaatagca cctacagagt ggtgtccgtg ctgaccgtgc tgcaccagga ttggctgaac     900
ggcaaagagt acaagtgcaa ggtgtccaac aaggccctgc ctgctcctat cgagaaaacc     960
atctccaagg ccagggcca gcctagggaa ccccaggttt acacactgcc tccaagcagg    1020
gacgagctga caaagaacca ggtgtccctg acctgcctgg tcaagggctt ctaccttcc    1080
gatatcgccg tggaatggga gagcaatggc cagcctgagaa acaactacaa gacaaccct    1140
cctgtgctgg acagcgacgg ctcattcttc ctgtacagca gctgacagt ggacaagagc    1200
agatggcagc agggcaacgt gttcagctgc agcgtgatgc acgaggccct gcacaaccac    1260
tacacccaga gtccctgag cctgtctcct ggataa                               1296
```

AAV-MEDIATED DELIVERY OF THERAPEUTIC ANTIBODIES TO THE INNER EAR

CROSS-REFERENCE TO RELATED APPLICATIONS

This application is a Continuation of U.S. patent application Ser. No. 16/955,715 filed on Jun. 18, 2020, which is a National Stage of International Application No. PCT/US2018/066512 filed Dec. 19, 2018, which claims priority to U.S. Provisional Patent Application Ser. No. 62/607,665 filed Dec. 19, 2017; the entire contents of which are herein incorporated by reference.

SEQUENCE LISTING

The instant application contains a Sequence Listing which has been submitted electronically in XML file format and is hereby incorporated by reference in its entirety. Said XML copy, created on Nov. 20, 2023, is named 2013615-0686_SL.xml and is 117,146 bytes in size.

TECHNICAL FIELD

The present disclosure relates generally to the use of nucleic acids to treat hearing loss in a human subject.

BACKGROUND OF THE INVENTION

Sensorinerual hearing loss is hearing loss that is caused by a malfunction of the cells (e.g., hair cells) in an inner ear of a mammal. Non-limiting causes of sensorineural hearing loss include exposure to loud noise, head trauma, viral infection, autoimmune inner ear disease, genetic hearing loss, aging, malformations in the inner ear, Meniere's disease, otosclerosis, and tumors.

SUMMARY

The present invention relates to methods that include introducing into an inner ear of a mammal (e.g., a human) a therapeutically effective amount of any adeno-associated virus (AAV) vector that includes a nucleotide sequence encoding: (a) a polypeptide including an antibody heavy chain variable domain operably linked to a signal peptide and a polypeptide including an antibody light chain variable domain operably linked to a signal peptide; or (b) a polypeptide including an antigen-binding antibody fragment operably linked to a signal peptide.

Provided herein are methods for increasing the level of an antibody or an antigen-binding antibody fragment in an inner ear of a mammal in need thereof that include: introducing into the inner ear of the mammal a therapeutically effective amount of an AAV vector that includes a nucleotide sequence encoding (a) a polypeptide including an antibody heavy chain variable domain operably linked to a signal peptide and a polypeptide including an antibody light chain variable domain operably linked to a signal peptide; or (b) a polypeptide including an antigen-binding antibody fragment linked to a signal peptide; wherein the introducing results in an increase in the level of the antibody or the antigen-binding antibody fragment in the inner ear of the mammal.

In some embodiments, the antibody or the antigen-binding antibody fragment binds specifically to vascular endothelial growth factor (VEGF). In some embodiments, the antibody or antigen-binding antibody fragment decreases VEGF activity. In some embodiments of any of the methods described herein, the AAV vector further includes one or both of a promoter and a Kozak sequence that are operably linked to the sequence encoding the antibody or the antigen-binding antibody fragment.

In some embodiments, the AAV vector includes a promoter selected from the group consisting of: an inducible promoter, a constitutive promoter, and a tissue-specific promoter. In some embodiments of any of the methods described herein, the AAV vector further includes a polyadenylation signal sequence.

In some embodiments of any of the methods described herein, the mammal is a human. In some embodiments of any of the methods described herein, the mammal has been identified as having an inner ear disorder. In some embodiments of any of the methods described herein, the mammal has been diagnosed as having an inner ear disorder.

In some embodiments of any of the methods described herein, the AAV vector includes a nucleic acid sequence encoding a polypeptide including an antibody heavy chain variable domain operably linked to a signal peptide and a polypeptide including an antibody light chain variable domain operably linked to a signal peptide.

In some embodiments of any of the methods described herein, the AAV vector includes a nucleic acid sequence encoding a polypeptide including an antigen-binding antibody fragment operably linked to a signal.

Also provided herein are methods for treating an inner ear disorder in a mammal in need thereof that include: introducing into the inner ear of the mammal a therapeutically effective amount of an AAV vector that includes a nucleotide sequence encoding: (a) a polypeptide including an antibody heavy chain variable domain operably linked to a signal peptide and a polypeptide including an antibody light chain variable domain operably linked to a signal peptide; or (b) a polypeptide including an antigen-binding antibody fragment linked to a signal peptide; wherein the introducing results in the treatment of the inner ear disorder in the mammal.

In some embodiments of any of the methods described herein, the AAV vector further includes one or both of a promoter and a Kozak sequence that are operably linked to the sequence encoding the antibody or the antigen-binding antibody fragment.

In some embodiments, the AAV vector includes a promoter selected from the group consisting of: an inducible promoter, a constitutive promoter, and a tissue-specific promoter.

In some embodiments of any of the methods described herein, the AAV vector further includes a polyadenylation signal sequence.

In some embodiments of any of the methods described herein, the mammal is a human. In some embodiments of any of the methods described herein, the mammal has been identified as having an inner ear disorder. In some embodiments of any of the methods described herein, the mammal has been diagnosed as having an inner ear disorder.

In some embodiments of any of the methods described herein, the AAV vector includes a nucleic acid sequence encoding a polypeptide including an antibody heavy chain variable domain operably linked to a signal peptide and a polypeptide including an antibody light chain variable domain operably linked to a signal peptide.

In some embodiments of any of the methods described herein, the AAV vector includes a nucleic acid sequence encoding a polypeptide including an antigen-binding antibody fragment operably linked to a signal.

Also provided herein are methods of reducing VEGF activity in an inner ear of a mammal in need thereof that include: introducing into the inner ear of the mammal a therapeutically effective amount of an AAV vector that includes a nucleotide sequence encoding (a) a polypeptide including an antibody heavy chain variable domain operably linked to a signal peptide and a polypeptide including an antibody light chain variable domain operably linked to a signal peptide; or (b) a polypeptide including an antigen-binding antibody fragment linked to a signal peptide; wherein the polypeptide of (a) encodes an antibody that binds specifically to VEGF and reduces VEGF activity, the polypeptide of (b) encodes an antigen-binding antibody fragment that binds specifically to VEGF and reduces VEGF activity; wherein the introducing results in a reduction in VEGF activity in the inner ear of the mammal.

In some embodiments of any of the methods described herein, the AAV vector further includes one or both of a promoter and a Kozak sequence that are operably linked to the sequence encoding the antibody or the antigen-binding antibody fragment.

In some embodiments, the AAV vector includes a promoter selected from the group consisting of: an inducible promoter, a constitutive promoter, and a tissue-specific promoter.

In some embodiments of any of the methods described herein, the AAV vector further includes a polyadenylation signal sequence. In some embodiments of any of the methods described herein, the mammal is a human.

In some embodiments of any of the methods described herein, the mammal has been identified or diagnosed as having an acoustic neuroma. In some embodiments, the mammal has been identified or diagnosed as having a vestibular schwannoma. In some embodiments of any of the methods described herein, the mammal has been identified or diagnosed as having a neurofibromatosis type 2.

In some embodiments of any of the methods described herein, the AAV vector includes a nucleic acid sequence encoding a polypeptide including an antibody heavy chain variable domain operably linked to a signal peptide and a polypeptide including an antibody light chain variable domain operably linked to a signal peptide.

In some embodiments of any of the methods described herein, the AAV vector includes a nucleic acid sequence encoding a polypeptide including an antigen-binding antibody fragment operably linked to a signal peptide.

Also provided herein are methods of treating acoustic neuroma, vestibular schwannoma, or neurofibromatosis type 2 in an inner ear of a mammal that include: introducing into the inner ear of the mammal a therapeutically effective amount of an AAV vector that includes a nucleotide sequence encoding (a) a polypeptide including an antibody heavy chain variable domain operably linked to a signal peptide and a polypeptide including an antibody light chain variable domain operably linked to a signal peptide; or (b) a polypeptide including an antigen-binding antibody fragment linked to a signal peptide; wherein the polypeptide of (a) encodes an antibody that binds specifically to VEGF and reduces VEGF activity, the polypeptide of (b) encodes an antigen-binding antibody fragment that binds specifically to VEGF and reduces VEGF activity; wherein the introducing results in treatment of acoustic neuroma, vestibular schwannoma, or neurofibromatosis type II, respectively, in the inner ear of the mammal.

In some embodiments of any of the methods described herein, the AAV vector further includes one or both of a promoter and a Kozak sequence that are operably linked to the sequence encoding the antibody or the antigen-binding antibody fragment.

In some embodiments of any of the methods described herein, the AAV vector includes a promoter selected from the group consisting of: an inducible promoter, a constitutive promoter, and a tissue-specific promoter.

In some embodiments of any of the methods described herein, the AAV vector further includes a polyadenylation signal sequence.

In some embodiments of any of the methods described herein, the mammal is a human. In some embodiments of any of the methods described herein, the mammal has been identified or diagnosed as having an acoustic neuroma. In some embodiments of any of the methods described herein, the mammal has been identified or diagnosed as having a vestibular schwannoma. In some embodiments of any of the methods described herein, the mammal has been identified or diagnosed as having neurofibromatosis type 2.

In some embodiments of any of the methods described herein, the AAV vector includes a nucleic acid sequence encoding a polypeptide including an antibody heavy chain variable domain operably linked to a signal peptide and a polypeptide including an antibody light chain variable domain operably linked to a signal peptide.

In some embodiments of any of the methods described herein, the AAV vector includes a nucleic acid sequence encoding a polypeptide including an antigen-binding antibody fragment operably linked to a signal peptide.

In some embodiments of any of the methods described herein, the antibody includes a Fc region that includes one or more amino acid substitutions that decreases the half-life of the antibody in a mammal as compared to a control antibody; or the antigen-binding antibody fragment thereof has a decreased in vivo half-life as compared to a control antigen-binding antibody fragment.

Also provided herein are methods that include introducing into an inner ear of a mammal a therapeutically effective amount of an adeno-associated virus (AAV) vector that includes a nucleotide sequence encoding a soluble vascular endothelial growth factor (VEGF) receptor operably linked to a signal peptide.

Also provided herein are methods for increasing the level of a soluble vascular endothelial growth factor (VEGF) receptor in an inner ear of a mammal in need thereof that include: introducing into the inner ear of the mammal a therapeutically effective amount of an AAV vector that includes a nucleotide sequence encoding a soluble VEGF receptor operably linked to a signal peptide; where the introducing results in an increase in the level of the soluble VEGF receptor in the inner ear of the mammal.

In some embodiments of any of the methods described herein, the soluble VEGF receptor includes a portion of an extracellular region of VEGF receptor-1 (VEGFR-1). In some embodiments of any of the methods described herein, the portion of the extracellular region of VEGFR-1 includes a contiguous sequence from wildtype human VEGFR-1. In some embodiments of any of the methods described herein, the portion of the extracellular region of VEGFR-1 includes one or more immunoglobulin-like domains in the extracellular region from wildtype human VEGFR-1. In some embodiments of any of the methods described herein, the portion of the extracellular region of VEGFR-1 includes a sequence that is at least 90% identical to a contiguous sequence from wildtype human VEGFR-1.

In some embodiments of any of the methods described herein, the soluble VEGF receptor includes a portion of an extracellular region of VEGF receptor-2 (VEGFR-2). In some embodiments of any of the methods described herein, the portion of the extracellular region of VEGFR-2 includes a contiguous sequence from wildtype human VEGFR-2. In some embodiments of any of the methods described herein, the portion of the extracellular region of VEGFR-2 includes one or more immunoglobulin-like domains in the extracellular region from wildtype human VEGFR-2. In some embodiments of any of the methods described herein, the portion of the extracellular region of VEGFR-2 includes a sequence that is at least 90% identical to a contiguous sequence from wildtype human VEGFR-2.

In some embodiments of any of the methods described herein, the soluble VEGF receptor includes a portion of an extracellular region of VEGFR-1 and a portion of an extracellular region of VEGFR-2. In some embodiments of any of the methods described herein, the portion of the extracellular region of VEGFR-1 includes one or more immunoglobulin-like domains in the extracellular region from wildtype human VEGFR-1; and the portion of the extracellular region of VEGFR-2 includes one or more immunoglobulin-like domains in the extracellular region from wildtype human VEGFR-2. In some embodiments of any of the methods described herein, the soluble VEGF receptor is aflibercept.

In some embodiments of any of the methods described herein, the soluble VEGF receptor includes a portion of an extracellular region of VEGF receptor-3 (VEGFR-3). In some embodiments of any of the methods described herein, the portion of the extracellular region of VEGFR-3 includes a contiguous sequence from wildtype human VEGFR-3. In some embodiments of any of the methods described herein, the portion of the extracellular region of VEGFR-3 includes one or more immunoglobulin-like domains in the extracellular region from wildtype human VEGFR-3. In some embodiments of any of the methods described herein, the portion of the extracellular region of VEGFR-3 includes a sequence that is at least 90% identical to a contiguous sequence from wildtype human VEGFR-3. In some embodiments of any of the methods described herein, the soluble VEGF receptor comprises a Fc domain. In some embodiments of any of the methods described herein, the Fc domain is an IgG1 Fc domain. In some embodiments of any of the methods described herein, the IgG1 Fc domain is a human wildtype IgG1 Fc domain.

In some embodiments of any of the methods described herein, the soluble VEGF receptor decreases the ability of a VEGF to bind to one or more of VEGFR-1, VEGFR-2, and VEGFR-3.

In some embodiments of any of the methods described herein, the AAV vector further includes one or both of a promoter and a Kozak sequence that are operably linked to the sequence encoding the soluble VEGF receptor. In some embodiments of any of the methods described herein, the AAV vector includes a promoter selected from the group of: an inducible promoter, a constitutive promoter, and a tissue-specific promoter. In some embodiments of any of the methods described herein, the AAV vector further includes a polyadenylation signal sequence.

In some embodiments of any of the methods described herein, the mammal is a human. In some embodiments of any of the methods described herein, the mammal has been identified as having an inner ear disorder. In some embodiments of any of the methods described herein, the mammal has been diagnosed as having an inner ear disorder.

Also provided herein are methods for treating an inner ear disorder in a mammal in need thereof that include: introducing into the inner ear of the mammal a therapeutically effective amount of an AAV vector that includes a nucleotide sequence encoding a soluble vascular endothelial growth factor (VEGF) receptor operably linked to a signal peptide; where the introducing results in the treatment of the inner ear disorder in the mammal.

In some embodiments of any of the methods described herein, the AAV vector further includes one or both of a promoter and a Kozak sequence that are operably linked to the sequence encoding the soluble VEGF receptor. In some embodiments of any of the methods described herein, the AAV vector includes a promoter selected from the group of: an inducible promoter, a constitutive promoter, and a tissue-specific promoter. In some embodiments of any of the methods described herein, the AAV vector further includes a polyadenylation signal sequence.

In some embodiments of any of the methods described herein, the mammal is a human. In some embodiments of any of the methods described herein, the mammal has been identified as having an inner ear disorder. In some embodiments of any of the methods described herein, the mammal has been diagnosed as having an inner ear disorder.

Also provided herein are methods of reducing a VEGF activity in an inner ear of a mammal in need thereof that include: introducing into the inner ear of the mammal a therapeutically effective amount of an AAV vector that includes a nucleotide sequence encoding a soluble vascular endothelial growth factor (VEGF) receptor operably linked to a signal peptide; where the introducing results in a reduction in the VEGF activity in the inner ear of the mammal.

In some embodiments of any of the methods described herein, the AAV vector further includes one or both of a promoter and a Kozak sequence that are operably linked to the sequence encoding the soluble VEGF receptor. In some embodiments of any of the methods described herein, the AAV vector includes a promoter selected from the group of: an inducible promoter, a constitutive promoter, and a tissue-specific promoter. In some embodiments of any of the methods described herein, the AAV vector further includes a polyadenylation signal sequence.

In some embodiments of any of the methods described herein, the mammal is a human. In some embodiments of any of the methods described herein, the mammal has been identified or diagnosed as having an acoustic neuroma. In some embodiments of any of the methods described herein, the mammal has been identified or diagnosed as having a vestibular schwannoma. In some embodiments of any of the methods described herein, the mammal has been identified or diagnosed as having a neurofibromatosis type 2.

Also provided herein are methods of treating acoustic neuroma, vestibular schwannoma, or neurofibromatosis type 2 in an inner ear of a mammal that include: introducing into the inner ear of the mammal a therapeutically effective amount of an AAV vector that includes a nucleotide sequence encoding a nucleotide sequence encoding a soluble vascular endothelial growth factor (VEGF) receptor operably linked to a signal peptide; where the introducing results in treatment of acoustic neuroma, vestibular schwannoma, or neurofibromatosis type II, respectively, in the inner ear of the mammal.

In some embodiments of any of the methods described herein, the AAV vector further includes one or both of a promoter and a Kozak sequence that are operably linked to the sequence encoding the soluble VEGF receptor. In some embodiments of any of the methods described herein, the AAV vector includes a promoter selected from the group of: an inducible promoter, a constitutive promoter, and a tissue-specific promoter. In some embodiments of any of the methods described herein, the AAV vector further includes a polyadenylation signal sequence.

In some embodiments of any of the methods described herein, the mammal is a human. In some embodiments of any of the methods described herein, the mammal has been identified or diagnosed as having an acoustic neuroma. In some embodiments of any of the methods described herein, the mammal has been identified or diagnosed as having a vestibular schwannoma. In some embodiments of any of the methods described herein, the mammal has been identified or diagnosed as having neurofibromatosis type 2.

In some embodiments of any of the methods described herein, the soluble VEGF receptor includes a portion of an extracellular region of VEGF receptor-1 (VEGFR-1). In some embodiments of any of the methods described herein, the portion of the extracellular region of VEGFR-1 includes a contiguous sequence from wildtype human VEGFR-1. In some embodiments of any of the methods described herein, the portion of the extracellular region of VEGFR-1 includes one or more immunoglobulin-like domains in the extracellular region from wildtype human VEGFR-1. In some embodiments of any of the methods described herein, the portion of the extracellular region of VEGFR-1 includes a sequence that is at least 90% identical to a contiguous sequence from wildtype human VEGFR-1.

In some embodiments of any of the methods described herein, the soluble VEGF receptor includes a portion of an extracellular region of VEGF receptor-2 (VEGFR-2). In some embodiments of any of the methods described herein, the portion of the extracellular region of VEGFR-2 includes a contiguous sequence from wildtype human VEGFR-2. In some embodiments of any of the methods described herein, the portion of the extracellular region of VEGFR-2 includes one or more immunoglobulin-like domains in the extracellular region from wildtype human VEGFR-2. In some embodiments of any of the methods described herein, the portion of the extracellular region of VEGFR-2 includes a sequence that is at least 90% identical to a contiguous sequence from wildtype human VEGFR-2.

In some embodiments of any of the methods described herein, the soluble VEGF receptor includes a portion of an extracellular region of VEGFR-1 and a portion of an extracellular region of VEGFR-2. In some embodiments of any of the methods described herein, the portion of the extracellular region of VEGFR-1 includes one or more immunoglobulin-like domains in the extracellular region from wildtype human VEGFR-1; and the portion of the extracellular region of VEGFR-2 includes one or more immunoglobulin-like domains in the extracellular region from wildtype human VEGFR-2. In some embodiments of any of the methods described herein, the soluble VEGF receptor is aflibercept.

In some embodiments of any of the methods described herein, the soluble VEGF receptor includes a portion of an extracellular region of VEGF receptor-3 (VEGFR-3). In some embodiments of any of the methods described herein, the portion of the extracellular region of VEGFR-3 includes a contiguous sequence from wildtype human VEGFR-3. In some embodiments of any of the methods described herein, the portion of the extracellular region of VEGFR-3 includes one or more immunoglobulin-like domains in the extracellular region from wildtype human VEGFR-3. In some embodiments of any of the methods described herein, the portion of the extracellular region of VEGFR-3 includes a sequence that is at least 90% identical to a contiguous sequence from wildtype human VEGFR-3.

In some embodiments of any of the methods described herein, the soluble VEGF receptor comprises a Fc domain. In some embodiments of any of the methods described herein, the Fc domain is an IgG1 Fc domain. In some embodiments of any of the methods described herein, the IgG1 Fc domain is a human wildtype IgG1 Fc domain.

In some embodiments of any of the methods described herein, the soluble VEGF receptor decreases the ability of a VEGF to bind to one or more of VEGFR-1, VEGFR-2, and VEGFR-3. In some embodiments of any of the methods described herein, the AAV vector further includes a secretion sequence.

Unless otherwise specified, a "nucleotide sequence encoding an amino acid sequence" includes all nucleotide sequences that are degenerate versions of each other and thus encode the same amino acid sequence.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "transfected," "transformed," or "transduced" refers to a process by which exogenous nucleic acid is transferred or introduced into a cell. A "transfected," "transformed," or "transduced" mammalian cell is one that has been transfected, transformed, or transduced with exogenous nucleic acid.

The term "expression" refers to the transcription and/or translation of a particular nucleotide sequence encoding a protein.

The term "transient expression" refers to the expression of a non-integrated coding sequence for a short period of time (e.g., hours or days). The coding sequence that is transiently expressed in a cell (e.g., a mammalian cell) is lost upon multiple rounds of cell division.

The term "subject" is intended to include any mammal. In some embodiments, the subject is a rodent (e.g., a rat or mouse), a rabbit, a sheep, a goat, a pig, a dog, a cat, a non-human primate, or a human. In some embodiments, the subject has or is at risk of developing non-syndromic deafness. In some embodiments, the subject has been previously identified as having an inner ear disorder. In some embodiments, the subject has previously been diagnosed as having an inner ear disorder. In some embodiments, the subject has been identified as having drug-induced hearing loss. In some embodiments, the subject is an infant (e.g., a human infant).

A treatment is "therapeutically effective" when it results in a reduction in one or more of the number, severity, and frequency of one or more symptoms of a disease (e.g., non-symptomatic sensorineural hearing loss) in a subject (e.g., a human).

The term "nucleic acid" or "polynucleotide" refers to deoxyribonucleic acid (DNA) or ribonucleic acid (RNA), or a combination thereof, in either single- or double-stranded form. Unless specifically limited, the term encompasses nucleic acids containing known analogues of natural nucleotides that have similar binding properties as the reference nucleotides. Unless otherwise indicated, a particular nucleic acid sequence also implicitly encompasses complementary sequences as well as the sequence explicitly indicated. In some embodiments of any of the nucleic acids described herein, the nucleic acid is DNA. In some embodiments of any of the nucleic acids described herein, the nucleic acid is RNA.

The term "signal peptide" refers to a sequence present on the N-terminus of a nascent secreted protein but is absent in the naturally-occurring mature protein. A "signal peptide" is cleaved by a protease (e.g., a signal peptidase) after the signal peptide is translated. Signal peptides are known in the art. Non-limiting examples of signal peptides include: MEFFKKTALAALVMGFSGAALA (SEQ ID NO: 9) and MKYLLPTAAAGLLLLAAQPAMA (SEQ ID NO: 10).

The term "inner ear disorder" refers to a disorder caused by malfunction of the cells (e.g., hair cells, supporting cells, spiral ganglion neurons, macrophages, or schwann cells) in or around the inner ear of a mammal. Non-limiting examples of inner ear disorders include, e.g., sensorineural hearing loss (SNHL), noise-induced hearing loss, drug-induced hearing loss, age-related hearing loss, acoustic neuroma, neurofibromatosis type 2, auditory neuropathy, noise-induced cochlear synaptopathy without hair cell loss, age-related cochlear synaptopathy, acquired sensorineural hearing loss, and vestibular schwannoma. See, e.g., Kujawa et al., *Hear Res* 330(0 0): 191-199, 2015; and Suzuki et al., *Scientific Reports* 6: 24907. Non-limiting examples of inner ear disorders are described herein and additional examples of inner ear disorders are known in the art.

The term "antibody" means a complex of two or more single polypeptide chains that interact to form at least one antigen-binding domain. Non-limiting examples of an antibody include monoclonal antibodies (for example, full length or intact monoclonal antibodies), polyclonal antibodies, multivalent antibodies, multispecific antibodies (e.g., bispecific, trispecific, etc. antibodies so long as they exhibit the desired biological activity). An antibody can be human, humanized, and/or affinity-matured.

The term "antigen-binding antibody fragment" is a single polypeptide that includes all the amino acids that make up at least one antigen-binding domain (e.g., an scFv).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al, Proc. Natl. Acad. Sci. USA 81:6851-6855 (1984)).

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigens. In some examples, an antigen-binding domain can bind to an antigen or epitope with specificity and affinity similar to that of naturally-occurring antibodies. In some embodiments, an antigen-binding domain can include an alternative scaffold. Non-limiting examples of antigen-binding domains are described herein. Additional examples of antigen-binding domains are known in the art. In some examples, an antigen-binding domain can bind to a single antigen.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity between an antigen-binding domain and its corresponding antigen or epitope are known in the art.

The phrase "half-life" refers to the half-life of an antibody, an antigen-binding antibody fragment thereof, or a soluble VEGF receptor in circulation (e.g., blood) of a mammal (e.g., any of the mammals described herein) and is represented by the time required for 50% of an antibody, an antigen-binding antibody fragment thereof, or soluble VEGF receptor to be cleared from the circulation. In some embodiments, an alteration in half-life (e.g., a decrease in half-life of an antibody, an antigen-binding antibody fragment thereof, or soluble VEGF receptor) is determined by comparing the half-life of an antibody, an antigen-binding antibody fragment, or a soluble VEGF receptor in a subject to the half-life of a control antibody, control antigen-binding antibody fragment, or control soluble VEGF receptor in a similar mammal.

In some embodiments, the half-life of an antibody, antigen-binding antibody fragment thereof, or soluble VEGF receptor in a mammal is determined by measuring the level of the antibody, antigen-binding antibody fragment thereof, or soluble VEGF receptor in samples obtained from a subject (e.g., a blood sample) at different time points following systemic administration (e.g., intravenous) administration of any of the AAV vectors described herein. In some embodiments, the level of the antibody, antigen-binding antibody fragment thereof, or soluble VEGF receptor present in samples obtained from a mammal is determined using enzyme-linked immunosorbent assay (ELISA) or another assay known to the art, and the determined level of the antibody, antigen-binding antibody fragment thereof, or soluble VEGF receptor present in the samples is plotted as a function of time using a software program (e.g., GraphPad Prism).

The term "VEGF activity" refers to one or more known activities of a VEGF protein. For example, one activity of a VEGF protein is the ability to bind to one or more VEGF receptors. In another example, one activity of a VEGF protein is the ability of a VEGF to trigger downstream signal transduction pathway(s) in a mammalian cell expressing a VEGF receptor. Methods for detecting one or more activities of VEGF are known in the art.

The term "soluble VEGF receptor" refers to a polypeptide that includes a portion of an extracellular region of one or more mammalian VEGF receptor(s) (e.g., VEGFR-1, VEGFR-2, and VEGFR-3) operably linked to a signal peptide, where the soluble VEGF receptor is capable of specifically binding to one or more mammalian VEGF proteins (e.g., one or more of VEGF-A, VEGF-B, VEGF-C, and VEGF-D). In some examples, a soluble VEGF receptor includes a portion of an extracellular region of VEGFR-1 (e.g., a contiguous sequence from wildtype human VEGFR-1 (e.g., one or more immunoglobulin-like domains in the extracellular region from wildtype human VEGFR-1) or a sequence that is at least 90% identical to a contiguous sequence from wildtype human VEGFR-1). In some examples, a soluble VEGF receptor includes a portion of an extracellular region of VEGFR-2 (e.g., a contiguous sequence from wildtype human VEGFR-2 (e.g., one or more immunoglobulin-like domains in the extracellular region from wildtype human VEGFR-2) or a sequence that is at least 90% identical to a contiguous sequence from wildtype human VEGFR-2). In some examples, a soluble VEGF receptor includes a portion of an extracellular region of VEGFR-1 and a portion of an extracellular region of VEGFR-2 (e.g., one or more immunoglobulin-like domains in the extracellular region from wildtype human VEGFR-1 and one or more immunoglobulin-like domains in the extracellular region from wildtype human VEGFR-2) (e.g., aflibercept). In some examples, a soluble VEGF receptor includes a portion of an extracellular region of VEGFR-3 (e.g., a contiguous sequence from wildtype human VEGFR-3 (e.g., one or more immunoglobulin-like domains in the extracellular region from wildtype human VEGFR-3) or a sequence that is at least 90% identical to a contiguous sequence from wildtype human VEGFR-3).

In some examples, a soluble VEGF receptor can further include a stabilizing domain (e.g., a Fc domain, such as an IgG1 Fc domain (e.g., a human wildtype IgG1 Fc domain). In some examples, the soluble VEGF receptor decreases the ability of a VEGF to bind to one or more (e.g., two or three) of VEGFR-1, VEGFR-2, and VEGFR-3. Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

BRIEF DESCRIPTION OF DRAWINGS

FIG. 4C is a table showing the equilibrium dissociation constant ($K_D$) determined from the data shown in FIGS. 3A, 3B, 4A, and 4B (going from the top to the bottom of the table).

DETAILED DESCRIPTION

Figure 1A:
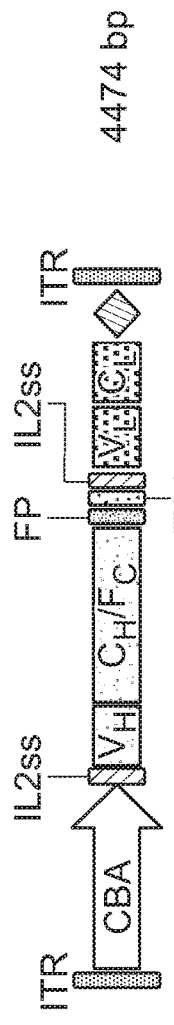
FIG. 1A is an exemplary AAV vector of 4474 bp that includes a sequence encoding bevacizumab (Avastin®).

Provided herein are methods that include introducing into an inner ear of a mammal a therapeutically effective amount of an adeno-associated virus (AAV) vector that includes a nucleotide sequence encoding: (a) a polypeptide including an antibody heavy chain variable domain operably linked to a signal peptide and a polypeptide including an antibody light chain variable domain operably linked to a signal peptide; or (b) a polypeptide including an antigen-binding antibody fragment (e.g., a Fab or a scFv)operably linked to a signal peptide.

Also provided herein are methods for increasing the level of an antibody or an antigen-binding antibody fragment in an inner ear of a mammal in need thereof, that include: introducing into the inner ear of the mammal a therapeutically effective amount of an AAV vector that includes a nucleotide sequence encoding: (a) a polypeptide including an antibody heavy chain variable domain operably linked to a signal peptide and a polypeptide including an antibody light chain variable domain operably linked to a signal peptide; or (b) a polypeptide including an antigen-binding antibody fragment (e.g., a Fab or a scFv) operably linked to a signal peptide; wherein the introducing results in an increase in the level of the antibody or the antigen-binding antibody fragment in the inner ear of the mammal.

Also provided are methods for treating an inner ear disorder in a mammal in need thereof that include introducing into the inner ear of the mammal a therapeutically effective amount of an AAV vector that includes a nucleotide sequence encoding: (a) a polypeptide including an antibody heavy chain variable domain operably linked to a signal peptide and a polypeptide comprising an antibody light chain variable domain operably linked to a signal peptide; or (b) a polypeptide comprising an antigen-binding antibody fragment linked to a signal peptide; where the introducing results in the treatment of the inner ear disorder in the mammal.

Also provided herein are methods of reducing VEGF activity in an inner ear of a mammal in need thereof that include: introducing into the inner ear of the mammal a therapeutically effective amount of an AAV vector that includes a nucleotide sequence encoding (a) a polypeptide including an antibody heavy chain variable domain operably linked to a signal peptide and a polypeptide including an antibody light chain variable domain operably linked to a signal peptide; or (b) a polypeptide including an antigen-binding antibody fragment (e.g., a Fab or a scFv) operably linked to a signal peptide; wherein the polypeptide of (a) encodes an antibody that binds specifically to VEGF and reduces VEGF activity, the polypeptide of (b) encodes an antigen-binding antibody fragment that binds specifically to VEGF and reduces VEGF activity; and wherein the introducing results in a reduction in VEGF activity in the inner ear of the mammal.

Also provided herein are methods of treating acoustic neuroma, vestibular schwannoma, or neurofibromatosis type II in an inner ear of a mammal that include: introducing into the inner ear of the mammal a therapeutically effective amount of an AAV vector that includes a nucleotide sequence encoding (a) a polypeptide including an antibody heavy chain variable domain operably linked to a signal peptide and a polypeptide including an antibody light chain variable domain operably linked to a signal peptide; or (b) a polypeptide including an antigen-binding antibody fragment (e.g., a Fab or a scFv) operably linked to a signal peptide; wherein the polypeptide of (a) encodes an antibody that binds specifically to VEGF and reduces VEGF activity, the polypeptide of (b) encodes an antigen-binding antibody fragment that binds specifically to VEGF and reduces VEGF activity; and wherein the introducing results in treatment of acoustic neuroma or vestibular schwannoma in the inner ear of the mammal.

Also provided herein are methods that include introducing into an inner ear of a mammal a therapeutically effective amount of an adeno-associated virus (AAV) vector that include a nucleotide sequence encoding a soluble vascular endothelial growth factor (VEGF) receptor operably linked to a signal peptide.

Also provided herein are methods for increasing the level of a soluble vascular endothelial growth factor (VEGF) receptor in an inner ear of a mammal in need thereof that include introducing into the inner ear of the mammal a therapeutically effective amount of an AAV vector that includes a nucleotide sequence encoding a soluble VEGF receptor operably linked to a signal peptide; where the introducing results in an increase in the level of the soluble VEGF receptor in the inner ear of the mammal.

Also provided herein are methods for treating an inner ear disorder in a mammal in need thereof that include introducing into the inner ear of the mammal a therapeutically effective amount of an AAV vector that includes a nucleotide sequence encoding a soluble vascular endothelial growth factor (VEGF) receptor operably linked to a signal peptide; where the introducing results in the treatment of the inner ear disorder in the mammal.

Also provided herein are methods of reducing a VEGF activity in an inner ear of a mammal in need thereof that include introducing into the inner ear of the mammal a therapeutically effective amount of an AAV vector that includes a nucleotide sequence encoding a soluble vascular endothelial growth factor (VEGF) receptor operably linked to a signal peptide; where the introducing results in a reduction in the VEGF activity in the inner ear of the mammal.

Also provided herein are methods of treating acoustic neuroma, vestibular schwannoma, or neurofibromatosis type 2 in an inner ear of a mammal that include introducing into the inner ear of the mammal a therapeutically effective amount of an AAV vector that includes a nucleotide sequence encoding a nucleotide sequence encoding a soluble vascular endothelial growth factor (VEGF) receptor operably linked to a signal peptide; where the introducing results in treatment of acoustic neuroma, vestibular schwannoma, or neurofibromatosis type II, respectively, in the inner ear of the mammal.

Also provided are kits that include any of the AAV vectors described herein.

Additional non-limiting aspects of the compositions, kits, and methods are described herein and can be used in any combination without limitation.

Antibodies and Antigen-Binding Antibody Fragments

In some embodiments, the antibody can be a humanized antibody, a chimeric antibody, or a multivalent antibody. In some embodiments, an antibody or an antigen-binding antibody fragment can be a scFv-Fc, a $V_HH$ domain, a $V_{NAR}$ domain, a $(scFv)_2$, a minibody, or a BiTE. In some embodiments, an antibody or an antigen-binding antibody fragment can be a DVD-Ig, and a dual-affinity re-targeting antibody (DART), a triomab, kih IgG with a common LC, a crossmab, an ortho-Fab IgG, a 2-in-1-IgG, IgG-ScFv, scFv$_2$-Fc, a bi-nanobody, tanden antibody, a DART-Fc, a scFv-HAS-scFv, DNL-Fab3, DAF (two-in-one or four-in-one), Duta-Mab, DT-IgG, knobs-in-holes common LC, knobs-in-holes assembly, charge pair antibody, Fab-arm exchange antibody, SEEDbody, Triomab, LUZ-Y, Fcab, kλ-body, orthogonal Fab, DVD-IgG, IgG(H)-scFv, scFv-(H)IgG, IgG(L)-scFv, scFv-(L)-IgG, IgG (L,H)-Fc, IgG(H)-V, V(H)-IgG, IgG(L)-V, V(L)-IgG, KIH IgG-scFab, 2scFv-IgG, IgG-2scFv, scFv4-Ig, Zybody, DVI-IgG, nanobody, nanobody-HSA, a diabody, a TandAb, scDiabody, scDiabody-CH3, Diabody-CH3, Triple Body, miniantibody, minibody, TriBi minibody, scFv-CH3 KIH, Fab-scFv, scFv-CH-CL-scFv, F(ab')$_2$-scFV$_2$, scFv-KIH, Fab-scFv-Fc, tetravalent HCAb, scDiabody-Fc, diabody-Fc, tandem scFv-Fc, intrabody, dock and lock bispecific antibody, ImmTAC, HSAbody, scDiabody-HAS, tandem scFv, IgG-IgG, Cov-X-Body, and scFv1-PEG-scFv2.

Additional examples of an antibody or an antigen-binding antibody fragment include an Fv fragment, a Fab fragment, a F(ab')$_2$ fragment, and a Fab' fragment. Additional examples of an antibody or an antigen-binding antibody fragment include an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

Any of the antibodies or antigen-binding antibody fragments described herein can bind specifically to VEGF.

A $V_HH$ domain is a single monomeric variable antibody domain that can be found in camelids. A $V_{NAR}$ domain is a single monomeric variable antibody domain that can be found in cartilaginous fish. Non-limiting aspects of $V_HH$ domains and $V_{NAR}$ domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

A "Fv" fragment includes a non-covalently-linked dimer of one heavy chain variable domain and one light chain variable domain.

A "Fab" fragment includes, the constant domain of the light chain and the first constant domain ($C_{H1}$) of the heavy chain, in addition to the heavy and light chain variable domains of the Fv fragment.

A "F(ab')$_2$" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, *Nature Reviews Drug Discovery* 13:799-801, 2014.

Additional aspects of antibodies and antigen-binding antibody fragments are known in the art.

In some embodiments, any of the antibodies or antigen-binding antibody fragments described herein has a dissociation constant ($K_D$) of less than $1 \times 10^{-5}$ M (e.g., less than $0.5 \times 10^{-5}$ M, less than $1 \times 10^{-6}$ M, less than $0.5 \times 10^{-6}$ M, less than $1 \times 10^{-7}$ M, less than $0.5 \times 10^{-7}$ M, less than $1 \times 10^{-8}$ M, less than $0.5 \times 10^{-8}$ M, less than $1 \times 10^{-9}$ M, less than $0.5 \times 10^{-9}$ M, less than $1 \times 10^{-10}$ M, less than $0.5 \times 10^{-10}$ M, less than $1 \times 10^{-11}$ M, less than $0.5 \times 10^{-11}$ M, or less than $1 \times 10^{-12}$ M), e.g., as measured in phosphate buffered saline using surface plasmon resonance (SPR) for a VEGF protein (e.g., any of the VEGF proteins described herein, e.g., one or more of mature human VEGF-A, mature human VEGF-B, mature human VEGF-C, and mature human VEGF-D).

In some embodiments, any of the antibodies or antigen-binding antibody fragments described herein has a $K_D$ of about $1 \times 10^{-12}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, about $0.5 \times 10^{-10}$ M, about $1 \times 10^{-11}$ M, or about $0.5 \times 10^{-11}$ M (inclusive); about $0.5 \times 10^{-11}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, about $0.5 \times 10^{10}$ M, or about $1 \times 10^{-11}$ M (inclusive); about $1 \times 10^{-11}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, or about $0.5 \times 10^{-10}$ M (inclusive); about $0.5 \times 10^{-10}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, or about $1 \times 10^{-10}$ M (inclusive); about $1 \times 10^{-10}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, or about $0.5 \times 10^{-9}$ M (inclusive); about $0.5 \times 10^{-9}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, or about $1 \times 10^{-9}$ M (inclusive); about $1 \times 10^{-9}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, or about $0.5 \times 10^{-8}$ M (inclusive); about $0.5 \times 10^{-8}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, or about $1 \times 10^{-8}$ M (inclusive); about $1 \times 10^{-8}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, or about $0.5 \times 10^{-7}$ M (inclusive); about $0.5 \times 10^{-7}$ M to about $1 \times 10^{-5}$ M, about $0.5 \times 10^{-5}$ M, about $1 \times 10^{-6}$ M, about $0.5 \times 10^{-6}$ M, or about $1 \times 10^{-7}$ M (inclusive); about $1 \times 10^{-7}$ M to about $1 \times 10^{-5}$ M, about $0.5 \times 10^{-5}$ M, about $1 \times 10^{-6}$ M, or about $0.5 \times 10^{-6}$ M (inclusive); about $0.5 \times 10^{-6}$ M to about $1 \times 10^{-5}$ M, about $0.5 \times 10^{-5}$ M, or about $1 \times 10^{-6}$ M (inclusive); about $1 \times 10^{-6}$ M to about $1 \times 10^{-5}$ M or about $0.5 \times 10^{-5}$ M (inclusive); or about $0.5 \times 10^{-5}$ M to about $1 \times 10^{-5}$ M (inclusive), e.g., as measured in phosphate buffered saline using surface plasmon resonance (SPR), for a VEGF protein (e.g., any of the VEGF proteins described herein, e.g., one or more of mature human VEGF-A, mature human VEGF-B, mature human VEGF-C, and mature human VEGF-D).

A variety of different methods known in the art can be used to determine the $K_D$ values of any of the antibodies or antigen-binding antibody fragments described herein (e.g., an electrophoretic mobility shift assay, a filter binding assay, surface plasmon resonance, and a biomolecular binding kinetics assay, etc.).

In some embodiments of any of the antibodies and/or antigen-binding antibody fragments described herein, the half-life of the antibody and/or the antigen-binding antibody fragment in a subject (e.g., a human) is decreased about 0.5-fold to about 4-fold (e.g., about 0.5-fold to about 3.5-fold, about 0.5-fold to about 3-fold, about 0.5-fold to about 2.5-fold, about 0.5-fold to about 2-fold, about 0.5-fold to about 1.5-fold, about 0.5-fold to about 1-fold, about 1-fold to about 4-fold, about 1-fold to about 3.5-fold, about 1-fold to about 3-fold, about 1-fold to about 2.5-fold, about 1-fold to about 2-fold, about 1.5-fold to about 4-fold, about 1.5-fold to about 3.5-fold, about 1.5-fold to about 3-fold, about 1.5-fold to about 2.5-fold, about 1.5-fold to about 2-fold, about 2-fold to about 4-fold, about 2-fold to about 3.5-fold, about 2-fold to about 3-fold, about 2-fold to about 2.5-fold, about 2.5-fold to about 4-fold, about 2.5-fold to about 3.5-fold, about 2.5-fold to about 3-fold, about 3-fold to about 4-fold, about 3-fold to about 3.5-fold, or about 3.5-fold to about 4-fold) as compared to the half-life of a control antibody and/or a control antigen-binding antibody fragment (e.g., any of the control antibodies and control antigen-binding antibody fragments described herein) in a similar subject. See, e.g., Leabman et al., *MAbs*. 5(6): 896-903, 2013. In some embodiments, an antibody or antigen-binding antibody fragment described herein has one or more amino acid substitutions in the Fc region that decrease its half-life in a mammal, and a control antibody lacks at least one (e.g., lacks all) of these one or more amino acid substitutions in the Fc region.

VEGF

The VEGF gene encodes vascular endothelial growth factor (VEGF), formerly known as fms-like tyrosine kinase (Flt-1). The VEGF protein is a heparin-biding protein that induces migration and proliferation of vascular endothelial cells.

Non-limiting examples of protein and nucleotide sequences encoding a wildtype VEGF protein are shown below.

Human VEGF Transcript Variant 1 Protein Sequence
(SEQ ID NO: 1)
MTDRQTDTAPSPSYHLLPGRRRTVDAAASRGQGPEPAPGGGVEGVGARGV

ALKLFVQLLGCSRFGGAVVRAGEAEPSGAARSASSGREEPQPEEGEEEEE

KEEERGPQWRLGARKPGSWTGEAAVCADSAPAARAPQALARASGRGGRVA

RRGAEESGPPHSPSRRGSASRAGPGRASETMNFLLSWVHWSLALLLYLHH

AKWSQAAPMAEGGGQNHHEVVKFMDVYQRSYCHPIETLVDIFQEYPDEIE

YIFKPSCVPLMRCGGCCNDEGLECVPTEESNITMQIMRIKPHQGQHIGEM

SFLQHNKCECRPKKDRARQEKKSVRGKGKGQKRKRKKSRYKSWSVYVGAR

CCLMPWSLPGPHPCGPCSERRKHLFVQDPQTCKCSCKNTDSRCKARQLEL

NERTCRCDKPRR

Human VEGF Transcript Variant 1 cDNA
(SEQ ID NO: 2)
ct gacggacaga cagacagaca ccgccccag ccccagctac cacctcctcc ccggccggcg gcggacagtg gacgcggcgg cgagccgcgg gcaggggccg gagcccgcgc ccggaggcgg ggtggagggg gtcggggctc gcggcgtcgc actgaaactt ttcgtccaac ttctgggctg ttctcgcttc ggaggagccg tggtccgcgc gggggaagccgagccgagcg gagccgcgag aagtgctagc tcgggccggg aggagccgca gccggaggag ggggaggagg aagaagagaa ggaagaggag aggggggccgc agtggcgact cggcgctcgg aagccgggct catggacggg tgaggcggcg gtgtgcgcag acagtgctcc agccgcgcgc gctcccagg ccctggcccg ggcctcgggc cggggaggaa gagtagctcg ccgaggcgcc gaggagagcg ggccgccca cagcccgagc cggagaggga gcgcgagccg cgccggcccc ggtcgggcct ccgaaaccat gaactttctg ctgtcttggg tgcattggag ccttgccttg ctgctctacc tccaccatgc caagtggtcc caggctgcac ccatggcaga aggaggaggg cagaatcatc acgaagtggt gaagttcatg gatgtctatc agcgcagcta ctgccatcca atcgagaccc tggtggacat cttccaggag taccctgatg agatcgagta catcttcaag ccatcctgtg tgcccctgat gcgatgcggg ggctgctgca atgacgaggg cctggagtgt gtgcccactg aggagtccaa catcaccatg cagattatgc ggatcaaacc tcaccaaggc cagcacatag gagagatgag cttcctacag cacaacaaat gtgaatgcag accaagaaa gatagagcaa gacaagaaaa aaaatcagtt cgaggaaagg gaaaggggca aaaacgaaag cgcaagaaat cccggtataa gtcctggagc gtgtacgttg gtgcccgctg ctgtctaatg ccctggagcc tccctggccc ccatccctgt gggccttgct cagagcggag aaagcatttg tttgtacaag atccgcagac gtgtaaatgt tcctgcaaaa acacagactc gcgttgcaag gcgaggcagc ttgagttaaa cgaacgtact tgcagatgtg acaagccgag gcggtga Human VEGF Transcript Variant 3 Protein Sequence
(SEQ ID NO: 3)
MTDRQTDTAPSPSYHLLPGRRRTVDAAASRGQGPEPAPGGGVEGVGARGV

ALKLFVQLLGCSRFGGAVVRAGEAEPSGAARSASSGREEPQPEEGEEEEE

KEEERGPQWRLGARKPGSWTGEAAVCADSAPAARAPQALARASGRGGRVA

RRGAEESGPPHSPSRRGSASRAGPGRASETMNFLLSWVHWSLALLLYLHH

AKWSQAAPMAEGGGQNHHEVVKFMDVYQRSYCHPIETLVDIFQEYPDEIE

YIFKPSCVPLMRCGGCCNDEGLECVPTEESNITMQIMRIKPHQGQHIGEM

SFLQHNKCECRPKKDRARQEKKSVRGKGKGQKRKRKKSRPCGPCSERRKH

LFVQDPQTCKCSCKNTDSRCKARQLELNERTCRCDKPRR

Human VEGF Transcript Variant 3 cDNA
(SEQ ID NO: 4)
ct gacggacaga cagacagaca ccgccccag ccccagctac cacctcctcc ccggccggcg gcggacagtg gacgcggcgg cgagccgcgg gcaggggccg gagcccgcgc ccggaggcgg ggtggagggg gtcggggctc gcggcgtcgc actgaaactt ttcgtccaac ttctgggctg ttctcgcttc ggaggagccg tggtccgcgc gggggaagccgagccgagcg gagccgcgag aagtgctagc tcgggccggg aggagccgca gccggaggag ggggaggagg aagaagagaa ggaagaggag aggggggccgc agtggcgact cggcgctcgg aagccgggct catggacggg tgaggcggcg gtgtgcgcag acagtgctcc agccgcgcgc gctcccagg ccctggcccg ggcctcgggc cggggaggaa gagtagctcg ccgaggcgcc gaggagagcg ggccgccca -continued
```
cagcccgagc cggagaggga gcgcgagccg cgccggcccc ggtcgggcct ccgaaaccat gaactttctg ctgtcttggg tgcattggag ccttgccttgctgctctacc tccaccatgc caagtggtcc caggctgcac ccatggcaga aggaggaggg cagaatcatc acgaagtggt gaagttcatg gatgtctatc agcgcagcta ctgccatcca atcgagaccc tggtggacat cttccaggag taccctgatg agatcgagta catcttcaag ccatcctgtg tgcccctgat gcgatgcggg ggctgctgca atgacgaggg cctggagtgt gtgccactg aggagtccaa catcaccatg cagattatgc ggatcaaacc tcaccaaggc cagcacatag gagagatgag cttcctacag cacaacaaat gtgaatgcag accaaagaaa gatagagcaa gacaagaaaa aaaatcagtt cgaggaaagg gaaaggggca aaaacgaaag cgcaagaaat cccgtccctg tgggccttgc tcagagcgga gaaagcattt gtttgtacaa gatccgcaga cgtgtaaatg ttcctgcaaa aacacagact cgcgttgcaa ggcgaggcag cttgagttaa acgaacgtac ttgcagatgt gacaagccga ggcggtga
```

Mature Human VEGF-A
                                        (SEQ ID NO: 13)
```
apma egggqnhhev vkfmdvyqrs ychpietlvd ifqeypdeie yifkpscvpl mrcggccnde glecvptees nitmqimrik phqgqhigem sflghnkcec rpkkdrarqe kksvrgkgkg qkrkrkksry kswsvyvgar cclmpwslpg phpcgpcser rkhlfvqdpq tckcsckntd srckarqlel nertcrcdkp rr
```

Mature Human VEGF-B
                                        (SEQ ID NO: 14)
```
pvsqpdapg hqrkvvswid vytratcqpr evvvpltvel mgtvakqlvp scvtvqrcgg ccpddglecv ptgqhqvrmq ilmirypssq lgemsleehs qcecrpkkkd savkpdraat phhrpqprsv pgwdsapgap spadithptp apgpsahaap sttsaltpgp aaaaadaaas svakgga
```

Mature Human VEGF-C
                                        (SEQ ID NO: 15)
```
Ahynteilk sidnewrktq cmprevcidv gkefgvatnt ffkppcvsvy rcggccnseg lqcmntstsy lsktifeitv plsqgpkpvt isfanhtscr cmskldvyrq vhsiirr
```

Mature Human VEGF-D
                                        (SEQ ID NO: 16)
```
fa atfydietlk videewqrtq cspretcvev aselgkstnt ffkppcvnvf rcggccnees licmntstsy iskqlfeisv pltsvpelvp vkvanhtgck clptaprhpy siirr
```

In some examples of any of the antibodies and antigen-binding fragments thereof described herein, the antibody and antigen-binding fragment can bind to a VEGF antigen (e.g., any of the exemplary VEGF proteins described herein, e.g., one or more of mature human VEGF-A, mature human VEGF-B, mature human VEGF-C, and mature human VEGF-D) (e.g., any of the binding affinities described herein).

In some embodiments described herein, an antibody or antigen-binding antibody fragment can decrease an activity of a VEGF (e.g., one or more of any of the exemplary VEGF proteins described herein, e.g., one or more of mature human VEGF-A, mature human VEGF-B, mature human VEGF-C, and mature human VEGF-D). In some embodiments, an antibody or antigen-binding antibody fragment can block a VEGF (e.g., one or more of any of the exemplary VEGF proteins described herein, e.g., one or more of mature human VEGF-A, mature human VEGF-B, mature human VEGF-C, and mature human VEGF-D) from binding to one or more of its receptors (e.g., one or more VEGF receptors) See, e.g., WO 1998/045331, U.S. Pat. No. 9,079,953, U.S. 2015/0147317, U.S. 2016/0289314, Plotkin et al., Otology & Neurotology 33: 1046-1052 (2012); and Ferrara et al. (2005) Biochem Biophys Res Commun 333(2): 328-335. In some embodiments, an antibody or antigen-binding antibody can decrease downstream signaling (e.g., signaling downstream of a VEGF receptor, e.g., one or more of any of the exemplary VEGF receptors described herein, e.g., one or more of human VEGFR-1, human VEGFR-2, and human VEGFR-3). In some embodiments, a decrease in an activity of a VEGF can be detected indirectly, e.g., through an increase in hearing (e.g., a 1% to about 400% increase (or any of the subranges of this range described herein) in hearing) or a decrease (e.g., a 1% to 99%, a 1% to 95%, a 1% to 90%, a 1% to 85%, a 1% to 80%, a 1% to 75%, a 1% to 70%, a 1% to 65%, a 1% to 60%, a 1% to 55%, a 1% to 50%, a 1% to 45%, a 1% to 40%, a 1% to 35%, a 1% to 30%, a 1% to 25%, a 1% to 20%, a 1% to 15%, a 1% to 10%, a 1% to 5%, a 5% to 99%, a 5% to 95%, a 5% to 90%, a 5% to 85%, a 5% to 80%, a 5% to 75%, a 5% to 70%, a 5% to 65%, a 5% to 60%, a 5% to 55%, a 5% to 50%, a 5% to 45%, a 5% to 40%, a 5% to 35%, a 5% to 30%, a 5% to 25%, a 5% to 20%, a 5% to 15%, a 5% to 10%, a 10% to 99%, a 10% to 95%, a 10% to 90%, a 10% to 85%, a 10% to 80%, a 10% to 75%, a 10% to 70%, a 10% to 65%, a 10% to 60%, a 10% to 55%, a 10% to 50%, a 10% to 45%, a 10% to 40%, a 10% to 35%, a 10% to 30%, a 10% to 25%, a 10% to 20%, a 10% to 15%, a 15% to 99%, a 15% to 95%, a 15% to 90%, a 15% to 85%, a 15% to 80%, a 15% to 75%, a 15% to 70%, a 15% to 65%, a 15% to 60%, a 15% to 55%, a 15% to 50%, a 15% to 45%, a 15% to 40%, a 15% to 35%, a 15% to 30%, a 15% to 25%, a 15% to 20%, a 20% to 99%, a 20% to 95%, a 20% to 90%, a 20% to 85%, a 20% to 80%, a 20% to 75%, a 20% to 70%, a 20% to 65%, a 20% to 60%, a 20% to 55%, a 20% to 50%, a 20% to 45%, a 20% to 40%, a 20% to 35%, a 20% to 30%, a 20% to 25%, a 25% to 99%, a 25% to 95%, a 25% to 90%, a 25% to 85%, a 25% to 80%, a 25% to 75%, a 25% to 70%, a 25% to 65%, a 25% to 60%, a 25% to 55%, a 25% to 50%, a 25% to 45%, a 25% to 40%, a 25% to 35%, a 25% to 30%, a 30% to 99%, a 30% to 95%, a 30% to 90%, a 30% to 85%, a 30% to 80%, a 30% to 75%, a 30% to 70%, a 30% to 65%, a 30% to 60%, a 30% to 55%, a 30% to 50%, a 30% to 45%, a 30% to 40%, a 30% to 35%, a 35% to 99%, a 35% to 95%, a 35% to 90%, a 35% to 85%, a 35% to 80%, a 35% to 75%, a 35% to 70%, a 35% to 65%, a 35% to 60%, a 35% to 55%, a 35% to 50%, a 35% to 45%, a 35% to 40%, a 40% to 99%, a 40% to 95%, a 40% to 90%, a 40% to 85%, a 40% to 80%, a 40% to 75%, a 40% to 70%, a 40% to 65%, a 40% to 60%, a 40% to 55%, a 40% to 50%, a 40% to 45%, a 45% to 99%, a 45% to 95%, a 45% to 90%, a 45% to 85%, a 45% to 80%, a 45% to 75%, a 45% to 70%, a 45% to 65%, a 45% to 60%, a 45% to 55%, a 45% to 50%, a 50% to 99%, a 50% to 95%, a 50% to 90%, a 50% to 85%, a 50% to 80%, a 50% to 75%, a 50% to 70%, a 50% to 65%, a 50% to 60%, a 50% to 55%, a 55% to 99%, a 55% to 95%, a 55% to 90%, a 55% to 85%, a 55% to 80%, a 55% to 75%, a 55% to 70%, a 55% to 65%, a 55% to 60%, a 60% to 99%, a 60% to 95%, a 60% to 90%, a 60% to 85%, a 60% to 80%, a 60% to 75%, a 60% to 70%, a 60% to 65%, a 65% to 99%, a 65% to 95%, a 65% to 90%, a 65% to 85%, a 65% to 80%, a 65% to 75%, a 65% to 70%, a 70% to 99%, a 70% to 95%, a 70% to 90%, a 70% to 85%, a 70% to 80%, a 70% to 75%, a 75% to 99%, a 75% to 95%, a 75% to 90%, a 75% to 85%, a 75% to 80%, a 80% to 99%, a 80% to 95%, a 80% to 90%, a 80% to 85%, a 85% to 99%, a 85% to 95%, a 85% to 90%, a 90% to 99%, a 90% to 95%, or a 95% to 99% decrease) in the size or the severity of one or more symptoms of an acoustic neuroma, vestibular schwannoma, or neurofibromatosis type II in a mammal as compared to the level of hearing or size of an acoustic neuroma, vestibular schwannoma, or neurofibromatosis type II in the mammal, respectively, before administration of any of the AAV vectors described herein. In some embodiments, a decrease in a VEGF activity can be detected in an in vitro assay.

In some embodiments, the antibody that specifically binds to a VEGF is bevacizumab (Avastatin®) or an antigen-binding fragment thereof. Bevacizumab (full size antibody ~150 kDa) inhibits all isoforms of VEGF-A. Bevacizumab received Food and Drug administration (FDA) approval in 2004 for colon cancer for intravenous (IV) dose of 4.0-7.5 mg/kg at 2-3 weeks (plasmatic half life 21 days), for intravetrial (IVT) dose 1.25 mg in 0.05 mL (half-life 5.6 days). Bevacizumab has a $K_D$ for VEGF 165 (VEGF-A) of 58 pM. See, e.g., WO 2017/050825. In some embodiments, the antibody that specifically binds to a VEGF is ranibizumab (Lucentis®), or an antigen-binding fragment thereof. Ranibizumab (~50 kDa) inhibits all isoforms of VEGF-A. Ranibizumab received FDA approval in 2006 for ocular use for intravenous (IV) dose of 4.0-7.5 mg/kg at 2-3 weeks (plasma half life of 0.5 days), for intravetrial (IVT) dose 0.5 mg in 0.05 mL (half-life of 3.2 days). Ranibizumab has a $K_D$ for VEGF 165 (VEGF-A) of 46 pM. See, e.g., WO 2014/178078. In some embodiments, the antibody that specifically binds to VEGF is sevacizumab (APX003/SIM-BD0801), or an antigen-binding fragment thereof.

```
Amino Acid Encoding Light Chain of
Bevacizumab
                                    (SEQ ID NO: 5)
DIQMTQSPSSLSASVGDRVTITCSASQDISNYLNWYQQKPGKAPKVLIYF

TSSLHSGVPSRFSGSGSGTDFTLTISSLQPEDFATYYCQQYSTVPWTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Amino Acid Encoding Heavy Chain of
Bevacizumab
                                    (SEQ ID NO: 6)
EVQLVESGGGLVQPGGSLRLSCAASGYTFTNYGMNWVRQAPGKGLEWVGW

INTYTGEPTYAADFKRRFTFSLDTSKSTAYLQMNSLRAEDTAVYYCAKYP

HYYGSSHWYFDVWGQGTLVTVSSASTKGPSVFPLAPSSKSTSGGTAALGC

LVKDYFPEPVTVSWNSGALTSGVHTFPAVLQSSGLYSLSSVVTVPSSSLG
```

```
                    -continued
TQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGK
```

In some embodiments of the antibodies that specifically bind to VEGF and antigen-binding fragments thereof described herein, the antibody or antigen-binding fragments thereof includes a variable light chain domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the variable light chain domain of bevacizumab, and/or includes a variable heavy chain domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the variable heavy chain domain of bevacizumab.

In some embodiments of the antibodies that specifically bind to VEGF and antigen-binding fragments thereof described herein, the antibody or antigen-binding fragments thereof includes a variable light chain domain that is or includes the variable light chain domain of bevacizumab, and/or a variable heavy chain domain that is or includes the variable heavy chain domain of bevacizumab. In some embodiments of the antibodies that specifically bind to VEGF and antigen-binding fragments thereof described herein, the antibody or antigen-binding fragments thereof includes a variable light chain domain that is or includes the sequence of variable light chain domain of bevacizumab, except that it includes one, two, three, four, five, six, seven, eight, nine, ten, eleven, twelve, thirteen, fourteen, or fifteen amino acid substitutions, and/or includes a variable heavy chain domain that is or includes the sequence of variable heavy chain of bevacizumab, except that it includes one, two, three, four, five, six, seven, eight, nine, ten, eleven, twelve, thirteen, fourteen, or fifteen amino acid substitutions. In some embodiments the first antigen-binding domain includes the three CDRs in the light chain variable domain of bevacizumab, and/or the three CDRs in the heavy chain variable domain of bevacizumab.

```
Amino Acid Encoding Light Chain of
Ranibizumab
                                    (SEQ ID NO: 7)
DIQLTQSPSSLSASVGDRVTITCSASQDISNYLNWYQQKPGKAPKVLIYF

TSSLHSGVPSRFSGSGSGTDFTLTISSLQPEDFATYYCQQYSTVPWTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Amino Acid Encoding Heavy Chain of
Ranibizumab
                                    (SEQ ID NO: 8)
EVQLVESGGGLVQPGGSLRLSCAASGYDFTHYGMNWVRQAPGKGLEWVGW

INTYTGEPTYAADFKRRFTFSLDTSKSTAYLQMNSLRAEDTAVYYCAKYP
```

-continued

YYYGTSHWYFDVWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHL

In some embodiments of the antibodies that specifically bind to VEGF and antigen-binding fragments thereof described herein, the antibody or antigen-binding fragments thereof includes a variable light chain domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the variable light chain domain of ranibizumab, and/or includes a variable heavy chain domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the variable heavy chain domain of ranibizumab.

In some embodiments of the antibodies that specifically bind to VEGF and antigen-binding fragments thereof described herein, the antibody or antigen-binding fragments thereof includes a variable light chain domain that is or includes the variable light chain domain of ranibizumab, and/or a variable heavy chain domain that is or includes the variable heavy chain domain of ranibizumab. In some embodiments of the antibodies that specifically bind to VEGF and antigen-binding fragments thereof described herein, the antibody or antigen-binding fragments thereof includes a variable light chain domain that is or includes the sequence of variable light chain domain of ranibizumab, except that it includes one, two, three, four, five, six, seven, eight, nine, ten, eleven, twelve, thirteen, fourteen, or fifteen amino acid substitutions, and/or includes a variable heavy chain domain that is or includes the sequence of variable heavy chain domain of ranibizumab, except that it includes one, two, three, four, five, six, seven, eight, nine, ten, eleven, twelve, thirteen, fourteen, or fifteen amino acid substitutions. In some embodiments the first antigen-binding domain includes the three CDRs in the light chain variable domain of ranibizumab, and/or the three CDRs in the heavy chain variable domain of ranibizumab.

Soluble VEGF Receptors

A soluble VEGF receptor is a polypeptide that includes a portion of an extracellular region of one or more (e.g., two or three) mammalian VEGF receptor(s) (e.g., one or more of VEGFR-1, VEGFR-2, and VEGFR-3) operably linked to a signal peptide (e.g., any of the exemplary signal peptides described herein), where the soluble VEGF receptor is capable of specifically binding to one or more mammalian VEGF protein(s) (e.g., one or more (e.g., two, three, or four) of VEGF-A, VEGF-B, VEGF-C, and VEGF-D, e.g., one or more (e.g., two, three, or four) of human wildtype VEGF-A, human wildtype VEGF-B, human wildtype VEGF-C, and human wildtype VEGF-D).

In some examples, a soluble VEGF receptor includes a portion (e.g., about 10 amino acids to about 732 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 250 amino acids, about 10 amino acids to about 200 amino acids, about 10 amino acids to about 150 amino acids, about 10 amino acids to about 100 amino acids, about 10 amino acids to about 50 amino acids, about 50 amino acids to about 732 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 250 amino acids, about 50 amino acids to about 200 amino acids, about 50 amino acids to about 150 amino acids, about 50 amino acids to about 100 amino acids, about 100 amino acids to about 732 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 150 amino acids, about 150 amino acids to about 732 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 250 amino acids, about 150 amino acids to about 200 amino acids, about 200 amino acids to about 732 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 732 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 732 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 732 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 732 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 732 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 732 amino acids, about 500 amino acids to about 700 amino acids, about 500 amino acids to about 650 amino acids, about 500 amino acids to about 600 amino acids, about 500 amino acids to about 550 amino acids, about 550 amino acids to about 732 amino acids, about 550 amino acids to about 700 amino acids, about 550 amino acids to about 650 amino acids, about 550 amino acids to about 600 amino acids, about 600 amino acids to about 732 amino acids, about 600 amino acids to about 700 amino acids, about 600 amino acids to about 650 amino acids, about 650 amino acids to about 732 amino acids, about 650 amino acids to about 700 amino acids, or about 700 amino acids to about 732 amino acids) of an extracellular region of VEGFR-1 (e.g., a contiguous sequence from wildtype human VEGFR-1 (e.g., a contiguous sequence including one or more (e.g., one, two, three, four, five, six, or seven) immunoglobulin-like domains in the extracellular region from wildtype human VEGFR-1 (e.g., SEQ ID NO: 23) or a sequence that is at least 80% (e.g., at least 82%, at least 84%, at least 86%, at least 88%, at least 90%, at least 92%, at least 94%, at least 96%, at least 98%, or at least 99%) identical to a contiguous sequence from wildtype human VEGFR-1, e.g., a sequence that is at least 80% (e.g., least 82%, at least 84%, at least 86%, at least 88%, at least 90%, least 92%, at least 94%, at least 96%, at least 98%, or at least 99%) identical to a contiguous sequence in SEQ ID NO: 23).

In some examples, a soluble VEGF receptor includes a portion (e.g., about 20 amino acids to about 745 amino acids, or any of the subranges of this range described herein) of an extracellular region of VEGFR-2 (e.g., a contiguous sequence from wildtype human VEGFR-2 (e.g., a contiguous sequence including one or more (e.g., one, two, three, four, five, six, or seven) immunoglobulin-like domains in the extracellular region from wildtype human VEGFR-2 (e.g., SEQ ID NO: 26) or a sequence that is at least 80% (e.g., at least 82%, at least 84%, at least 86%, at least 88%, at least 90%, at least 92%, at least 94%, at least 96%, at least 98%, or at least 99%) identical to a contiguous sequence from wildtype human VEGFR-2, e.g., a sequence that is at least 80% (e.g., at least 82%, at least 84%, at least 86%, at least 88%, at least 90%, at least 92%, at least 94%, at least 96%, at least 98%, or at least 99%) identical to a contiguous sequence in SEQ ID NO: 26).

In some examples, a soluble VEGF receptor includes a portion of an extracellular region of VEGFR-1 (e.g., any of the portions of an extracellular region of VEGFR-1 described herein) and a portion of an extracellular region of VEGFR-2 (e.g., any of the portions of an extracellular region of VEGFR-2 described herein). For example, a soluble VEGF receptor can include one or more (e.g., two, three, four, five, six, or seven) immunoglobulin-like domains in the extracellular region from wildtype human VEGFR-1 and one or more (e.g., two, three, four, five, six, or seven) immunoglobulin-like domains in the extracellular region from wildtype human VEGFR-2 (e.g., aflibercept).

In some examples, a soluble VEGF receptor includes a portion (e.g., about 20 amino acids to about 751 amino acids, or any of the subranges of this range described herein) of an extracellular region of VEGFR-3 (e.g., a contiguous sequence from wildtype human VEGFR-3 (e.g., a contiguous sequence including one or more (e.g., one, two, three, four, five, six, or seven) immunoglobulin-like domains in the extracellular region from wildtype human VEGFR-3 (e.g., SEQ ID NO: 29) or a sequence that is at least 80% (e.g., at least 82%, at least 84%, at least 86%, at least 88%, at least 90%, at least 92%, at least 94%, at least 96%, at least 98%, or at least 99%) identical to a contiguous sequence from wildtype human VEGFR-3, e.g., a sequence that is at least 80% (e.g., at least 82%, at least 84%, at least 86%, at least 88%, at least 90%, at least 92%, at least 94%, at least 96%, at least 98%, or at least 99%) identical to a contiguous sequence in SEQ ID NO: 29).

Non-limiting examples of extracellular regions of different mammalian VEGFR-1, different mammalian VEGFR-2, and different mammalian VEGFR-3 are described herein. Non-limiting examples of protein and nucleotide sequences encoding a wildtype VEGF receptor protein are shown below. As one skilled in the art can appreciate, a substitution in an amino acid that is conserved between species is more likely to result in a change in the function of a protein, while a substitution in an amino acid position that is not converted between species is less likely to have an affect on the function of a protein.

```
Human VEGF Receptor 1 Isoform 2 Protein
Sequence
                                       (SEQ ID NO: 17)
MVSYWDTGVLLCALLSCLLLTGSSSGSKLKDPELSLKGTQHIMQAGQTLH

LQCRGEAAHKWSLPEMVSKESERLSITKSACGRNGKQFCSTLTLNTAQAN

HTGFYSCKYLAVPTSKKKETESAIYIFISDTGRPFVEMYSEIPEIIHMTE

GRELVIPCRVTSPNITVTLKKFPLDTLIPDGKRIIWDSRKGFIISNATYK

EIGLLTCEATVNGHLYKTNYLTHRQTNTIIDVQISTPRPVKLLRGHTLVL

NCTATTPLNTRVQMTWSYPDEKNKRASVRRRIDQSNSHANIFYSVLTIDK

MQNKDKGLYTCRVRSGPSFKSVNTSVHIYDKAFITVKHRKQQVLETVAGK

RSYRLSMKVKAFPSPEVVWLKDGLPATEKSARYLTRGYSLIIKDVTEEDA

GNYTILLSIKQSNVFKNLTATLIVNVKPQIYEKAVSSFPDPALYPLGSRQ

ILTCTAYGIPQPTIKWFWHPCNHNHSEARCDFCSNNEESFILDADSNMGN

RIESITQRMAIIEGKNKMASTLVVADSRISGIYICIASNKVGTVGRNISF

YITDVPNGFHVNLEKMPTEGEDLKLSCTVNKFLYRDVTWILLRTVNNRTM

HYSISKQKMAITKEHSITLNLTIMNVSLQDSGTYACRARNVYTGEEILQK

KEITIRGEHCNKKAVFSRISKFKSTRNDCTTQSNVKH

Human VEGF Receptor 1 Isoform 2 cDNA
                                       (SEQ ID NO: 18)
ATGGTCAGCTACTGGGACACCGGGGTCCTGCTGTGCGCGCTGCTCAGCTG

TCTGCTTCTCACAGGATCTAGTTCAGGTTCAAAATTAAAAGATCCTGAAC

TGAGTTTAAAAGGCACCCAGCACATCATGCAAGCAGGCCAGACACTGCAT

CTCCAATGCAGGGGGGAAGCAGCCCATAAATGGTCTTTGCCTGAAATGGT

GAGTAAGGAAAGCGAAAGGCTGAGCATAACTAAATCTGCCTGTGGAAGAA
```

ATGGCAAACAATTCTGCAGTACTTTAACCTTGAACACAGCTCAAGCAAAC

CACACTGGCTTCTACAGCTGCAAATATCTAGCTGTACCTACTTCAAAGAA

GAAGGAAACAGAATCTGCAATCTATATATTTATTAGTGATACAGGTAGAC

CTTTCGTAGAGATGTACAGTGAAATCCCCGAAATTATACACATGACTGAA

GGAAGGGAGCTCGTCATTCCCTGCCGGGTTACGTCACCTAACATCACTGT

TACTTTAAAAAAGTTTCCACTTGACACTTTGATCCCTGATGGAAAACGCA

TAATCTGGGACAGTAGAAAGGGCTTCATCATATCAAATGCAACGTACAAA

GAAATAGGGCTTCTGACCTGTGAAGCAACAGTCAATGGGCATTTGTATAA

GACAAACTATCTCACACATCGACAAACCAATACAATCATAGATGTCCAAA

TAAGCACACCACGCCCAGTCAAATTACTTAGAGGCCATACTCTTGTCCTC

AATTGTACTGCTACCACTCCCTTGAACACGAGAGTTCAAATGACCTGGAG

TTACCCTGATGAAAAAATAAGAGAGCTTCCGTAAGGCGACGAATTGACC

AAAGCAATTCCCATGCCAACATATTCTACAGTGTTCTTACTATTGACAAA

ATGCAGAACAAAGACAAAGGACTTTATACTTGTCGTGTAAGGAGTGGACC

ATCATTCAAATCTGTTAACACCTCAGTGCATATATATGATAAAGCATTCA

TCACTGTGAAACATCGAAAACAGCAGGTGCTTGAAACCGTAGCTGGCAAG

CGGTCTTACCGGCTCTCTATGAAAGTGAAGGCATTTCCCTCGCCGGAAGT

TGTATGGTTAAAAGATGGGTTACCTGCGACTGAGAAATCTGCTCGCTATT

TGACTCGTGGCTACTCGTTAATTATCAAGGACGTAACTGAAGAGGATGCA

GGGAATTATACAATCTTGCTGAGCATAAAACAGTCAAATGTGTTTAAAAA

CCTCACTGCCACTCTAATTGTCAATGTGAAACCCCAGATTTACGAAAAGG

CCGTGTCATCGTTTCCAGACCCGGCTCTCTACCCACTGGGCAGCAGACAA

ATCCTGACTTGTACCGCATATGGTATCCCTCAACCTACAATCAAGTGGTT

CTGGCACCCCTGTAACCATAATCATTCCGAAGCAAGGTGTGACTTTTGTT

CCAATAATGAAGAGTCCTTTATCCTGGATGCTGACAGCAACATGGGAAAC

AGAATTGAGAGCATCACTCAGCGCATGGCAATAATAGAAGGAAAGAATAA

GATGGCTAGCACCTTGGTTGTGGCTGACTCTAGAATTTCTGGAATCTACA

TTTGCATAGCTTCCAATAAAGTTGGGACTGTGGGAAGAAACATAAGCTTT

TATATCACAGATGTGCCAAATGGGTTTCATGTTAACTTGGAAAAAATGCC

GACGGAAGGAGAGGACCTGAAACTGTCTTGCACAGTTAACAAGTTCTTAT

ACAGAGACGTTACTTGGATTTTACTGCGGACAGTTAATAACAGAACAATG

CACTACAGTATTAGCAAGCAAAAAATGGCCATCACTAAGGAGCACTCCAT

CACTCTTAATCTTACCATCATGAATGTTTCCCTGCAAGATTCAGGCACCT

ATGCCTGCAGAGCCAGGAATGTATACACAGGGGAAGAAATCCTCCAGAAG

AAAGAAATTACAATCAGAGGTGAGCACTGCAACAAAAAGGCTGTTTTCTC

TCGGATCTCCAAATTTAAAAGCACAAGGAATGATTGTACCACACAAAGTA

ATGTAAAACATTAA

Human VEGF Receptor 1 Isoform 3 Protein
Sequence (sFlt1-14)
(SEQ ID NO: 14)
MVSYWDTGVLLCALLSCLLLTGSSSGSKLKDPELSLKGTQHIMQAGQTLH

LQCRGEAAHKWSLPEMVSKESERLSITKSACGRNGKQFCSTLTLNTAQAN

HTGFYSCKYLAVPTSKKKETESAIYIFISDTGRPFVEMYSEIPEIIHMTE

GRELVIPCRVTSPNITVTLKKFPLDTLIPDGKRIIWDSRKGFIISNATYK

EIGLLTCEATVNGHLYKTNYLTHRQTNTIIDVQISTPRPVKLLRGHTLVL

NCTATTPLNTRVQMTWSYPDEKNKRASVRRRIDQSNSHANIFYSVLTIDK

MQNKDKGLYTCRVRSGPSFKSVNTSVHIYDKAFITVKHRKQQVLETVAGK

RSYRLSMKVKAFPSPEVVWLKDGLPATEKSARYLTRGYSLIIKDVTEEDA

GNYTILLSIKQSNVFKNLTATLIVNVKPQIYEKAVSSFPDPALYPLGSRQ

ILTCTAYGIPQPTIKWFWHPCNHNHSEARCDFCSNNEESFILDADSNMGN

RIESITQRMAIIEGKNKMASTLVVADSRISGIYICIASNKVGTVGRNISF

YITDVPNGFHVNLEKMPTEGEDLKLSCTVNKFLYRDVTWILLRTVNNRTM

HYSISKQKMAITKEHSITLNLTIMNVSLQDSGTYACRARNVYTGEEILQK

KEITIRDQEAPYLLRNLSDHTVAISSSTTLDCHANGVPEPQITWFKNNHK

IQQEPELYTSTSPSSSSSSSPLSSSSSSSSSSS

Human VEGF Receptor 1 Isoform 3 cDNA
(SEQ ID NO: 20)
ATGGTCAGCTACTGGGACACCGGGGTCCTGCTGTGCGCGCTGCTCAGCTG

TCTGCTTCTCACAGGATCTAGTTCAGGTTCAAAATTAAAAGATCCTGAAC

TGAGTTTAAAAGGCACCCAGCACATCATGCAAGCAGGCCAGACACTGCAT

CTCCAATGCAGGGGGGAAGCAGCCCATAAATGGTCTTTGCCTGAAATGGT

GAGTAAGGAAAGCGAAAGGCTGAGCATAACTAAATCTGCCTGTGGAAGAA

ATGGCAAACAATTCTGCAGTACTTTAACCTTGAACACAGCTCAAGCAAAC

CACACTGGCTTCTACAGCTGCAAATATCTAGCTGTACCTACTTCAAAGAA

GAAGGAAACAGAATCTGCAATCTATATATTTATTAGTGATACAGGTAGAC

CTTTCGTAGAGATGTACAGTGAAATCCCCGAAATTATACACATGACTGAA

GGAAGGGAGCTCGTCATTCCCTGCCGGGTTACGTCACCTAACATCACTGT

TACTTTAAAAAAGTTTCCACTTGACACTTTGATCCCTGATGGAAAACGCA

TAATCTGGGACAGTAGAAAGGGCTTCATCATATCAAATGCAACGTACAAA

GAAATAGGGCTTCTGACCTGTGAAGCAACAGTCAATGGGCATTTGTATAA

GACAAACTATCTCACACATCGACAAACCAATACAATCATAGATGTCCAAA

TAAGCACACCACGCCCAGTCAAATTACTTAGAGGCCATACTCTTGTCCTC

AATTGTACTGCTACCACTCCCTTGAACACGAGAGTTCAAATGACCTGGAG

TTACCCTGATGAAAAAATAAGAGAGCTTCCGTAAGGCGACGAATTGACC

AAAGCAATTCCCATGCCAACATATTCTACAGTGTTCTTACTATTGACAAA

ATGCAGAACAAAGACAAAGGACTTTATACTTGTCGTGTAAGGAGTGGACC

ATCATTCAAATCTGTTAACACCTCAGTGCATATATATGATAAAGCATTCA

TCACTGTGAAACATCGAAAACAGCAGGTGCTTGAAACCGTAGCTGGCAAG

CGGTCTTACCGGCTCTCTATGAAAGTGAAGGCATTTCCCTCGCCGGAAGT

TGTATGGTTAAAAGATGGGTTACCTGCGACTGAGAAATCTGCTCGCTATT

TGACTCGTGGCTACTCGTTAATTATCAAGGACGTAACTGAAGAGGATGCA

GGGAATTATACAATCTTGCTGAGCATAAAACAGTCAAATGTGTTTAAAAA

CCTCACTGCCACTCTAATTGTCAATGTGAAACCCCAGATTTACGAAAAGG

```
CCGTGTCATCGTTTCCAGACCCGGCTCTCTACCCACTGGGCAGCAGACAA

ATCCTGACTTGTACCGCATATGGTATCCCTCAACCTACAATCAAGTGGTT

CTGGCACCCCTGTAACCATAATCATTCCGAAGCAAGGTGTGACTTTTGTT

CCAATAATGAAGAGTCCTTTATCCTGGATGCTGACAGCAACATGGGAAAC

AGAATTGAGAGCATCACTCAGCGCATGGCAATAATAGAAGGAAAGAATAA

GATGGCTAGCACCTTGGTTGTGGCTGACTCTAGAATTTCTGGAATCTACA

TTTGCATAGCTTCCAATAAAGTTGGGACTGTGGGAAGAAACATAAGCTTT

TATATCACAGATGTGCCAAATGGGTTTCATGTTAACTTGGAAAAAATGCC

GACGGAAGGAGAGGACCTGAAACTGTCTTGCACAGTTAACAAGTTCTTAT

ACAGAGACGTTACTTGGATTTTACTGCGGACAGTTAATAACAGAACAATG

CACTACAGTATTAGCAAGCAAAAAATGGCCATCACTAAGGAGCACTCCAT

CACTCTTAATCTTACCATCATGAATGTTTCCCTGCAAGATTCAGGCACCT

ATGCCTGCAGAGCCAGGAATGTATACACAGGGGAAGAAATCCTCCAGAAG

AAAGAAATTACAATCAGAGATCAGGAAGCACCATACCTCCTGCGAAACCT

CAGTGATCACACAGTGGCCATCAGCAGTTCCACCACTTTAGACTGTCATG

CTAATGGTGTCCCCGAGCCTCAGATCACTTGGTTTAAAAACAACCACAAA

ATACAACAAGAGCCTGAACTGTATACATCAACGTCACCATCGTCATCGTC

ATCATCACCATTGTCATCATCATCATCATCGTCATCATCATCATCAT

AG

Human VEGF Receptor 1 Isoform 4 Protein
Sequence
                                    (SEQ ID NO: 21)
MVSYWDTGVLLCALLSCLLLTGSSSGSKLKDPELSLKGTQHIMQAGQTLH

LQCRGEAAHKWSLPEMVSKESERLSITKSACGRNGKQFCSTLTLNTAQAN

HTGFYSCKYLAVPTSKKKETESAIYIFISDTGRPFVEMYSEIPEIIHMTE

GRELVIPCRVTSPNITVTLKKFPLDTLIPDGKRIIWDSRKGFIISNATYK

EIGLLTCEATVNGHLYKTNYLTHRQTNTIIDVQISTPRPVKLLRGHTLVL

NCTATTPLNTRVQMTWSYPDEKNKRASVRRRIDQSNSHANIFYSVLTIDK

MQNKDKGLYTCRVRSGPSFKSVNTSVHIYDKAFITVKHRKQQVLETVAGK

RSYRLSMKVKAFPSPEVVWLKDGLPATEKSARYLTRGYSLIIKDVTEEDA

GNYTILLSIKQSNVFKNLTATLIVNVKPQIYEKAVSSFPDDPALYPLGSRQ

ILTCTAYGIPQPTIKWFWHPCNHNHSEARCDFCSNNEESFILDADSNMGN

RIESITQRMAIIEGKNKLPPANSSFMLPPTSFSSNYFHFLP

Human VEGF Receptor 1 Isoform 4 cDNA
                                    (SEQ ID NO: 22)
ATGGTCAGCTACTGGGACACCGGGGTCCTGCTGTGCGCGCTGCTCAGCTG

TCTGCTTCTCACAGGATCTAGTTCAGGTTCAAAATTAAAAGATCCTGAAC

TGAGTTTAAAAGGCACCCAGCACATCATGCAAGCAGGCCAGACACTGCAT

CTCCAATGCAGGGGGGAAGCAGCCCATAAATGGTCTTTGCCTGAAATGGT

GAGTAAGGAAAGCGAAAGGCTGAGCATAACTAAATCTGCCTGTGGAAGAA

ATGGCAAACAATTCTGCAGTACTTTAACCTTGAACACAGCTCAAGCAAAC

CACACTGGCTTCTACAGCTGCAAATATCTAGCTGTACCTACTTCAAAGAA

GAAGGAAACAGAATCTGCAATCTATATATTTATTAGTGATACAGGTAGAC
```

```
CTTTCGTAGAGATGTACAGTGAAATCCCCGAAATTATACACATGACTGAA

GGAAGGGAGCTCGTCATTCCCTGCCGGGTTACGTCACCTAACATCACTGT

TACTTTAAAAAAGTTTCCACTTGACACTTTGATCCCTGATGGAAAACGCA

TAATCTGGGACAGTAGAAAGGGCTTCATCATATCAAATGCAACGTACAAA

GAAATAGGGCTTCTGACCTGTGAAGCAACAGTCAATGGGCATTTGTATAA

GACAAACTATCTCACACATCGACAAACCAATACAATCATAGATGTCCAAA

TAAGCACACCACGCCCAGTCAAATTACTTAGAGGCCATACTCTTGTCCTC

AATTGTACTGCTACCACTCCCTTGAACACGAGAGTTCAAATGACCTGGAG

TTACCCTGATGAAAAAAATAAGAGAGCTTCCGTAAGGCGACGAATTGACC

AAAGCAATTCCCATGCCAACATATTCTACAGTGTTCTTACTATTGACAAA

ATGCAGAACAAAGACAAAGGACTTTATACTTGTCGTGTAAGGAGTGGACC

ATCATTCAAATCTGTTAACACCTCAGTGCATATATATGATAAAGCATTCA

TCACTGTGAAACATCGAAAACAGCAGGTGCTTGAAACCGTAGCTGGCAAG

CGGTCTTACCGGCTCTCTATGAAAGTGAAGGCATTTCCCTCGCCGGAAGT

TGTATGGTTAAAAGATGGGTTACCTGCGACTGAGAAATCTGCTCGCTATT

TGACTCGTGGCTACTCGTTAATTATCAAGGACGTAACTGAAGAGGATGCA

GGGAATTATACAATCTTGCTGAGCATAAAACAGTCAAATGTGTTTAAAAA

CCTCACTGCCACTCTAATTGTCAATGTGAAACCCCAGATTTACGAAAAGG

CCGTGTCATCGTTTCCAGACCCGGCTCTCTACCCACTGGGCAGCAGACAA

ATCCTGACTTGTACCGCATATGGTATCCCTCAACCTACAATCAAGTGGTT

CTGGCACCCCTGTAACCATAATCATTCCGAAGCAAGGTGTGACTTTTGTT

CCAATAATGAAGAGTCCTTTATCCTGGATGCTGACAGCAACATGGGAAAC

AGAATTGAGAGCATCACTCAGCGCATGGCAATAATAGAAGGAAAGAATAA

GCTTCCACCAGCTAACAGTTCTTTCATGTTGCCACCTACAAGCTTCTCTT

CCAACTACTTCCATTTCCTTCCGTGA

Extracellular Region of Wildtype Human
VEGFR-1 (the seven Ig-like domains are
shown in bold and underlined)
                                    (SEQ ID NO: 23)
sklk dpelslkgtq himgagqtlh lqcrgeaahk wslpemvske serlsitksa cgrngkqfcs tltlntaqan htgfysckyl avptskkket esaiyifisd tgrpfvemys eipeiihmte grelvipcry tspnitvtlk kfpldtlipd gkriiwdsrk gfiisnatyk eiglltceat vnghlyktny lthrqtntii dvqistprpv kllrghtivl nctattpint rvqmtwsypd eknkrasvrr ridqsnshan ifysvltidk mqnkdkglyt crvrsgpsfk svntsvhiyd kafitvkhrk qqvletvagk rsyrlsmkvk afpspevvwl kdglpateks aryltrgysl iikdvteeda gnytillsik qsnvfknita tlivnvkpqi yekayssfpd palvplgsrq iltctaygip qptikwfwhp cnhnhsearc dfcsnneesf ildadsnmgn riesitqrma iiegknkmas tivvadsris giyiciasnk vgtvgrnisf yitdvpngfh vnlekmpteg edlklsctvn kflyrdvtwi
```

-continued llrtvnnrtm hysiskqkma itkehsitln ltimnvslqd sgtyacrarn vytgeeilqk keitirdqea pyllrnlsdh tvaissssttl dchangvpep qitwfknnhk iqqepqiilq pgsstlfier vteedegvyh ckatnqkgsv essayltvqg tsdksnle

Extracellular Region of Wildtype Mouse
VEGFR-1
(SEQ ID NO: 24)
ygsgsklk vpelslkgtq hvmqagqtlf lkcrgeaahs wslpttvsqe dkrlsitpps acgrdnrqfc stltldtaqa nhtglytcry lptstskkkk aessiyifvs dagspfiemh tdipklvhmt egrqlliper vtspnvtvtl kkfpfdtltp dgqritwdsr rgfiianaty keigllncea tvnghlyqtn ylthrqtnti ldvqirppsp vrllhgqtiv lnctatteln trvqmswnyp gkatkrasir qridrshshn nvfhsvlkin nvesrdkgly tcrvksgssf qsfntsvhvy ekgfisvkhr kqpvqettag rrsyrlsmkv kafpspeivw lkdgspatlk sarylvhgys liikdvtted agdytillgi kqsrlfknit atlivnvkpq iyeksysslp spplyplgsr qvltctvygi prptitwlwh pchhnhsker ydfctenees fildpssnlg nriesisqrm tviegtnktv stivvadsqt pgiyscrafn kigtvernik fyvtdvpngf hvslekmpae gedlklscvv nkflyrditw illrtvnnrt mhhsiskqkm attqdysitl nlviknvsle dsgtyacrar niytgedilr ktevlvrdse aphllqnlsd yevsisgstt ldcgargvpa pqitwfknnh kiqqepgiil gpgnstlfie rvteedegvy rcratnqkga vesaayltvq gtsdksnle Extracellular Region of Wildtype Rat
VEGFR-1
(SEQ ID NO: 25)
ycsgsklk gpelslkgtq hvmqagqtlf lkcrgeaahs wslpttvsqe dkklsvtrsa cgrnnrqfcs tltlnmaqan htglyscryl pkstskekkm esaiyifvsd agspfiemhs dipklvhmte greliipery tspnitvtlk kfpfdaltpd gqriawdsrr gfiianatyk eiglltceat vnghlyqtsy lthrqtntil dvqisppspv rflrgqtivl nctvttdlnt rvqmswnypg katkrasirq ridqsnphsn vfhsvlkinn vesrdkglyt crvksgssfr tfntsvhvye kgfisvkhrk qqvqetiagk rshrlsmkvk afpspevvwl kdgvpateks arysvhgysl iikdvtaeda gdytillgik qsklfrnita tlivnvkpqi yeksysslps pplyplgsrq vltctvygip qptikwlwhp chynhskern dfcfgseesf ildsssnign riegitqrmm viegtnktvs tivvadsrtp gsysckafnk igtverdirf yvtdvpngfh vslekipteg edlklscvvs kflyrditwi llrtvnnrtm hhsiskqkma ttqdysitln lviknvsled sgtyacrarn iytgeeilrk tevlvrdlea plllqnlsdh evsisgsttl dcqargvpap qitwfknnhk iqqepgiilg pgnstlfier vteedegvyr cratnqkgvv essayltvqg tsdksnle Extracellular Region of Wildtype Human
VEGFR-2 (the seven Ig-like domains are
shown in bold and underlined)
(SEQ ID NO: 26)
asvglpsysld lprlsiqkdi ltikanttlq itcrgqrdld wlwpnngsgs eqrvevtecs dglfcktlti pkvigndtga ykcfyretdl asviyvyvqd yrspfiasys dqhgvvyite nknktvvipc lgsisnlnvs lcarypekrf vpdgnriswd skkgftipsy misyagmvfc eakindesyq simyivvvg yriydvvlsp shgielsvge klvinctart elnvgidfnw eypsskhqhk klvnrdlktq sgsemkkfls tltidgvtrs dqglytcaas sglmtkknst fvrvhekpfv afgsgmeslv eatvgervri pakylgyppp eikwykngip lesnhtikag hvltimevse rdtgnytvil tnpiskekqs hvvslvvyvp pqiqekslis pvdsvqygtt qtltctvyai ppphhihwyw qleeecanep sqaysvtnpy pceewrsved fqggnkievn knqfaliegk nktvstiviq aanvsalykc eavnkvgrge rvisfhvtrg peitlqpdmq pteqesyslw ctadrstfen ltwyklgpqp lpihvgelpt pvcknldtlw klnatmfsns tndilimelk naslqdqgdy vclaqdrktk krhcvvrqlt vlervaptit qnlengttsi gesievscta sgnpppqimw fkdnetived sgivlkdgnr nltirrvrke deglytcqac svlgcakvea ffiiegaqek tnle

Extracellular Region of Wildtype Mouse
VEGFR-2
(SEQ ID NO: 27)
asvglpgdflh ppklstqkdi ltilanttlq itcrgqrdld wlwpnaqrds eervlvtecg ggdsifcktl tiprvvgndt gaykcsyrdv diastvyvyv rdyrspfias vsdqhgivyi tenknktvvi pergsisnln vslcarypek rfvpdgnris wdseigftlp symisyagmv fceakindet yqsimyivvv vgyriydvil sppheielsa geklvincta rtelnvgldf twhsppsksh hkkivnrdvk pfpgtvakmf lstltiesvt ksdqgeytcv assgrmikrn rtfvrvhtkp fiafgsgmks lveatvgsqv ripvkylsyp apdikwyrng rpiesnytmi vgdeltimev terdagnytv iltnpismek qshmvslvvn vppqigekal ispmdsyqyg tmqtltctvy anpplhhiqw ywqleeacsy rpgqtspyac kewrhvedfq ggnkievtkn -continued

```
qyaliegknk tvstiviqaa nvsalykcea inkagrgery isfhvirgpe itvqpaaqpt eqesysllct adrntfenit wyklgsqats vhmgesltpv cknldalwkl ngtmfsnstn dilivafqna slqdqgdyvc saqdkktkkr hclvkqliil ermapmitgn lenqtttige tievtcpasg nptphitwfk dnetivedsg ivirdgnrnl tirrvrkedg glytcqacnv lgcaraetlf iiegaqektn le
```

Extracellular Region of Wildtype Rat VEGFR-2

(SEQ ID NO: 28)
```
asvglpgdslh ppklstqkdi ltilanttlq itcrgqrdld wlwpntprds eervlvtecg dsifcktltv prvvgndtga ykcfyrdtdv ssivyvyvqd hrspfiasys dehgivyite nknktvvipc rgsisnlnvs lcarypekrf vpdgnriswd sekgftipsy misyagmvfc eakindetyq simyivlvvg yriydvvlsp pheielsage klvinctart elnvgldfsw qfpsskhqhk kivnrdvksl pgtvakmfls tltidsvtks dqgeytctay sglmtkknkt fvrvhtkpfi afgsgmkslv eatvgsqvri pvkylsypap dikwyrngrp iesnytmivg deltimevse rdagnytvil tnpismekqs hmvslvvnvp pqigekalis pmdsyqygtm qtltctvyan pplhhiqwyw qleeacsyrp sqtnpytcke wrhvkdfqgg nkievtknqy aliegknktv stiviqaayv salykceain kagrgervis fhvirgpeit vqpatqpter esmslllctad rntfenitwy klgsqatsvh mgesltpvck nldalwklng tvfsnstndi livafqnasl qdqgnyvcsa qdkktkkrhc lvkqlviler mapmitgnle nqtttigeti evvcptsgnp tplitwfkdn etivedsgiv lkdgnrniti rrvrkedggl ytcqacnvlg caraetlfii egvqektnle
```

Extracellular Region of Wildtype Human VEGFR-3 (the seven Ig-like domains are shown in bold)

(SEQ ID NO: 29)
```
ysmtpp tlniteeshv idtgdslsis crgqhplewa wpgaqeapat gdkdsedtgv vrdcegtdar pyckvlllhe vhandtgsyv cyykyikari egttaassyv fvrdfeqpfi nkpdtllvnr kdamwvpclv sipglnvtlr sgssvlwpdg qevvwddrrg mlvstpllhd alylqcettw gdgdflsnpf lvhitgnely diqllprksl ellvgeklvl nctvwaefns gvtfdwdypg kqaergkwvp errsqqthte lssiltihnv sqhdlgsyvc kanngiqrfr estevivhen pfisvewlkg pileatagde lvklpvklaa vpppefgwyk dgkalsgrhs phalvlkevt eastgtytla lwnsaaglrr nislelvvnv ppqihekeas spsiysrhsr qaltctaygv plplsiqwhw
```

-continued

```
rpwtpckmfa qrslrrrqqq dlmpqcrdwr avttqdavnp iesldtwtef vegknktvsk lvignanvsa mykcvvsnkv gqderliyfy vttipdgfti eskpseelle ggpvllscqa dsykyehlrw yrinlstlhd ahgnpllldc knvhlfatpl aasleevapg arhatlslsi prvapehegh yvcevqdrrs hdkhchkkyl svgalearpl tqnitdllvn vsdslemgcl vagahapsiv wykderllee ksgvdladsn qklsiqzvre edagrylcsv cnakgcvnss asvavegsed kgsmeivilv
```

Extracellular Region of Wildtype Mouse VEGFR-3

(SEQ ID NO: 30)
```
ysmtpp tlnitedsyv idtgdslsis crgqhplewt wpgagevltt ggkdsedtry vhdcegtear pyckvillaq thanntgsyh cyykyikari egttaastyv fvrdfkhpfi nkpdtllvnr kdsmwvpclv sipglnitlr sqssalhpdg qevlwddrrg mrvptqllrd alylqcettw gdqnflsnlf vvhitgnely diglypkksm ellvgeklvl nctvwaefds gvtfdwdypg kqaerakwvp errsqqthte lssiltihnv sqndlgpyvc eanngiqrfr estevivhek pfisvewlkg pvleatagde lvklpvklaa ypppefqwyk drkavtgrhn phalvlkevt easagvytla lwnsaaglrq nislelvvnv pphihekeas spsiysrhsr qtltctaygv pqplsvqwhw rpwtpcktfa qrslrrrqqr dgmpqcrdwk evttqdavnp iesldswtef vegknktvsk lviqdanvsa mykcvvvsnkv gqderliyfy vttipdgfsi esepsedple gqsvrlscra dnytyehlrw yrinlstlhd aqgnpllldc knvhlfatpl eanleeaepg arhatlslni prvapedegd yvcevqdrrs qdkhchkkyl svgalearpl tqnitdllvn vsdslemrcp vagahvpsiv wykderllek esgidladsn qrlsiqrvre edagrylcsv cnakgcvnss asvavegsed kgsme
```

Extracellular Region of Wildtype Rat VEGFR-3

(SEQ ID NO: 31)
```
ysmtpp tlnitedsyv idtgdslsis crgqhplewt wrgagevltt ggkdsedtqv vqdcegtear pyckvlslaq thanntgsyy cyykyikari egttaastyv fvrdfeqpfi nkpdtllvnr kdsmwvpclv sipglnitlr sqssvlhpdg qevlwddrrg mrvptlllrd alylqcettw gdqdflsnpf lvhitgnely diglypkksl ellvgeklvl nctvwaefds gvtfdwdypg kqaerakwvp errsqqthte lssiltihnv sqhdlgpyvc eanngiqrfr estevivhek pfisvewlkg pvleatagde mvklpvklaa ypppefqwyk drkavtgrhn phalvlkevt easagvytla lwnsaaglrq nislelvvnv pphihekeas spsiysrhsr qtltcttygv pqplsvqwhw
```

-continued

```
rpwtpcktfa qrslrrrqpr dgmpqcrdwk evttqdavnp iesldtwtes vegknktvsk lviqdanvsa mykcvvfnkv gqderliyfy vttipdgfsi esepsedple gqsvrlscra dnytyehlrw yrinlstlhd aqgnpllldc knvhlfatpl eanleeaepg arhatlslni prvapedegd yvcevqdrrs qdkhchkkyl svgaleaprl tqnitdllvn vrtslemrcp vagahvpsiv wykderllek esgidladsn qrlsiqrvre edagrylcsv cnakgcvnss asvavegsed kgsme
```

In some examples, a soluble VEGF receptor can further include a stabilizing domain (e.g., a Fc domain or a portion of a Fc domain). For example, a stabilizing domain can be an IgG1 Fc domain (e.g., a human wildtype IgG1 Fc domain or a portion thereof). For example, a stabilizing domain can be an IgG2 Fc domain (e.g., a human wildtype IgG2 Fc domain or a portion thereof). For example, a stabilizing domain can be an IgG3 Fc domain (e.g., a human wildtype IgG3 domain or a portion thereof).

Non-limiting examples of human wildtype IgG1 Fc domain, human wildtype IgG2 Fc domain, and human wildtype IgG3 Fc domain are shown below.

```
Human Wildtype IgG1 FC Domain
                                        (SEQ ID NO: 32)
pcpapellgg psvflfppkp kdtlmisrtp evtcvvvdvs hedpevkfnw yvdgvevhna ktkpreeqyn styrvvsvlt vlhqdwlngk eykckvsnka lpapiektis kakgqprepq vytlppsrde ltknqvsltc lvkgfypsdi avewesngqp ennykttppv ldsdgsffly skltvdksrw qqgnvfscsv mhealhnhyt qkslslspgk Human Wildtype IgG2 FC Region
                                        (SEQ ID NO: 33)
vecppcpapp vagpsvflfp pkpkdtlmis rtpevtcvvv dvshedpevq fnwyvdgvev hnaktkpree qfnstfrvvs vltvvhqdwl ngkeykckvs nkglpapiek tisktkgqpr epqvytlpps reemtknqvs ltclvkgfyp sdiavewesn gqpennyktt ppmldsdgsf flyskltvdk srwqqgnvfs csvmhealhn hytqkslsls pgk Human Wildtype IgG3 FC Region
                                        (SEQ ID NO: 34)
tcprcpapel lggpsvflfp pkpkdtlmis rtpevtcvvv dvshedpevq fkwyvdgvev hnaktkpree qfnstfrvvs vltvlhqdwl ngkeykckvs nkalpapiek tisktkgqpr epqvytlpps reemtknqvs ltclvkgfyp sdiavewess gqpennyktt ppmldsdgsf flyskltvdk srwqqgnifs csvmhealhn rftqkslsls pgk
```

In some embodiments, the soluble VEGF receptor is aflibercept (Eylea®). Aflibercept includes portions of human VEGF receptors 1 and 2 extracellular domains fused to the Fc portion of human IgG1 (size ~115 kDa). Aflibercept inhibits the activity of VEGF-A, VEGF-B, and PlGF. Aflibercept has a $K_D$ for VEGF-A of 0.49 pM. See, e.g., WO 2017/218974.

```
Amino Encoding aflibercept
                                        (SEQ ID NO: 12)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQHKKL

VNRDLKTQSGSEMKKFLSTLTIDGVTRSDQGLYTCAASSGLMTKKNSTFV

RVHEKDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPG
```

In some embodiments of a soluble VEGF receptor includes a sequence that is at least 80% identical (e.g., at least 82%, at least 84%, at least 86%, at least 88%, at least 90%, at least 92%, at least 94%, at least 96%, at least 98%, or at least 99%) identical to SEQ ID NO: 12.

In some embodiments of the soluble VEGF receptor includes an extracellular domain that is or includes the sequence of SEQ ID NO: 12, except that it includes one, two, three, four, five, six, seven, eight, nine, ten, eleven, twelve, thirteen, fourteen, or fifteen amino acid substitutions in the sequence of SEQ ID NO: 12.

Additional examples of soluble VEGF receptors are described in, e.g., Kendall et al., PNAS 90: 10705-10709, 1993; Kendall et al., Biochem Biophys Res Commun 226: 324-328, 1996; Failla et al., Int J Mol Sci 19(5):pii. E1306, 2018; and Jung et al., PLoS One 7(9): e44572.

Vectors

Recombinant AAV vectors or "rAAVs" are typically composed of, at a minimum, a transgene or a portion thereof and a regulatory sequence, and optionally 5' and 3' AAV inverted terminal repeats (ITRs). Such a recombinant AAV vector is packaged into a capsid and delivered to a selected target cell (e.g., a cochlear hair cell).

The AAV sequences of the vector typically comprise the cis-acting 5' and 3' ITR sequences (See, e.g., B. J. Carter, in "Handbook of Parvoviruses", ed., P. Tijsser, CRC Press, pp. 155 168, 1990). Typical AAV ITR sequences are about 145 nucleotides in length. In some embodiments, at least 75% of a typical ITR sequence (e.g., at least 80%, at least 85%, at least 90%, or at least 95%) is incorporated into the AAV vector. The ability to modify these ITR sequences is within the skill of the art. (See, e.g., texts such as Sambrook et al., "Molecular Cloning. A Laboratory Manual", 2d ed., Cold Spring Harbor Laboratory, New York, 1989; and K. Fisher et al., *J Virol*. 70:520 532, 1996). In some embodiments, any of the coding sequences described herein is flanked by 5' and 3' AAV ITR sequences in the AAV vectors. The AAV ITR sequences may be obtained from any known AAV, including presently identified AAV types.

AAV vectors as described herein may include any of the regulatory elements described herein (e.g., one or more of a promoter, a polyadenylation (poly(A)) signal sequence, and an IRES).

In some embodiments, the vector(s) is an adenovirus (see, e.g., Dmitriev et al. (1998) *J Virol*. 72: 9706-9713; and Poulin et al., *J Virol* 8: 10074-10086, 2010). In some embodiments, the vector(s) is a retrovirus (see, e.g., Maier et al. (2010) *Future Microbiol* 5: 1507-23).

The vectors provided herein can be of different sizes. The choice of vector that is used in any of the compositions, kits, and methods described herein may depend on the size of the vector.

In some embodiments, the vector(s) can have a total number of nucleotides of up to 10 kb. In some embodiments, the viral vector(s) can have a total number of nucleotides in the range of about 1 kb to about 2 kb, 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 2 kb to about 9 kb, about 2 kb to about 10 kb, about 3 kb to about 4 kb, about 3 kb to about 5 kb, about 3 kb to about 6 kb, about 3 kb to about 7 kb, about 3 kb to about 8 kb, about 3 kb to about 9 kb, about 3 kb to about 10 kb, about 4 kb to about 5 kb, about 4 kb to about 6 kb, about 4 kb to about 7 kb, about 4 kb to about 8 kb, about 4 kb to about 9 kb, about 4 kb to about 10 kb, about 5 kb to about 6 kb, about 5 kb to about 7 kb, about 5 kb to about 8 kb, about 5 kb to about 9 kb, about 5 kb to about 10 kb, about 6 kb to about 7 kb, about 6 kb to about 8 kb, about 6 kb to about 9 kb, about 6 kb to about 10 kb, about 7 kb to about 8 kb, about 7 kb to about 9 kb, about 7 kb to about 10 kb, about 8 kb to about 9 kb, about 8 kb to about 10 kb, or about 9 kb to about 10 kb.

In some embodiments, the vector(s) is a lentivirus and can have a total number of nucleotides of up to 8 kb. In some examples, the lentivirus(es) can have a total number of nucleotides of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 7 kb, about 6 kb to about 8 kb, about 6 kb to about 7 kb, or about 7 kb to about 8 kb.

In some embodiments, the vector(s) is an adenovirus and can have a total number of nucleotides of up to 8 kb. In some embodiments, the adenovirus(es) can have a total number of nucleotides in the range of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 7 kb, about 6 kb to about 8 kb, or about 7 kb to about 8 kb.

In some embodiments, the vector(s) is an adeno-associated virus (AAV vector) and can include a total number of nucleotides of up to 5 kb. In some embodiments, the AAV vector(s) can include a total number of nucleotides in the range of about 1 kb to about 2 kb, about 1 kb to about 3 kb, about 1 kb to about 4 kb, about 1 kb to about 5 kb, about 2 kb to about 3 kb, about 2 kb to about 4 kb, about 2 kb to about 5 kb, about 3 kb to about 4 kb, about 3 kb to about 5 kb, or about 4 kb to about 5 kb.

A variety of different methods known in the art can be used to introduce any of vectors disclosed herein into a mammalian cell (e.g., an inner ear cell, a cochlear inner hair cell). Non-limiting examples of methods for introducing nucleic acid into a mammalian cell include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection.

Any of the vectors described herein can further include a control sequence, e.g., a control sequence selected from the group of a transcription initiation sequence, a transcription termination sequence, a promoter sequence, an enhancer sequence, an RNA splicing sequence, a polyadenylation (polyA) signal, and a Kozak consensus sequence. Non-limiting examples of these control sequences are described herein. In some embodiments, a promoter can be a native promoter, a constitutive promoter, an inducible promoter, and/or a tissue-specific promoter.

Promoters

The term "promoter" means a DNA sequence recognized by enzymes/proteins in a mammalian cell required to initiate the transcription of a specific gene. A promoter typically refers to, e.g., a nucleotide sequence to which an RNA polymerase and/or any associated factor binds and at which transcription is initiated. Non-limiting examples of promoters are described herein. Additional examples of promoters are known in the art.

In some embodiments, a vector (e.g., an adeno-associated virus (AAV) vector) encoding an antibody (e.g., an antibody that binds specifically to VEGF or an antigen-binding antibody fragment thereof,) can include a promoter and/or an enhancer. The vector encoding the antibody or antigen-binding antibody fragment can include any of the promoters and/or enhancers described herein or known in the art.

In some embodiments, the promoter is an inducible promoter, a constitutive promoter, a mammalian cell promoter, a viral promoter, a chimeric promoter, an engineered promoter, a tissue-specific promoter, or any other type of promoter known in the art. In some embodiments, the promoter is a RNA polymerase II promoter, such as a mammalian RNA polymerase II promoter. In some embodiments, the promoter is a RNA polymerase III promoter, including, but not limited to, a H1 promoter, a human U6 promoter, a mouse U6 promoter, or a swine U6 promoter. The promoter will generally be one that is able to promote transcription in an inner hair cell In some examples, the promoter is a cochlea-specific promoter or a cochlea-oriented promoter.

A variety of promoters are known in the art that can be used herein. Non-limiting examples of promoters that can be used herein include: human EF1a, human cytomegalovirus (CMV) (U.S. Pat. No. 5,168,062), human ubiquitin C (UBC), mouse phosphoglycerate kinase 1, polyoma adenovirus, simian virus 40 (SV40), β-globin, β-actin, α-fetoprotein, γ-globin, β-interferon, γ-glutamyl transferase, mouse mammary tumor virus (MMTV), Rous sarcoma virus, rat insulin, glyceraldehyde-3-phosphate dehydrogenase, metallothionein II (MT II), amylase, cathepsin, MI muscarinic receptor, retroviral LTR (e.g. human T-cell leukemia virus HTLV), AAV ITR, interleukin-2, collagenase, platelet-derived growth factor, adenovirus 5 E2, stromelysin, murine MX gene, glucose regulated proteins (GRP78 and GRP94), α-2-macroglobulin, vimentin, MHC class I gene H-2κ b, HSP70, proliferin, tumor necrosis factor, thyroid stimulating hormone α gene, immunoglobulin light chain, T-cell receptor, HLA DQα and DQβ, interleukin-2 receptor, MHC class II, MHC class II HLA-DRα, muscle creatine kinase, prealbumin (transthyretin), elastase I, albumin gene, c-fos, c-HA-ras, neural cell adhesion molecule (NCAM), H2B (TH2B) histone, rat growth hormone, human serum amyloid (SAA), troponin I (TN I), duchenne muscular dystrophy, human immunodeficiency virus, and Gibbon Ape Leukemia Virus (GALV) promoters. Additional examples of promoters are known in the art. See, e.g., Lodish, Molecular Cell Biology, Freeman and Company, New York 2007. In some embodiments, the promoter is the CMV immediate early promoter. In some embodiments, the promoter is a CAG promoter or a CAG/CBA promoter.

The term "constitutive" promoter refers to a nucleotide sequence that, when operably linked with a nucleic acid encoding a protein (e.g., an antibody or an antigen-binding antibody fragment), causes RNA to be transcribed from the nucleic acid in a mammalian cell under most or all physiological conditions.

Examples of constitutive promoters include, without limitation, the retroviral Rous sarcoma virus (RSV) LTR promoter, the cytomegalovirus (CMV) promoter (see, e.g., Boshart et al, *Cell* 41:521-530, 1985), the SV40 promoter, the dihydrofolate reductase promoter, the beta-actin promoter, the phosphoglycerol kinase (PGK) promoter, and the EF1-alpha promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech, and Ariad. Additional examples of inducible promoters are known in the art.

Examples of inducible promoters regulated by exogenously supplied compounds include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, *Proc. Natl. Acad. Sci. U.S.A.* 93:3346-3351, 1996), the tetracycline-repressible system (Gossen et al, *Proc. Natl. Acad. Sci. U.S.A.* 89:5547-5551, 1992), the tetracycline-inducible system (Gossen et al, *Science* 268:1766-1769, 1995, see also Harvey et al, *Curr. Opin. Chem. Biol.* 2:512-518, 1998), the RU486-inducible system (Wang et al, *Nat. Biotech.* 15:239-243, 1997) and Wang et al, *Gene Ther.* 4:432-441, 1997), and the rapamycin-inducible system (Magari et al. *J. Clin. Invest.* 100:2865-2872, 1997).

The term "tissue-specific" promoter refers to a promoter that is active only in certain specific cell types and/or tissues (e.g., transcription of a specific gene occurs only within cells expressing transcription regulatory proteins that bind to the tissue-specific promoter).

In some embodiments, the regulatory sequences impart tissue-specific gene expression capabilities. In some cases, the tissue-specific regulatory sequences bind tissue-specific transcription factors that induce transcription in a tissue-specific manner.

Exemplary tissue-specific promoters include but are not limited to the following: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, an alpha-myosin heavy chain (a-MHC) promoter, and a cardiac Troponin T (cTnT) promoter. Additional exemplary promoters include Beta-actin promoter, hepatitis B virus core promoter (Sandig et al., *Gene Ther.* 3:1002-1009, 1996), alpha-fetoprotein (AFP) promoter (Arbuthnot et al., *Hum. Gene Ther.* 7:1503-1514, 1996), bone osteocalcin promoter (Stein et al., *Mol. Biol. Rep.* 24:185-196, 1997); bone sialoprotein promoter (Chen et al., *J. Bone Miner. Res.* 11:654-664, 1996), CD2 promoter (Hansal et al., *J. Immunol.* 161:1063-1068, 1998); immunoglobulin heavy chain promoter; T cell receptor alpha-chain promoter, neuronal such as neuron-specific enolase (NSE) promoter (Andersen et al., *Cell. Mol. Neurobiol.* 13:503-515, 1993), neurofilament light-chain gene promoter (Piccioli et al., *Proc. Natl. Acad. Sci. U.S.A.* 88:5611-5615, 1991), and the neuron-specific vgf gene promoter (Piccioli et al., *Neuron* 15:373-384, 1995).

In some embodiments, the tissue-specific promoter is a cochlea-specific promoter. In some embodiments, the tissue-specific promoter is a cochlear hair cell-specific promoter. Non-limiting examples of cochlear hair cell-specific promoters include but are not limited to: a ATOH1 promoter, a POU4F3 promoter, a LHX3 promoter, a MYO7A promoter, a MYO6 promoter, a α9ACHR promoter, and a α10ACHR promoter. In some embodiments, the promoter is an cochlear hair cell-specific promoter such as a PRESTIN promoter or an ONCOMOD promoter. See, e.g., Zheng et al., *Nature* 405:149-155, 2000; Tian et al. *Dev. Dyn.* 231:199-203, 2004; and Ryan et al., *Adv. Otorhinolaryngol.* 66: 99-115, 2009.

Enhancers

In some instances, a vector (e.g., an AAV vector) can include an enhancer sequence. The term "enhancer" refers to a nucleotide sequence that can increase the level of transcription of a nucleic acid encoding a protein of interest (e.g., an antibody that binds specifically to VEGF or an antigen-binding antibody fragment thereof, or a soluble VEGF receptor). Enhancer sequences (50-1500 basepairs in length) generally increase the level of transcription by providing additional binding sites for transcription-associated proteins (e.g., transcription factors). In some embodiments, an enhancer sequence is found within an intronic sequence. Unlike promoter sequences, enhancer sequences can act at much larger distance away from the transcription start site (e.g., as compared to a promoter). Non-limiting examples of enhancers include a RSV enhancer, a CMV enhancer, and a SV40 enhancer.

Poly(A) Signal Sequence

In some embodiments, any of the vectors provided herein (e.g., an AAV vector) can include a polyadenylation (poly (A)) signal sequence. Most nascent eukaryotic mRNAs possess a poly(A) tail at their 3' end which is added during a complex process that includes cleavage of the primary transcript and a coupled polyadenylation reaction driven by the poly(A) signal sequence (see, e.g., Proudfoot et al., *Cell* 108:501-512, 2002). The poly(A) tail confers mRNA stability and transferability (Molecular Biology of the Cell, Third Edition by B. Alberts et al., Garland Publishing, 1994). In some embodiments, the poly(A) signal sequence is positioned 3' to the nucleic acid sequence encoding the antibody heavy chain, the antibody light chain, the antigen-binding antibody fragment, or the soluble VEGF receptor.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (e.g., 50, 60, 70, 100, 200, 500, 1000, 2000, 3000, 4000, or 5000) added to the pre-mRNA through the action of an enzyme, polyadenylate polymerase. In higher eukaryotes, the poly(A) tail is added onto transcripts that contain a specific sequence, the polyadenylation (or poly (A)) signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but also can occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, a "poly(A) signal sequence" or "polyadenylation signal sequence" is a sequence that triggers the endonuclease cleavage of an mRNA and the addition of a series of adenosines to the 3' end of the cleaved mRNA.

There are several poly(A) signal sequences that can be used, including those derived from bovine growth hormone (bgh) (Woychik et al., *Proc. Natl. Acad. Sci. U.S.A.* 81(13): 3944-3948, 1984; U.S. Pat. No. 5,122,458), mouse-β-globin, mouse-α-globin (Orkin et al., *EMBO J.* 4(2):453-456, 1985; Thein et al., *Blood* 71(2):313-319, 1988), human collagen, polyoma virus (Batt et al., *Mol. Cell Biol.* 15(9): 4783-4790, 1995), the Herpes simplex virus thymidine kinase gene (HSV TK), IgG heavy-chain gene polyadenylation signal (U.S. 2006/0040354), human growth hormone (hGH) (Szymanski et al., *Mol. Therapy* 15(7):1340-1347, 2007), the group consisting of SV40 poly(A) site, such as the SV40 late and early poly(A) site (Schek et al., *Mol. Cell Biol.* 12(12):5386-5393, 1992).

The poly(A) signal sequence can be AATAAA. The AATAAA sequence may be substituted with other hexanucleotide sequences with homology to AATAAA and that are capable of signaling polyadenylation, including ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, or AATAAG (see, e.g., WO 06/12414).

In some embodiments, the poly(A) signal sequence can be a synthetic polyadenylation site (see, e.g., the pCl-neo expression vector of Promega that is based on Levitt el al, *Genes Dev.* 3(7):1019-1025, 1989). In some embodiments, the poly(A) signal sequence is the polyadenylation signal of soluble neuropilin-1 (sNRP) (AAATAAAATACGAAATG; SEQ ID NO: 11) (see, e.g., WO 05/073384). Additional examples of poly(A) signal sequences are known in the art.

Internal Ribosome Entry Site (IRES)

In some embodiments, a vector (e.g., an adeno-associated virus (AAV) vector) encoding an antibody (e.g., an antibody heavy chain and an antibody light chain), an antigen-binding antibody fragment, or a soluble VEGF receptor can include a polynucleotide internal ribosome entry site (IRES). An IRES sequence is used to produce more than one polypeptide from a single gene transcript. An IRES forms a complex secondary structure that allows translation initiation to occur from any position with an mRNA immediately downstream from where the IRES is located (see, e.g., Pelletier and Sonenberg, *Mol. Cell. Biol.* 8(3):1103-1112, 1988).

There are several IRES sequences known to those in skilled in the art, including those from, e.g., foot and mouth disease virus (FMDV), encephalomyocarditis virus (EMCV), human rhinovirus (HRV), cricket paralysis virus, human immunodeficiency virus (HIV), hepatitis A virus (HAV), hepatitis C virus (HCV), and poliovirus (PV). See e.g., Alberts, Molecular Biology of the Cell, Garland Science, 2002; and Hellen et al., *Genes Dev.* 15(13):1593-612, 2001.

In some embodiments, the IRES sequence that is incorporated into the AAV vector is the foot and mouth disease virus (FMDV) 2A sequence. The Foot and Mouth Disease Virus 2A sequence is a small peptide (approximately 18 amino acids in length) that has been shown to mediate the cleavage of polyproteins (Ryan, M D et al., *EMBO* 4:928-933, 1994; Mattion et al., *J. Virology* 70:8124-8127, 1996; Furler et al., *Gene Therapy* 8:864-873, 2001; and Halpin et al., *Plant Journal* 4:453-459, 1999). The cleavage activity of the 2A sequence has previously been demonstrated in artificial systems including plasmids and gene therapy vectors (AAV and retroviruses) (Ryan et al., *EMBO* 4:928-933, 1994; Mattion et al., *J Virology* 70:8124-8127, 1996; Furler et al., *Gene Therapy* 8:864-873, 2001; and Halpin et al., *Plant Journal* 4:453-459, 1999; de Felipe et al., *Gene Therapy* 6:198-208, 1999; de Felipe et al., *Human Gene Therapy* 11:1921-1931, 2000; and Klump et al., *Gene Therapy* 8:811-817, 2001).

Reporter Sequences

Any of the AAVs provided herein can optionally include a sequence encoding a reporter protein ("a reporter sequence"). Non-limiting examples of reporter sequences include DNA sequences encoding: a beta-lactamase, a beta-galactosidase (LacZ), an alkaline phosphatase, a thymidine kinase, a green fluorescent protein (GFP), a red fluorescent protein, an mCherry fluorescent protein, a yellow fluorescent protein, a chloramphenicol acetyltransferase (CAT), and a luciferase. Additional examples of reporter sequences are known in the art. When associated with regulatory elements which drive their expression, the reporter sequence can provide signals detectable by conventional means, including enzymatic, radiographic, colorimetric, fluorescence, or other spectrographic assays; fluorescent activating cell sorting (FACS) assays; immunological assays (e.g., enzyme linked immunosorbent assay (ELISA), radioimmunoassay (RIA), and immunohistochemistry).

In some embodiments, the reporter sequence is the LacZ gene, and the presence of a vector carrying the LacZ gene in a mammalian cell (e.g., a cochlear hair cell) is detected by assays for beta-galactosidase activity. When the reporter is a fluorescent protein (e.g., green fluorescent protein) or luciferase, the presence of a vector carrying the fluorescent protein or luciferase in a mammalian cell (e.g., a cochlear hair cell) may be measured by fluorescent techniques (e.g., fluorescent microscopy or FACS) or light production in a luminometer (e.g., a spectrophotometer or an IVIS imaging instrument). In some embodiments, the reporter sequence can be used to verify the tissue-specific targeting capabilities and tissue-specific promoter regulatory activity of any of the vectors described herein.

Flanking Regions Untranslated Regions (UTRs)

In some embodiments, any of the adeno-associated virus (AAV) vectors can include an untranslated region, such as a 5' UTR or a 3' UTR.

Untranslated regions (UTRs) of a gene are transcribed but not translated. The 5' UTR starts at the transcription start site and continues to the start codon but does not include the start codon. The 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into any of the vectors, compositions, kits, or methods as described herein to enhance the expression of an antibody (e.g., an antibody that binds specifically to VEGF), an antigen-binding antibody fragment (e.g., an antigen-binding fragment that binds specifically to VEGF), or a soluble VEGF receptor.

Natural 5' UTRs include a sequence that plays a role in translation initiation. They harbor signatures like Kozak sequences, which are commonly known to be involved in the process by which the ribosome initiates translation of many genes. Kozak sequences have the consensus sequence CCR (A/G)CCAUGG, where R is a purine (A or G) three bases upstream of the start codon (AUG), and the start codon is followed by another "G". The 5' UTRs have also been known to form secondary structures that are involved in elongation factor binding.

In some embodiments, a 5' UTR is included in any of the vectors described herein. Non-limiting examples of 5' UTRs, including those from the following genes: albumin, serum amyloid A, Apolipoprotein A/B/E, transferrin, alpha fetoprotein, erythropoietin, and Factor VIII, can be used to enhance expression of a nucleic acid molecule, such as a mRNA.

In some embodiments, a 5' UTR from a mRNA that is transcribed by a cell in the cochlea can be included in any of the vectors, compositions, kits, and methods described herein.

3' UTRs are known to have stretches of adenosines and uridines (in the RNA form) or thymidines (in the DNA form) embedded in them. These AU-rich signatures are particularly prevalent in genes with high rates of turnover. Based on their sequence features and functional properties, the AU-rich elements (AREs) can be separated into three classes (Chen et al., *Mol. Cell. Biol.* 15:5777-5788, 1995; Chen et al., *Mol. Cell Biol.* 15:2010-2018, 1995): Class I AREs contain several dispersed copies of an AUUUA motif within U-rich regions. For example, c-Myc and MyoD mRNAs contain class I AREs. Class II AREs possess two or more overlapping UUAUUUA(U/A) (U/A) nonamers. GM-CSF and TNF-alpha mRNAs are examples that contain class II AREs. Class III AREs are less well defined. These U-rich regions do not contain an AUUUA motif. Two well-studied examples of this class are c-Jun and myogenin mRNAs.

Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

In some embodiments, the introduction, removal, or modification of 3' UTR AREs can be used to modulate the stability of an mRNA encoding a protein of interest (e.g., any antibody described herein, any antigen-binding antibody fragment described herein, or any soluble VEGF receptor described herein). In other embodiments, AREs can be removed or mutated to increase the intracellular stability and thus increase translation and production of a protein of interest (e.g., any antibody described herein, any antigen-binding antibody fragment described herein, or any soluble VEGF receptor described herein).

In other embodiments, non-ARE sequences may be incorporated into the 5' or 3' UTRs. In some embodiments, introns or portions of intron sequences may be incorporated into the flanking regions of the polynucleotides in any of the vectors, compositions, kits, and methods provided herein. Incorporation of intronic sequences may increase protein production as well as mRNA levels.

Fc Mutations that Decrease the Half-Life of an Antibody, Antigen-Binding Antibody Fragment, or a Soluble VEGF Receptor in a Mammal Any of the antibodies, antigen-binding antibody fragments, or soluble VEGF receptors described herein can include one or more (e.g., two, three, four, five, six, seven, eight, nine, or ten) amino acid substitutions in the Fc region that decrease the half-life of the antibody, the antigen-binding antibody fragment, or soluble VEGF receptor in a mammal, e.g., as compared to the half-life of an otherwise identical antibody, antigen-binding antibody fragment, or soluble VEGF receptor not including at least one of the one or more amino acid substitutions in the Fc region. Methods for determining the half-life of an antibody, antigen-binding antibody fragment, or soluble VEGF receptor in a mammal are well-known in the art.

Non-limiting examples of point mutations in a Fc mutation that can decrease the half-life of an antibody, an antigen-binding antibody fragment, or soluble VEGF receptor are described in Leabman et al., *MAbs* 5(6):896-903, 2013.

Methods

Also provided herein are methods that include introducing into an inner ear of a mammal a therapeutically effective amount of an adeno-associated virus (AAV) vector that includes a nucleotide sequence encoding (a) a polypeptide including an antibody heavy chain variable domain (e.g., any of the exemplary antibody heavy chain variable domains described herein) operably linked to a signal peptide (e.g., any of the signal peptides described herein) and a polypeptide including an antibody light chain variable domain (e.g., any of the exemplary antibody light chain variable domains described herein) operably linked to a signal peptide (e.g., any of the signal peptides described herein); (b) a polypeptide including an antigen-binding antibody fragment (e.g., a scFv) (e.g., any of the exemplary antigen-binding antibody fragments described herein) operably linked to a signal peptide (e.g., any of the signal peptides described herein), or (c) a soluble VEGF receptor (e.g., any of the soluble VEGF receptors described herein) operably linked to a signal peptide (e.g., any of the signal peptides described herein).

Also provided herein are methods for increasing the level of an antibody or an antigen-binding antibody fragment in an inner ear of a mammal in need thereof, that include: introducing into the inner ear of the mammal a therapeutically effective amount of an AAV vector that includes a nucleotide sequence encoding (a) a polypeptide including an antibody heavy chain variable domain (e.g., any of the antibody heavy chain variable domains described herein) operably linked to a signal peptide and a polypeptide including an antibody light chain variable domain (e.g., any of the antibody light chain variable domains described herein) operably linked to a signal peptide; or (b) a polypeptide including an antigen-binding antibody fragment (e.g., a scFv) (e.g., any of the exemplary antigen-binding antibody fragments described herein) operably linked to a signal peptide (e.g., any of the exemplary signal peptides described herein); where the introducing results in an increase (e.g., a 1% to 400% increase (or any of the subranges of this range described herein), or at least a 1%, at least a 10%, at least a 20%, at least a 30%, at least a 40%, at least a 50%, at least a 60%, at least a 70%, at least a 80%, at least a 90%, at least a 100%, at least a 150%, at least a 200%, at least a 250%, at least a 300%, at least a 350%, at least a 400%, at least a 450%, at least a 500%, at least a 550%, at least a 600%, at least a 650%, at least a 700%, at least a 750%, at least a 800%, at least a 850%, at least a 900%, at least a 950%, at least a 1000%, at least a 1100%, at least a 1200%, at least a 1300%, at least a 1400%, at least a 1500%, at least a 1600%, at least a 1700%, at least a 1800%, at least a 1900%, or at least a 2000% increase) in the level of the antibody or the antigen-binding antibody fragment in the inner ear of the mammal, e.g., as compared to the level of the antibody or the antigen-binding antibody fragment in the inner ear of the mammal prior to the administration.

Also provided herein are methods for increasing the level of a soluble VEGF receptor that include: introducing into the inner ear of the mammal a therapeutically effective amount of an AAV vector that includes a nucleotide sequence encoding a soluble VEGF receptor (e.g., any of the soluble VEGF receptors described herein) operably linked to a signal peptide (e.g., any of the signal peptides described herein); where the introducing results in an increase (e.g., a 1% to 400% increase (or any of the subranges of this range described herein), or at least a 1%, at least a 10%, at least a 20%, at least a 30%, at least a 40%, at least a 50%, at least a 60%, at least a 70%, at least a 80%, at least a 90%, at least a 100%, at least a 150%, at least a 200%, at least a 250%, at least a 300%, at least a 350%, at least a 400%, at least a 450%, at least a 500%, at least a 550%, at least a 600%, at least a 650%, at least a 700%, at least a 750%, at least a 800%, at least a 850%, at least a 900%, at least a 950%, at least a 1000%, at least a 1100%, at least a 1200%, at least a 1300%, at least a 1400%, at least a 1500%, at least a 1600%, at least a 1700%, at least a 1800%, at least a 1900%, or at least a 2000% increase) in the level of the soluble VEGF receptor in the inner ear of the mammal, e.g., as compared to the level of the soluble VEGF receptor in the inner ear of the mammal prior to the administration.

Also provided herein are methods for treating an inner ear disorder in a mammal in need thereof that include introducing into the inner ear of the mammal a therapeutically effective amount of an AAV vector that comprises a nucleotide sequence encoding: (a) a polypeptide including an antibody heavy chain variable domain (e.g., e.g., any of the antibody heavy chain variable domains described herein) operably linked to a signal peptide (e.g., any of the signal peptides described herein) and a polypeptide comprising an antibody light chain variable domain (e.g., any of the antibody light chain variable domains described herein) operably linked to a signal peptide (e.g., any of the signal peptides described herein); (b) a polypeptide including an antigen-binding antibody fragment (e.g., any of the exemplary antigen-binding antibody fragments described herein) linked to a signal peptide (e.g., any of the signal peptides described herein); or (c) a soluble VEGF receptor (e.g., any of the soluble VEGR receptors described herein) operably linked to a signal peptide (e.g., any of the signal peptides described herein), where the introducing results in the treatment of the inner ear disorder in the mammal. In some embodiments, treatment of an inner ear disorder results in a reduction (e.g., a 1% to 100% reduction, or any of the subranges of this range described herein) in the severity, frequency, or number of symptoms of an inner ear disorder in a mammal following the introducing as compared to before the introducing. In some embodiments, treatment of any inner ear disorder results in an increase (e.g., a 1% to 400% increase, or any of the subranges of this range described herein) in the hearing (e.g., one or more metrics of hearing) of the mammal following the introducing as compared to before the introducing.

In some embodiments of any of these methods, the antibody or the antigen-binding antibody fragment, or the soluble VEGF receptor, binds specifically to a vascular endothelial growth factor (VEGF) (e.g., one of more of VEGF-A, VEGF-B, VEGF-C, and VEGF-D, e.g., one or more of human VEGF-A, human VEGF-B, human VEGF-C, and human VEGF-D). In some embodiments of any of these methods, the AAV vector further includes one or both of a promoter and a Kozak sequence that are operably linked to the sequence encoding the antibody or the antigen-binding antibody fragment. In some embodiments wherein the AAV vector comprises a promoter selected from the group consisting of: an inducible promoter, a constitutive promoter, and a tissue-specific promoter. In some embodiments of any of these methods, the AAV vector further includes a polyadenylation signal sequence. In some embodiments of any of these methods, the mammal is a human. In some embodiments of any of these methods, the mammal (e.g., the human) has been identified as having an inner ear disorder. In some embodiments of any of these methods, the mammal (e.g., the human) has previously been diagnosed as having an inner ear disorder. In some embodiments of any of these methods, the vector includes a nucleic acid sequence encoding a polypeptide comprising an antibody heavy chain and an antibody light chain. In some embodiments of any of these methods, the vector includes a nucleic acid sequence encoding an antigen-binding antibody fragment. In some embodiments of any of these methods, the vector include a nucleic acid sequence encoding a soluble VEGF receptor operably linked to a signal peptide.

Also provided herein are methods of reducing a VEGF activity (e.g., one or more of VEGF-A, VEGF-B, VEGF-C, and VEGF-D, e.g., one or more of human VEGF-A, human VEGF-B, human VEGF-C, and human VEGF-D) in an inner ear of a mammal in need thereof that include: introducing into the inner ear of the mammal a therapeutically effective amount of an AAV vector that includes a nucleotide sequence encoding (a) a polypeptide including an antibody heavy chain variable domain (e.g., any of the antibody heavy chain variable domains described herein) operably linked to a signal peptide (e.g., any of the signal peptides described herein) and a polypeptide including an antibody light chain variable domain (e.g., any of the antibody light chain variable domains described herein) operably linked to a signal peptide (e.g., any of the signal peptides described herein); (b) a polypeptide including an antigen-binding antibody fragment (e.g., a Fab or a scFv) (e.g., any of the antigen-binding antibody fragments described herein) operably linked to a signal peptide (e.g., any of the signal peptides described herein); or (c) a soluble VEGF receptor (e.g., any of the soluble VEGF receptors described herein) operably linked to a signal peptide (e.g., any of the signal peptides described herein), where the polypeptide of (a) includes an antibody that binds specifically to a VEGF and reduces a VEGF activity, the polypeptide of (b) includes an antigen-binding antibody fragment that binds specifically to a VEGF and reduces a VEGF activity, or the soluble VEGF receptor of (c) binds specifically to one or more VEGF proteins and reduces the activity of the one or more VEGF proteins; and where the introducing results in a reduction (e.g., a 1% to 100% reduction, or any of the subranges of this range described herein) in a VEGF activity (e.g., an activity of one or more of VEGF-A, VEGF-B, VEGF-C, and VEGF-D, e.g., one or more human VEGF-A, human VEGF-B, human VEGF-C, and human VEGF-D) in the inner ear of the mammal, e.g., as compared to the VEGF activity in the mammal prior to the introducing. A reduction in a VEGF activity in a mammal can be detected using any of the exemplary methods described herein.

Also provided herein are methods of treating acoustic neuroma, vestibular schwannoma, or neurofibromatosis type II (NF2) in an inner ear of a mammal that include: introducing into the inner ear of the mammal a therapeutically effective amount of an AAV vector that includes a nucleotide sequence encoding (a) a polypeptide including an antibody heavy chain variable domain (e.g., any of the antibody heavy chain variable domains described herein) operably linked to a signal peptide (e.g., any of the signal peptides described herein) and a polypeptide including an antibody light chain variable domain (e.g., any of the antibody light chain variable domains described herein) operably linked to a signal peptide (e.g., any of the signal peptides described herein); (b) a polypeptide including an antigen-binding antibody fragment (e.g., a Fab or a scFv) (e.g., any of the antigen-binding antibody fragments described herein) operably linked to a signal peptide (e.g., any of the signal peptides described herein), or (c) a soluble VEGF receptor (e.g., any of the soluble VEGF receptors described herein) operably linked to a signal peptide (e.g., any of the signal peptides described herein); where the polypeptide of (a) encodes an antibody that binds specifically to a VEGF (e.g., one or more of VEGF-A, VEGF-B, VEGF-C, and VEGF-D, e.g., one or more of human VEGF-A, human VEGF-B, human VEGF-C, and human VEGF-D) and reduces the VEGF activity, the polypeptide of (b) encodes an antigen-binding antibody fragment that binds specifically to a VEGF (e.g., one or more of VEGF-A, VEGF-B, VEGF-C, and VEGF-D, e.g., one or more of human VEGF-A, human VEGF-B, human VEGF-C, and human VEGF-D) and reduces the VEGF activity, or the soluble VEGF receptor of (c) binds to specifically to one or more of VEGF-A, VEGF-B, VEGF-C, and VEGF-D (e.g., one or more of human VEGF-A, human VEGF-B, human VEGF-C, and human VEGF-D) and where the introducing results in treatment of acoustic neuroma, vestibular schwannoma, or neurofibromatosis type II (NF2) in the inner ear of the mammal. As described herein, successful treatment of one or more of an acoustic neuroma, vestibular schwannoma, or neurofibromatosis type II can be detected by observing a reduction (e.g., a 1% to 100% decrease, or any of the subranges of this range described herein) in the number, severity, or frequency of one or more symptoms of an acoustic neuroma, vestibular schwannoma, or neurofibromatosis type II, respectively, in the mammal, e.g., as compared to before the introducing step.

In some embodiments of any of these methods, the vector includes a nucleic acid sequence encoding a polypeptide encoding an antibody heavy chain variable domain (e.g., any of the antibody heavy chains described herein) and an antibody light chain variable domain (e.g., any of the antibody light chain variable domains described herein). In some embodiments of any of these methods, the vector includes a nucleic acid sequence encoding a polypeptide comprising an antigen-binding antibody fragment (e.g., any of the antigen-binding antibody fragments described herein). In some embodiments of any of these methods, the vector includes a nucleic acid sequence encoding a soluble VEGF receptor (e.g., any of the soluble VEGF receptors described herein) operably linked to a signal peptide (e.g., any of the signal peptides described herein). In some embodiments of any of these methods, the AAV vector further includes one or both of a promoter and a Kozak sequence that are operably linked to the sequence encoding the antibody or the antigen-binding antibody fragment. In some embodiments, the AAV vector comprises a promoter, where the promoter is selected from the group consisting of: an inducible promoter, a constitutive promoter, or a tissue-specific promoter. In some embodiments, the AAV vector further includes a polyadenylation signal sequence. In some embodiments of any of these methods, the mammal is a human. In some embodiments of any of these methods, the mammal (e.g., the human) has been identified as having an inner ear disorder. In some embodiments of any of these methods, the mammal (e.g., the human) has previously been diagnosed as having an inner ear disorder. In some embodiments of any of these methods, the mammal (e.g., the human) has been identified or diagnosed as having drug-induced hearing loss. In some embodiments of any of these methods, the mammal (e.g., the human) has been identified or diagnosed as having age-related hearing loss.

In some embodiments, the antibody or antigen-binding fragment thereof includes a Fc region that includes one or more point mutations that decrease the half-life of the antibody or antigen-binding antibody fragment in vivo.

In some embodiments of any of these methods, two or more doses of any of the adeno-associated virus (AAV) vectors described herein are introduced or administered into the inner ear of the mammal or subject. Some embodiments of any of these methods can include introducing or administering a first dose of the adeno-associated virus (AAV) vectors into the inner ear of the mammal or subject, assessing hearing function of the mammal or subject following the introducing or the administering of the first dose, and administering an additional dose of the adeno-associated virus (AAV) vector into the inner ear of the mammal or subject found not to have a hearing function within a normal range (e.g., as determined using any test for hearing known in the art).

In some embodiments of any of the methods described herein, the adeno-associated virus (AAV) vectors can be formulated for intra-cochlear administration. In some embodiments of any of the methods described herein, the adeno-associated virus (AAV) vectors described herein can be administered via intra-cochlear administration or local administration. In some embodiments of any of the methods described herein, the adeno-associated virus (AAV) vectors are administered through the use of a medical device (e.g., any of the exemplary medical devices described herein).

In some embodiments, intra-cochlear administration can be performed using any of the methods described herein or known in the art. For example, an adeno-associated virus (AAV) vector can be administered or introduced into the cochlea using the following surgical technique: first using visualization with a 0 degree, 2.5-mm rigid endoscope, the external auditory canal is cleared and a round knife is used to sharply delineate an approximately 5-mm tympanomeatal flap. The tympanomeatal flap is then elevated and the middle ear is entered posteriorly. The chorda tympani nerve is identified and divided, and a currette is used to remove the scutal bone, exposing the round window membrane. To enhance apical distribution of the administered or introduced adeno-associated virus (AAV) vector, a surgical laser may be used to make a small 2-mm fenestration in the oval window to allow for perilymph displacement during trans-round window membrane infusion of the adeno-associated virus (AAV) vectors. The microinfusion device is then primed and brought into the surgical field. The device is maneuvered to the round window, and the tip is seated within the bony round window overhang to allow for penetration of the membrane by the microneedle(s). The footpedal is engaged to allow for a measured, steady infusion of the adeno-associated virus (AAV) vectors. The device is then withdrawn and the round window and stapes foot plate are sealed with a gelfoam patch.

In some embodiments of any of the methods described herein, the subject or mammal is a rodent, a non-human primate, or a human. In some embodiments of any of the methods described herein, the subject or mammal is an adult, a teenager, a juvenile, a child, a toddler, an infant, or a newborn. In some embodiments of any of the methods described herein, the subject or mammal is 1-5, 1-10, 1-20, 1-30, 1-40, 1-50, 1-60, 1-70, 1-80, 1-90, 1-100, 1-110, 2-5, 2-10, 10-20, 20-30, 30-40, 40-50, 50-60, 60-70, 70-80, 80-90, 90-100, 100-110, 10-30, 10-40, 10-50, 10-60, 10-70, 10-80, 10-90, 10-100, 10-110, 20-40, 20-50, 20-60, 20-70, 20-80, 20-90, 20-100, 20-110, 30-50, 30-60, 30-70, 30-80, 30-90, 30-100, 40-60, 40-70, 40-80, 40-90, 40-100, 50-70, 50-80, 50-90, 50-100, 60-80, 60-90, 60-100, 70-90, 70-100, 70-110, 80-100, 80-110, or 90-110 years of age. In some embodiments of any of the methods described herein, the subject or mammal is 1, 2, 3, 4, 5, 6, 7, 8, 9, 10, or 11 months of age.

In some embodiments of any of the methods described herein, the subject or mammal has or is at risk of developing hearing loss (e.g., drug-induced hearing loss). In some embodiments of any of the methods described herein, the subject or mammal has been previously identified as having a mutation in a VEGF gene.

In some embodiments, successful treatment of hearing loss (e.g., drug-induced hearing loss) can be determined in a subject using any of the conventional functional hearing tests known in the art. Non-limiting examples of functional hearing tests are various types of audiometric assays (e.g., pure-tone testing, speech testing, test of the middle ear, auditory brainstem response, and otoacoustic emissions).

Methods for introducing any of the adeno-associated virus (AAV) vectors described herein into a mammalian cell are known in the art (e.g., via lipofection or through the use of a viral vector, e.g., any of the viral vectors described herein).

Pharmaceutical Compositions and Kits

In some embodiments, any of the compositions described herein can further include one or more agents that promote the entry of a nucleic acid or any of the vectors described herein into a mammalian cell (e.g., a liposome or cationic lipid). In some embodiments, any of the vectors described herein can be formulated using natural and/or synthetic polymers. Non-limiting examples of polymers that may be included in any of the compositions described herein can include, but are not limited to, DYNAMIC POLYCONJU-GATE® (Arrowhead Research Corp., Pasadena, Calif), formulations from Mirus Bio (Madison, Wis.) and Roche Madison (Madison, Wis.), PhaseRX polymer formulations such as, without limitation, SMARTT POLYMER TECHNOLOGY® (PhaseRX, Seattle, Wash.), DMRI/DOPE, poloxamer, VAXFECTIN® adjuvant from Vical (San Diego, Calif), chitosan, cyclodextrin from Calando Pharmaceuticals (Pasadena, Calif), dendrimers and poly (lactic-co-glycolic acid) (PLGA) polymers, RONDEL™ (RNAi/Oligonucleotide Nanoparticle Delivery) polymers (Arrowhead Research Corporation, Pasadena, Calif.), and pH responsive co-block polymers, such as, but not limited to, those produced by PhaseRX (Seattle, Wash.). Many of these polymers have demonstrated efficacy in delivering oligonucleotides in vivo into a mammalian cell (see, e.g., deFougerolles, *Human Gene Ther.* 19:125-132, 2008; Rozema et al., *Proc. Natl. Acad. Sci. U.S.A.* 104:12982-12887, 2007; Rozema et al., *Proc. Natl. Acad. Sci. U.S.A.* 104:12982-12887, 2007; Hu-Lieskovan et al., *Cancer Res.* 65:8984-8982, 2005; Heidel et al., *Proc. Natl. Acad. Sci. U.S.A.* 104:5715-5721, 2007).

Any of the compositions described herein can be, e.g., a pharmaceutical composition. A pharmaceutical composition can include any of the compositions described herein and one or more pharmaceutically or physiologically acceptable carriers, diluents, or excipients. Such compositions may comprise one or more buffers, such as neutral-buffered saline, phosphate-buffered saline, and the like; one or more carbohydrates, such as glucose, mannose, sucrose, and dextran; mannitol; one or more proteins, polypeptides, or amino acids, such as glycine; one or more antioxidants; one or more chelating agents, such as EDTA or glutathione; and/or one or more preservatives.

In some embodiments, the composition includes a pharmaceutically acceptable carrier (e.g., phosphate buffered saline, saline, or bacteriostatic water). Upon formulation, solutions will be administered in a manner compatible with the dosage formulation and in such amount as is therapeutically effective. The formulations are easily administered in a variety of dosage forms such as injectable solutions, injectable gels, drug-release capsules, and the like.

As used herein, the term "pharmaceutically acceptable carrier" includes solvents, dispersion media, coatings, antibacterial agents, antifungal agents, and the like that are compatible with pharmaceutical administration. Supplementary active compounds can also be incorporated into any of the compostions described herein.

In some embodiments, a single dose of any of the compositions described herein can include a total sum amount of the at least two different vectors of at least 1 ng, at least 2 ng, at least 4 ng, about 6 ng, about 8 ng, at least 10 ng, at least 20 ng, at least 30 ng, at least 40 ng, at least 50 ng, at least 60 ng, at least 70 ng, at least 80 ng, at least 90 ng, at least 100 ng, at least 200 ng, at least 300 ng, at least 400 ng, at least 500 ng, at least 1 µg, at least 2 µg, at least 4 µg, at least 6 µg, at least 8 µg, at least 10 µg, at least 12 µg, at least 14 µg, at least 16 µg, at least 18 µg, at least 20 µg, at least 22 µg, at least 24 µg, at least 26 µg, at least 28 µg, at least 30 µg at least 32 µg, at least 34 µg, at least 36 µg, at least 38 µg, at least 40 µg, at least 42 µg, at least 44 µg, at least 46 µg, at least 48 µg, at least 50 µg, at least 52 µg, at least 54 µg, at least 56 µg, at least 58 µg, at least 60 µg, at least 62 µg, at least 64 µg, at least 66 µg, at least 68 µg, at least 70 µg, at least 72 µg, at least 74 µg, at least 76 µg, at least 78 µg, at least 80 µg, at least 82 µg, at least 84 µg, at least 86 µg, at least 88 µg, at least 90 µg, at least 92 µg, at least 94 µg, at least 96 µg, at least 98 µg, at least 100 µg, at least 102 µg, at least 104 µg, at least 106 µg, at least 108 µg, at least 110 µg, at least 112 µg, at least 114 µg, at least 116 µg, at least 118 µg, at least 120 µg, at least 122 µg, at least 124 µg, at least 126 µg, at least 128 µg, at least 130 µg at least 132 µg, at least 134 µg, at least 136 µg, at least 138 µg, at least 140 µg, at least 142 µg, at least 144 µg, at least 146 µg, at least 148 µg, at least 150 µg, at least 152 µg, at least 154 µg, at least 156 µg, at least 158 µg, at least 160 µg, at least 162 µg, at least 164 µg, at least 166 µg, at least 168 µg, at least 170 µg, at least 172 µg, at least 174 µg, at least 176 µg, at least 178 µg, at least 180 µg, at least 182 µg, at least 184 µg, at least 186 µg, at least 188 µg, at least 190 µg, at least 192 µg, at least 194 µg, at least 196 µg, at least 198 µg, or at least 200 µg, e.g., in a buffered solution.

The compositions provided herein can be, e.g., formulated to be compatible with their intended route of administration. A non-limiting example of an intended route of administration is local administration (e.g., intra-cochlear administration). In some embodiments, the therapeutic compositions are formulated to include a lipid nanoparticle. In some embodiments, the therapeutic compositions are formulated to include a polymeric nanoparticle. In some embodiments, the therapeutic compositions are formulated to comprise a mini-circle DNA. In some embodiments, the therapeutic compositions are formulated to comprise a CELiD DNA. In some embodiments, the therapeutic compositions are formulated to comprise a synthetic perilymph solution. An exemplary synthetic perilymph solution includes 20-200 mM NaCl; 1-5 mM KCl; 0.1-10 mM $CaCl_2$; 1-10 mM glucose; 2-50 mM HEPES, having a pH of between about 6 and about 9.

Also provided are kits including any of the compositions described herein. In some embodiments, a kit can include a solid composition (e.g., a lyophilized composition including the at least two different vectors described herein) and a liquid for solubilizing the lyophilized composition. In some embodiments, a kit can include a pre-loaded syringe including any of the compositions described herein.

In some embodiments, the kit includes a vial comprising any of the compositions described herein (e.g., formulated as an aqueous composition, e.g., an aqueous pharmaceutical composition).

In some embodiments, the kits can include instructions for performing any of the methods described herein.

Devices and Surgical Methods

Provided herein are therapeutic delivery systems for treating hearing loss (e.g., acoustic neuromas/vestibular schwannomas and associated-hearing loss). In one aspect, the therapeutic delivery systems include i) a medical device capable of creating one or a plurality of incisions in a round window membrane of an inner ear of a human subject in need thereof, and ii) an effective dose of a composition (e.g., any of the compositions described herein). In some embodiments, the medical device includes a plurality of micro-needles.

Also provided herein are surgical methods for treatment of hearing loss (e.g., acoustic neuromas/vestibular schwannomas and associated-hearing loss). In some embodiments, the methods include the steps of: introducing into a cochlea of a human subject a first incision at a first incision point; and administering intra-cochlearly a therapeutically effective amount of any of the compositions provided herein. In some embodiments, the composition is administered to the subject at the first incision point. In some embodiments, the composition is administered to the subject into or through the first incision.

In some embodiments of any of the methods described herein, any of the compositions described herein is administered to the subject into or through the cochlea oval window membrane. In some embodiments of any of the methods described herein, any of the compositions described herein is administered to the subject into or through the cochlea round window membrane. In some embodiments of any of the methods described herein, the composition is administered using a medical device capable of creating a plurality of incisions in the round window membrane. In some embodiments, the medical device includes a plurality of micro-needles. In some embodiments, the medical device includes a plurality of micro-needles including a generally circular first aspect, where each micro-needle has a diameter of at least about 10 microns. In some embodiments, the medical device includes a base and/or a reservoir capable of holding the composition. In some embodiments, the medical device includes a plurality of hollow micro-needles individually including a lumen capable of transferring the composition. In some embodiments, the medical device includes a means for generating at least a partial vacuum.

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations that become evident as a result of the teaching provided herein.

Without further description, it is believed that one of ordinary skill in the art can, using the preceding description and the following illustrative examples, make and utilize the compositions of the present invention and practice the claimed methods. The following working examples specifically point out various aspects of the present invention, and are not to be construed as limiting in any way the remainder of the disclosure.

EXAMPLES

Example 1. Construction of Viral Vectors

Four different recombinant AAV vectors were generated and are shown in FIGS. 1A-D.

The vector in FIG. 1A is an exemplary AAV vector of 4474 bp (SEQ ID NO: 35) that includes the following sub-sequences going in the 5' to 3' direction:

```
CCTGCAGGCAGCTGCGCGCTCGCTCGCTCACTGAGGCCGCCCGGGCGTCG

GGCGACCTTTGGTCGCCCGGCCTCAGTGAGCGAGCGAGCGCGCAGAGAGG

GAGTGGCCAACTCCATCACTAGGGGTTCCTGCGGCCGCACGCGT(5'

ITR; SEQ ID NO: 36);

GACATTGATTATTGACTAGTTATTAATAGTAATCAATTACGGGGTCATTA

GTTCATAGCCCATATATGGAGTTCCGCGTTACATAACTTACGGTAAATGG

CCCGCCTGGCTGACCGCCCAACGACCCCCGCCCATTGACGTCAATAATGA

CGTATGTTCCCATAGTAACGCCAATAGGGACTTTCCATTGACGTCAATGG

GTGGACTATTTACGGTAAACTGCCCACTTGGCAGTACATCAAGTGTATCA

TATGCCAAGTACGCCCCCTATTGACGTCAATGACGGTAAATGGCCCGCCT

GGCATTATGCCCAGTACATGACCTTATGGGACTTTCCTACTTGGCAGTAC

ATCTACGTATTAGTCATCGCTATTACCATGGGTCGAGGTGAGCCCCACGT

TCTGCTTCACTCTCCCCATCTCCCCCCCTCCCCACCCCCAATTTTGTAT

TTATTTATTTTTTAATTATTTTTGTGCAGCGATGGGGGCGGGGGGGGGGG

GGCGCGCGCCAGGCGGGCGGGCGGGCGAGGGCGGGCGGGCGAGG

CGGAGAGGTGCGGCGGCAGCCAATCAGAGCGGCGCGCTCCGAAAGTTTCC

TTTTATGGCGAGGCGGCGGCGGCGGCGGCCCTATAAAAAGCGAAGCGCGC
```

GGCGGGCGGGAGTCGCTGCGTTGCCTTCGCCCCGTGCCCGCTCCGCGCC
GCCTCGCGCCGCCCGCCCCGGCTCTGACTGACCGCGTTACTCCCACAGGT
GAGCGGGCGGGACGGCCCTTCTCCTCCGGGCTGTAATTAGCGCTTGGTTT
AATGACGGCTCGTTTCTTTTCTGTGGCTGCGTGAAAGCCTTAAAGGGCTC
CGGGAGGGCCCTTTGTGCGGGGGGAGCGGCTCGGGGGGTGCGTGCGTGT
GTGTGTGCGTGGGGAGCGCCGCGTGCGGCCCGCGCTGCCCGGCGGCTGTG
AGCGCTGCGGGCGCGGCGCGGGGCTTTGTGCGCTCCGCGTGTGCGCGAGG
GGAGCGCGGCCGGGGGCGGTGCCCCGCGGTGCGGGGGGGCTGCGAGGGGA
ACAAAGGCTGCGTGCGGGGTGTGTGCGTGGGGGGGTGAGCAGGGGGTGTG
GGCGCGGCGGTCGGGCTGTAACCCCCCCCTGCACCCCCCTCCCCGAGTTG
CTGAGCACGGCCCGGCTTCGGGTGCGGGGCTCCGTGCGGGGCGTGGCGCG
GGGCTCGCCGTGCCGGGCGGGGGGTGGCGGCAGGTGGGGGTGCCGGGCGG
GGCGGGGCCGCCTCGGGCCGGGGAGGGCTCGGGGAGGGGCGCGGCGGCC
CCCGGAGCGCCGGCGGCTGTCGAGGCGCGGCGAGCCGCAGCCATTGCCTT
TTATGGTAATCGTGCGAGAGGGCGCAGGGACTTCCTTTGTCCCAAATCTG
TGCGGAGCCGAAATCTGGGAGGCGCCGCCGCACCCCCTCTAGCGGGCGCG
GGGCGAAGCGGTGCGGCGCCGGCAGGAAGGAAATGGGCGGGAGGGCCTT
CGTGCGTCGCCGCGCCGCCGTCCCCTTCTCCCTCTCCAGCCTCGGGGCTG
TCCGCGGGGGACGGCTGCCTTCGGGGGGACGGGGCAGGGCGGGGTTCG
GCTTCTGGCGTGTGACCGGCGGCTCTAGAGCCTCTGCTAACCATGTTCAT
GCCTTCTTCTTTTTCCTACAG(CBA sequence; SEQ ID NO:
37);

CTCCTGGGCAACGTGCTGGTTATTGTGACCGGTGCCACC(spacer;
SEQ ID NO: 38);

ATGTACCGGATGCAGCTGCTGAGCTGTATCGCCCTGTCTCTGGCCCTGGT
CACCAATTCT (IL-2 secretion signal sequence; SEQ ID
NO: 39);

GAGGTGCAGCTGGTGGAATCTGGCGGCGGACTTGTTCAACCTGGCGGCTC
TCTGAGACTGAGCTGTGCCGCTTCTGGCTACACCTTCACCAACTACGGCA
TGAACTGGGTCCGACAGGCCCCTGGCAAAGGCCTTGAATGGGTCGGATGG
ATCAACACCTACACCGGCGAGCCAACATACGCCGCCGACTTCAAGCGGAG
ATTCACCTTCAGCCTGGACACCAGCAAGAGCACCGCCTACCTGCAGATGA
ACAGCCTGAGAGCCGAGGACACCGCCGTGTACTACTGCGCCAAGTATCCC
CACTACTACGGCAGCAGCCACTGGTACTTTGACGTGTGGGGACAGGGCAC
ACTGGTCACAGTGTCTAGCGCCTCTACAAAGGGCCCCAGCGTTTTCCCAC
TGGCTCCTAGCAGCAAGTCTACCAGCGGAGGAACAGCCGCTCTGGGCTGT
CTGGTCAAGGACTACTTTCCCGAGCCTGTGACCGTGTCCTGGAATTCTGG
CGCTCTGACAAGCGGCGTGCACACCTTTCCAGCTGTGCTGCAAAGCAGCG
GCCTGTACTCTCTGAGCAGCGTCGTGACAGTGCCAAGCAGCTCTCTGGGC
ACCCAGACCTACATCTGCAATGTGAACCACAAGCCTAGCAACACCAAGGT
GGACAAGAAGGTGGAACCCAAGAGCTGCGACAAGACCCACACCTGTCCTC
CATGTCCTGCTCCAGAACTGCTCGGCGGACCTTCCGTGTTCCTGTTTCCT
CCAAAGCCTAAGGACACCCTGATGATCAGCAGAACCCCTGAAGTGACCTG
CGTGGTGGTGGATGTGTCCCACGAGGATCCCGAAGTGAAGTTCAATTGGT
ACGTGGACGGCGTGGAAGTGCACAACGCCAAGACCAAGCCTAGAGAGGAA
CAGTACAACAGCACCTACAGAGTGGTGTCCGTGCTGACCGTGCTGCACCA
GGATTGGCTGAACGGCAAAGAGTACAAGTGCAAGGTGTCCAACAAGGCCC
TGCCTGCTCCTATCGAGAAAACCATCAGCAAGGCCAAGGGCCAGCCTAGG
GAACCCCAGGTTTACACACTGCCTCCAAGCCGGGAAGAGATGACCAAGAA
CCAGGTGTCCCTGACCTGCCTCGTGAAGGGCTTCTACCCTTCCGATATCG
CCGTGGAATGGGAGAGCAATGGCCAGCCAGAGAACAACTACAAGACAACC
CCTCCTGTGCTGGACAGCGACGGCTCATTCTTCCTGTACAGCAAGCTGAC
AGTGGACAAGTCCAGATGGCAGCAGGGCAACGTGTTCAGCTGCAGCGTGA
TGCACGAGGCCCTGCACAACCACTACACCCAGAAGTCTCTGAGCCTGTCT
CCTGGCAAG(sequence encoding heavy chain of
bevacizumab; SEQ ID NO: 40);

CGGAAGAGAAGA(linker sequence; SEQ ID NO: 41);

GGCTCTGGCGAAGGCAGAGGCAGCCTGCTTACATGTGGCGACGTGGAAGA
GAACCCCGGACCT(T2A sequence; SEQ ID NO: 42);

ATGTATAGAATGCAGCTCCTGTCCTGCATTGCCCTGAGCCTGGCTCTCGT
GACCAACAGC(IL-2 secretion signal sequence; SEQ ID
NO: 43);

GACATCCAGATGACACAGAGCCCCAGCAGCCTGTCTGCCTCTGTGGGAGA
CAGAGTGACCATCACCTGTAGCGCCAGCCAGGACATCTCCAACTACCTGA
ACTGGTATCAGCAAAAGCCCGGCAAGGCCCCTAAGGTGCTGATCTACTTC
ACAAGCAGCCTGCACTCCGGCGTGCCCAGCAGATTTTCTGGCTCTGGCAG
CGGCACCGACTTCACCCTGACCATATCTAGCCTGCAGCCTGAGGACTTCG
CCACCTACTACTGCCAGCAGTACAGCACCGTGCCTTGGACATTTGGCCAG
GGCACAAAGGTGGAAATCAAGCGGACTGTGGCCGCTCCTAGCGTGTTCAT
CTTTCCACCTAGCGACGAGCAGCTGAAGTCTGGCACAGCCTCTGTCGTGT
GCCTGCTGAACAACTTCTACCCCAGAGAAGCCAAGGTGCAGTGGAAAGTG
GACAATGCCCTGCAGAGCGGCAACAGCCAAGAGAGCGTGACAGAGCAGGA
CTCCAAGGATAGCACCTATAGCCTGAGCAGCACCCTGACACTGAGCAAGG
CCGACTACGAGAAGCACAAAGTGTACGCCTGCGAAGTGACCCACCAGGGC
CTTTCTAGCCCTGTGACCAAGAGCTTCAACCGGGGCGAATGTTAA
(sequence encoding light chain of bevacizumab; SEQ
ID NO: 44);

GAGCTCGCTGATCAGCCTCGA(linker sequence; SEQ ID
NO: 45);

CTGTGCCTTCTAGTTGCCAGCCATCTGTTGTTTGCCCCTCCCCCGTGCCT
TCCTTGACCCTGGAAGGTGCCACTCCCACTGTCCTTTCCTAATAAAATGA

-continued
GGAAATTGCATCGCATTGTCTGAGTAGGTGTCATTCTATTCTGGGGGGTG

GGGTGGGGCAGGACAGCAAGGGGGAGGATTGGGAAGACAATAGCAGGCAT

GCTGGGGATGCGGTGGGCTCTATGG(bovine growth hormone polyA tail sequence; SEQ ID NO: 46);

AAGCTTGAATTCAGCTGACGTGCCTCGGACCGCT(linker sequence; SEQ ID NO: 47);
and

AGGAACCCCTAGTGATGGAGTTGGCCACTCCCTCTCTGCGCGCTCGCTCG

CTCACTGAGGCCGGGCGACCAAAGGTCGCCCGACGCCCGGGCTTTGCCCG

GGCGGCCTCAGTGAGCGAGCGAGCGCGCAGCTGCCTGCAGG(3' ITR;

SEQ ID NO: 48).

The IL-2 signal sequence encoded by each of SEQ ID NOs: 39 and 43 is MYRMQLLSCIALSLALVTNS (SEQ ID NO: 49). The T2A sequence encoded by SEQ ID NO: 42 is GSGEGRGSLLTCGDVEENPGP (SEQ ID NO: 50). SEQ ID NO: 40 encodes the heavy chain of bevacizumab (SEQ ID NO: 6). SEQ ID NO: 44 encodes the light chain of bevacizumab (SEQ ID NO: 5). The last three nucleotides in SEQ ID NO: 44 are a stop codon.

Figure 1B:
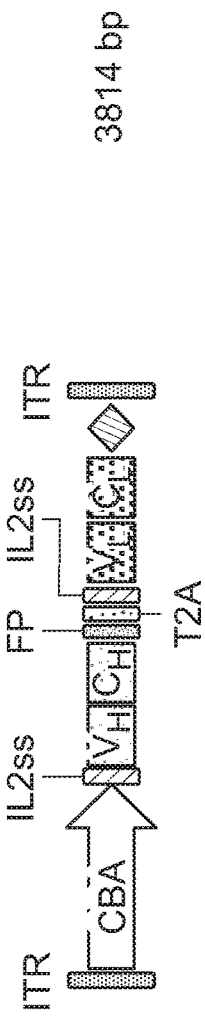
FIG. 1B is an exemplary AAV vector of 3814 bp that includes a sequence encoding ranibizumab (Lucentis®).

The vector in FIG. 1B is an exemplary AAV vector of 3814 bp (SEQ ID NO: 51) that includes the following sub-sequences going in the 5' to 3' direction:

CCTGCAGGCAGCTGCGCGCTCGCTCGCTCACTGAGGCCGCCCGGGCGTCG

GGCGACCTTTGGTCGCCCGGCCTCAGTGAGCGAGCGAGCGCGCAGAGAGG

GAGTGGCCAACTCCATCACTAGGGGTTCCTGCGGCCGCACGCGT(3'

ITR; SEQ ID NO: 36);

GACATTGATTATTGACTAGTTATTAATAGTAATCAATTACGGGGTCATTA

GTTCATAGCCCATATATGGAGTTCCGCGTTACATAACTTACGGTAAATGG

CCCGCCTGGCTGACCGCCCAACGACCCCCGCCCATTGACGTCAATAATGA

CGTATGTTCCCATAGTAACGCCAATAGGGACTTTCCATTGACGTCAATGG

GTGGACTATTTACGGTAAACTGCCCACTTGGCAGTACATCAAGTGTATCA

TATGCCAAGTACGCCCCCTATTGACGTCAATGACGGTAAATGGCCCGCCT

GGCATTATGCCCAGTACATGACCTTATGGGACTTTCCTACTTGGCAGTAC

ATCTACGTATTAGTCATCGCTATTACCATGGTCGAGGTGAGCCCCACGT

TCTGCTTCACTCTCCCCATCTCCCCCCCCTCCCCACCCCCAATTTTGTAT

TTATTTATTTTTTAATTATTTTGTGCAGCGATGGGGGCGGGGGGGGGGG

GGCGCGCGCCAGGCGGGCGGGCGGGCGAGGGCGGGCGGGGCGAGG

CGGAGAGGTGCGGCGGCAGCCAATCAGAGCGGCGCGCTCCGAAAGTTTCC

TTTTATGGCGAGGCGGCGGCGGCGGCGGCCCTATAAAAAGCGAAGCGCGC

GGCGGGCGGGAGTCGCTGCGTTGCCTTCGCCCCGTGCCCCGCTCCGCGCC

GCCTCGCGCCGCCCGCCCCGGCTCTGACTGACCGCGTTACTCCCACAGGT

GAGCGGGCGGGACGGCCCTTCTCCTCCGGGCTGTAATTAGCGCTTGGTTT

AATGACGGCTCGTTTCTTTTCTGTGGCTGCGTGAAAGCCTTAAAGGGCTC

CGGGAGGGCCCTTTGTGCGGGGGGAGCGGCTCGGGGGGTGCGTGCGTGT

GTGTGTGCGTGGGGAGCGCCGCGTGCGGCCCGCGCTGCCCGGCGGCTGTG

AGCGCTGCGGGCGCGGCGCGGGGCTTTGTGCGCTCCGCGTGTGCGCGAGG

GGAGCGCGGCCGGGGGCGGTGCCCCGCGGTGCGGGGGGGCTGCGAGGGGA

ACAAAGGCTGCGTGCGGGGTGTGTGCGTGGGGGGGTGAGCAGGGGGTGTG

GGCGCGGCGGTCGGGCTGTAACCCCCCCCTGCACCCCCCTCCCCGAGTTG

CTGAGCACGGCCCGGCTTCGGGTGCGGGCTCCGTGCGGGGCGTGGCGCG

GGGCTCGCCGTGCCGGGCGGGGGTGGCGGCAGGTGGGGGTGCCGGGCGG

GGCGGGGCCGCCTCGGGCCGGGAGGGCTCGGGGGAGGGGCGCGGCGGCC

CCCGGAGCGCCGGCGGCTGTCGAGGCGCGGCGAGCCGCAGCCATTGCCTT

TTATGGTAATCGTGCGAGAGGGCGCAGGGACTTCCTTTGTCCCAAATCTG

TGCGGAGCCGAAATCTGGGAGGCGCCGCCGCACCCCCTCTAGCGGGCGCG

GGGCGAAGCGGTGCGGCGCCGGCAGGAAGGAAATGGGCGGGGAGGGCCTT

CGTGCGTCGCCGCGCCGCCGTCCCCTTCTCCCTCTCCAGCCTCGGGGCTG

TCCGCGGGGGGACGGCTGCCTTCGGGGGGACGGGGCAGGGCGGGGTTCG

GCTTCTGGCGTGTGACCGGCGGCTCTAGAGCCTCTGCTAACCATGTTCAT

GCCTTCTTCTTTTTCCTACAG(CBA sequence; SEQ ID NO: 37);

CTCCTGGGCAACGTGCTGGTTATTGTGACCGGTGCCACC(linker sequence; SEQ ID NO: 38);

ATGTACCGGATGCAGCTGCTGAGCTGTATCGCCCTGTCTCTGGCCCTGGT

CACCAATTCT(IL-2 secretion signal sequence; SEQ ID

NO: 39);

GAGGTGCAGCTGGTGGAATCTGGCGGCGGACTTGTTCAACCTGGCGGCTC

TCTGAGACTGAGCTGTGCCGCTTCTGGCTACGACTTCACCCACTACGGCA

TGAACTGGGTCCGACAGGCCCCTGGCAAAGGCCTTGAATGGGTCGGATGG

ATCAACACCTACACCGGCGAGCCAACATACGCCGCCGACTTCAAGCGGAG

ATTCACCTTCAGCCTGGACACCAGCAAGAGCACCGCCTACCTGCAGATGA

ACAGCCTGAGAGCCGAGGACACCGCCGTGTACTACTGCGCCAAGTATCCC

TACTACTACGGCACCAGCCACTGGTACTTTGACGTGTGGGGACAGGGCAC

ACTGGTCACAGTGTCTAGCGCCTCTACAAAGGGCCCCAGCGTTTTCCCAC

TGGCTCCTAGCAGCAAGTCTACCAGCGGAGGAACAGCCGCTCTGGGCTGT

CTGGTCAAGGACTACTTTCCCGAGCCTGTGACCGTGTCCTGGAATTCTGG

CGCTCTGACAAGCGGCGTGCACACCTTTCCAGCTGTGCTGCAAAGCAGCG

GCCTGTACTCTCTGAGCAGCGTCGTGACAGTGCCAAGCAGCTCTCTGGGC

ACCCAGACCTACATCTGCAATGTGAACCACAAGCCTAGCAACACCAAGGT

GGACAAGAAGGTGGAACCCAAGAGCTGCGACAAGACCCACACCGGCAAG
(sequence encoding ranibizumab heavy chain; SEQ ID

NO: 52);

CGGAAGAGAAGA(linker sequence; SEQ ID NO: 41);

GGCTCTGGCGAAGGCAGAGGCAGCCTGCTTACATGTGGCGACGTGGAAGA

-continued

GAACCCCGGACCT(T2A sequence; SEQ ID NO: 42);

ATGTATAGAATGCAGCTCCTGTCCTGCATTGCCCTGAGCCTGGCTCTCGT

GACCAACAGC(IL-2 signal secretion sequence; SEQ ID

NO: 43);

GACATCCAGCTGACACAGAGCCCCAGCAGCCTGTCTGCCTCTGTGGGAGA

CAGAGTGACCATCACCTGTAGCGCCAGCCAGGACATCTCCAACTACCTGA

ACTGGTATCAGCAAAAGCCCGGCAAGGCCCCTAAGGTGCTGATCTACTTC

ACAAGCAGCCTGCACTCCGGCGTGCCCAGCAGATTTTCTGGCTCTGGCAG

CGGCACCGACTTCACCCTGACCATATCTAGCCTGCAGCCTGAGGACTTCG

CCACCTACTACTGCCAGCAGTACAGCACCGTGCCTTGGACATTTGGCCAG

GGCACAAAGGTGGAAATCAAGCGGACTGTGGCCGCTCCTAGCGTGTTCAT

CTTTCCACCTAGCGACGAGCAGCTGAAGTCTGGCACAGCCTCTGTCGTGT

GCCTGCTGAACAACTTCTACCCCAGAGAAGCCAAGGTGCAGTGGAAAGTG

GACAATGCCCTGCAGAGCGGCAACAGCCAAGAGAGCGTGACAGAGCAGGA

CTCCAAGGATAGCACCTATAGCCTGAGCAGCACCCTGACACTGAGCAAGG

CCGACTACGAGAAGCACAAAGTGTACGCCTGCGAAGTGACCCACCAGGGC

CTTTCTAGCCCTGTGACCAAGAGCTTCAACCGGGGCGAATGTTAA
(sequence encoding ranibizumab light chain; SEQ ID
NO: 53).

GAGCTCGCTGATCAGCCTCGA(linker sequence; SEQ ID NO:

45);

CTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGA

GGAAATTGCATCGCATTGTCTGAGTAGGTGTCATTCTATTCTGGGGGGTG

GGGTGGGGCAGGACAGCAAGGGGGAGGATTGGGAAGACAATAGCAGGCAT

GCTGGGGATGCGGTGGGCTCTATGG(bovine growth hormone polyA tail sequence; SEQ ID NO: 46);
and AAGCTTGAATTCAGCTGACGTGCCTCGGACCGCT(linker; SEQ ID

NO: 47);

AGGAACCCCTAGTGATGGAGTTGGCCACTCCCTCTCTGCGCGCTCGCTCG

CTCACTGAGGCCGGGCGACCAAAGGTCGCCCGACGCCCGGGCTTTGCCCG

GGCGGCCTCAGTGAGCGAGCGAGCGCGCAGCTGCCTGCAGG(SEQ ID

NO: 48).

The IL-2 signal sequence encoded by each of SEQ ID NOs: 39 and 43 is MYRMQLLSCIALSLALVTNS (SEQ ID NO: 49). The T2A sequence encoded by SEQ ID NO: 42 is GSGEGRGSLLTCGDVEENPGP (SEQ ID NO: 50). SEQ ID NO: 52 encodes the heavy chain of ranibizumab

SEQ ID NO: 53
(EVQLVESGGGLVQPGGSLRLSCAASGYDFTHYGMNWVRQAPGKGLEWVG

WINTYTGEPTYAADFKRRFTFSLDTSKSTAYLQMNSLRAEDTAVYYCAKY

PYYYGTSHWYFDVWGQGTLVTVSSASTKGPSVFPLAPSSKSTSGGTAALG

-continued

CLVKDYFPEPVTVSWNSGALTSGVHTFPAVLQSSGLYSLSSVVTVPSSSL

GTQTYICNVNHKPSNTKVDKKVEPKSCDKTHTGK; SEQ ID NO: 54).

encodes the light chain of bevacizumab (SEQ ID NO: 7). The last three nucleotides in SEQ ID NO: 53 are a stop codon.

Figure 1C:
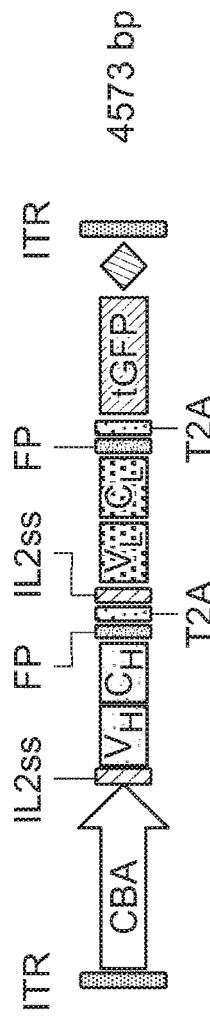
FIG. 1C is an exemplary AAV vector of 4573 bp that includes a sequence encoding ranibizumab and green fluorescent protein (GFP).

FIG. 1C is an exemplary AAV vector of 4573 bp (SEQ ID NO: 55) that includes the following sub-sequences going in the 5' to 3' direction:

CCTGCAGGCAGCTGCGCGCTCGCTCGCTCACTGAGGCCGCCCGGGCGTCG

GGCGACCTTTGGTCGCCCGGCCTCAGTGAGCGAGCGAGCGCGCAGAGAGG

GAGTGGCCAACTCCATCACTAGGGGTTCCTGCGGCCGCACGCGT(5'

ITR; SEQ ID NO: 36);

GACATTGATTATTGACTAGTTATTAATAGTAATCAATTACGGGGTCATTA

GTTCATAGCCCATATATGGAGTTCCGCGTTACATAACTTACGGTAAATGG

CCCGCCTGGCTGACCGCCCAACGACCCCCGCCCATTGACGTCAATAATGA

CGTATGTTCCCATAGTAACGCCAATAGGGACTTTCCATTGACGTCAATGG

GTGGACTATTTACGGTAAACTGCCCACTTGGCAGTACATCAAGTGTATCA

TATGCCAAGTACGCCCCCTATTGACGTCAATGACGGTAAATGGCCCGCCT

GGCATTATGCCCAGTACATGACCTTATGGGACTTTCCTACTTGGCAGTAC

ATCTACGTATTAGTCATCGCTATTACCATGGGTCGAGGTGAGCCCCACGT

TCTGCTTCACTCTCCCCATCTCCCCCCCCTCCCCACCCCCAATTTTGTAT

TTATTTATTTTTTAATTATTTTGTGCAGCGATGGGGGCGGGGGGGGGGG

GGCGCGCGCCAGGCGGGCGGGGCGGGGCGAGGGGCGGGGCGGGGCGAGG

CGGAGAGGTGCGGCGGCAGCCAATCAGAGCGGCGCGCTCCGAAAGTTTCC

TTTTATGGCGAGGCGGCGGCGGCGGCGGCCCTATAAAAAGCGAAGCGCGC

GGCGGGCGGGAGTCGCTGCGTTGCCTTCGCCCCGTGCCCGCTCCGCGCC

GCCTCGCGCCGCCCGCCCCGGCTCTGACTGACCGCGTTACTCCCACAGGT

GAGCGGGCGGGACGGCCCTTCTCCTCCGGGCTGTAATTAGCGCTTGGTTT

AATGACGGCTCGTTTCTTTTCTGTGGCTGCGTGAAAGCCTTAAAGGGCTC

CGGGAGGGCCCTTTGTGCGGGGGGAGCGGCTCGGGGGGTGCGTGCGTGT

GTGTGTGCGTGGGGAGCGCCGCGTGCGGCCCGCGCTGCCCGGCGGCTGTG

AGCGCTGCGGGCGCGGCGCGGGGCTTTGTGCGCTCCGCGTGTGCGCGAGG

GGAGCGCGGCCGGGGCGGTGCCCCGCGGTGCGGGGGGGCTGCGAGGGGA

ACAAAGGCTGCGTGCGGGGTGTGTGCGTGGGGGGGTGAGCAGGGGGTGTG

GGCGCGGCGGTCGGGCTGTAACCCCCCCCTGCACCCCCCTCCCCGAGTTG

CTGAGCACGGCCCGGCTTCGGGTGCGGGGCTCCGTGCGGGGCGTGGCGCG

GGGCTCGCCGTGCCGGGCGGGGGTGGCGGCAGGTGGGGGTGCCGGGCGG

GGCGGGGCGCCTCGGGCCGGGGAGGGCTCGGGGAGGGGCGCGGCGGCC

CCCGGAGCGCCGGCGGCTGTCGAGGCGCGGCGAGCCGCAGCCATTGCCTT

TTATGGTAATCGTGCGAGAGGGCGCAGGGACTTCCTTTGTCCCAAATCTG

TGCGGAGCCGAAATCTGGGAGGCGCCGCCGCACCCCCTCTAGCGGGCGCG

GGGCGAAGCGGTGCGGCGCCGGCAGGAAGGAAATGGGCGGGGAGGGCCTT
CGTGCGTCGCCGCGCCGCCGTCCCCTTCTCCCTCTCCAGCCTCGGGGCTG
TCCGCGGGGGGACGGCTGCCTTCGGGGGGGACGGGGCAGGGCGGGGTTCG
GCTTCTGGCGTGTGACCGGCGGCTCTAGAGCCTCTGCTAACCATGTTCAT
GCCTTCTTCTTTTTCCTACAG(CBA sequence; SEQ ID NO: 37);
CTCCTGGGCAACGTGCTGGTTATTGTGACCGGTGCCACC(linker
sequence; SEQ ID NO: 38);
ATGTACCGGATGCAGCTGCTGAGCTGTATCGCCCTGTCTCTGGCCCTGGT
CACCAATTCT(IL-2 secretion signal sequence; SEQ ID
NO: 39);
GAGGTGCAGCTGGTGGAATCTGGCGGCGGACTTGTTCAACCTGGCGGCTC
TCTGAGACTGAGCTGTGCCGCTTCTGGCTACGACTTCACCCACTACGGCA
TGAACTGGGTCCGACAGGCCCCTGGCAAAGGCCTTGAATGGGTCGGATGG
ATCAACACCTACACCGGCGAGCCAACATACGCCGCCGACTTCAAGCGGAG
ATTCACCTTCAGCCTGGACACCAGCAAGAGCACCGCCTACCTGCAGATGA
ACAGCCTGAGAGCCGAGGACACCGCCGTGTACTACTGCGCCAAGTATCCC
TACTACTACGGCACCAGCCACTGGTACTTTGACGTGTGGGGACAGGGCAC
ACTGGTCACAGTGTCTAGCGCCTCTACAAAGGGCCCCAGCGTTTTCCCAC
TGGCTCCTAGCAGCAAGTCTACCAGCGGAGGAACAGCCGCTCTGGGCTGT
CTGGTCAAGGACTACTTTCCCGAGCCTGTGACCGTGTCCTGGAATTCTGG
CGCTCTGACAAGCGGCGTGCACACCTTTCCAGCTGTGCTGCAAAGCAGCG
GCCTGTACTCTCTGAGCAGCGTCGTGACAGTGCCAAGCAGCTCTCTGGGC
ACCCAGACCTACATCTGCAATGTGAACCACAAGCCTAGCAACACCAAGGT
GGACAAGAAGGTGGAACCCAAGAGCTGCGACAAGACCCACACCGGCAAG
(sequence encoding ranibizumab heavy chain; SEQ ID
NO: 52);
CGGAAGAGAAGA(linker sequence; SEQ ID NO: 41);
GGCTCTGGCGAAGGCAGAGGCAGCCTGCTTACATGTGGCGACGTGGAAGA
GAACCCCGGACCT(T2A sequence;SEQ ID NO: 42);
ATGTATAGAATGCAGCTCCTGTCCTGCATTGCCCTGAGCCTGGCTCTCGT
GACCAACAGC(IL-2 signal secretion sequence; SEQ ID
NO: 43);
GACATCCAGCTGACACAGAGCCCCAGCAGCCTGTCTGCCTCTGTGGGAGA
CAGAGTGACCATCACCTGTAGCGCCAGCCAGGACATCTCCAACTACCTGA
ACTGGTATCAGCAAAAGCCCGGCAAGGCCCCTAAGGTGCTGATCTACTTC
ACAAGCAGCCTGCACTCCGGCGTGCCCAGCAGATTTTCTGGCTCTGGCAG
CGGCACCGACTTCACCCTGACCATATCTAGCCTGCAGCCTGAGGACTTCG
CCACCTACTACTGCCAGCAGTACAGCACCGTGCCTTGGACATTTGGCCAG
GGCACAAAGGTGGAAATCAAGCGGACTGTGGCCGCTCCTAGCGTGTTCAT
CTTTCCACCTAGCGACGAGCAGCTGAAGTCTGGCACAGCCTCTGTCGTGT
GCCTGCTGAACAACTTCTACCCCAGAGAAGCCAAGGTGCAGTGGAAAGTG
GACAATGCCCTGCAGAGCGGCAACAGCCAAGAGAGCGTGACAGAGCAGGA
CTCCAAGGATAGCACCTATAGCCTGAGCAGCACCCTGACACTGAGCAAGG
CCGACTACGAGAAGCACAAAGTGTACGCCTGCGAAGTGACCCACCAGGGC
CTTTCTAGCCCTGTGACCAAGAGCTTCAACCGGGGCGAATGT
(sequence encoding ranibizumab light chain; SEQ ID
NO: 56);
GGCTCCGGAGAGGGCAGAGGAAGTCTGCTAACATGCGGTGACGTCGAGGA
GAATCCTGGCCCA(linker sequence; SEQ ID NO: 57);
ATGGAGAGCGACGAGAGCGGCCTGCCCGCCATGGAGATCGAGTGCCGCAT
CACCGGCACCCTGAACGGCGTGGAGTTCGAGCTGGTGGGCGGCGGAGAGG
GCACCCCCGAGCAGGGCCGCATGACCAACAAGATGAAGAGCACCAAAGGC
GCCCTGACCTTCAGCCCCTACCTGCTGAGCCACGTGATGGGCTACGGCTT
CTACCACTTCGGCACCTACCCCAGCGGCTACGAGAACCCCTTCCTGCACG
CCATCAACAACGGCGGCTACACCAACACCCGCATCGAGAAGTACGAGGAC
GGCGGCGTGCTGCACGTGAGCTTCAGCTACCGCTACGAGGCCGGCCGCGT
GATCGGCGACTTCAAGGTGATGGGCACCGGCTTCCCCGAGGACAGCGTGA
TCTTCACCGACAAGATCATCCGCAGCAACGCCACCGTGGAGCACCTGCAC
CCCATGGGCGATAACGATCTGGATGGCAGCTTCACCCGCACCTTCAGCCT
GCGCGACGGCGGCTACTACAGCTCCGTGGTGGACAGCCACATGCACTTCA
GAGCGCCATCCACCCCAGCATCCTGCAGAACGGGGGCCCCATGTTCGCC
TTCCGCCGCGTGGAGGAGGATCACAGCAACACCGAGCTGGGCATCGTGGA
GTACCAGCACGCCTTCAAGACCCCGGATGCAGATGCCGGTGAAGAATAA
(sequence encoding Turbo GFP; SEQ ID NO: 58);
GAGCTCGCTGATCAGCCTCGA(linker sequence; SEQ ID NO:
45);
CTGTGCCTTCTAGTTGCCAGCCATCTGTTGTTTGCCCCTCCCCCGTGCCT
TCCTTGACCCTGGAAGGTGCCACTCCCACTGTCCTTTCCTAATAAAATGA
GGAAATTGCATCGCATTGTCTGAGTAGGTGTCATTCTATTCTGGGGGGTG
GGGTGGGGCAGGACAGCAAGGGGGAGGATTGGGAAGACAATAGCAGGCAT
GCTGGGGATGCGGTGGGCTCTATGG(bovine growth hormone
polyA tail sequence; SEQ ID NO: 46);
AAGCTTGAATTCAGCTGACGTGCCTCGGACCGCT(linker
sequence; SEQ ID NO: 47);
and
AGGAACCCCTAGTGATGGAGTTGGCCACTCCCTCTCTGCGCGCTCGCTCG
CTCACTGAGGCCGGGCGACCAAAGGTCGCCCGACGCCCGGGCTTTGCCCG
GGCGGCCTCAGTGAGCGAGCGAGCGCGCAGCTGCCTGCAGG(3' ITR;
SEQ ID NO: 48).

The IL-2 signal sequence encoded by each of SEQ ID NOs: 39 and 43 is MYRMQLLSCIALSLALVTNS (SEQ ID NO: 49). The T2A sequence encoded by SEQ ID NO: 42 is GSGEGRGSLLTCGDVEENPGP (SEQ ID NO: 50). SEQ ID NO: 52 encodes the heavy chain of ranibizumab (SEQ ID NO: 54). SEQ ID NO: 56 encodes the light chain of bevacizumab (SEQ ID NO: 7). SEQ ID NO: 58 encodes TurboGFP (MESDESGLPAMEIECRITGTLNGVEFELVGGGEGTPEQGRMTNKMKSTKGA LTFSPYLLSHVMGYGFYHFGTYPSGYENPFLHAINNGGYTNTRIEKYEDGGV LHVSFSYRYEAGRVIGDFKVMGTGFPEDSVIFTDKIIRSNATVEHLHPMGDND LDGSFTRTFSLRDGGYYSSVVDSHMHFKSAIHPSILQNGGPMFAFRRVEEDHS NTELGIVEYQHAFKTPDADAGEE; SEQ ID NO: 59). The last three nucleotides in SEQ ID NO: 58 is a stop codon.

Figure 1D:
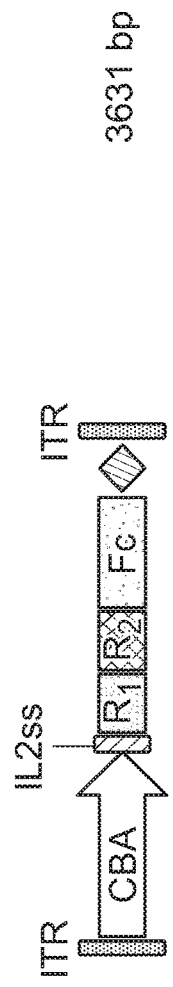
FIG. 1D is an exemplary AAV vector of 3631 bp that includes a sequence encoding aflibercept (Eylea®).

FIG. 1D is an exemplary AAV vector of 3631 bp (SEQ ID NO: 60) that includes the following sub-sequences going in the 5' to 3' direction:

CCTGCAGGCAGCTGCGCGCTCGCTCGCTCACTGAGGCCGCCCGGGCGTCG

GGCGACCTTTGGTCGCCCGGCCTCAGTGAGCGAGCGAGCGCGCAGAGAGG

GAGTGGCCAACTCCATCACTAGGGGTTCCTGCGGCCGCACGCGT(5'

ITR; SEQ ID NO: 36);

GACATTGATTATTGACTAGTTATTAATAGTAATCAATTACGGGGTCATTA

GTTCATAGCCCATATATGGAGTTCCGCGTTACATAACTTACGGTAAATGG

CCCGCCTGGCTGACCGCCCAACGACCCCCGCCCATTGACGTCAATAATGA

CGTATGTTCCCATAGTAACGCCAATAGGGACTTTCCATTGACGTCAATGG

GTGGACTATTTACGGTAAACTGCCCACTTGGCAGTACATCAAGTGTATCA

TATGCCAAGTACGCCCCCTATTGACGTCAATGACGGTAAATGGCCCGCCT

GGCATTATGCCCAGTACATGACCTTATGGGACTTTCCTACTTGGCAGTAC

ATCTACGTATTAGTCATCGCTATTACCATGGTCGAGGTGAGCCCCACGT

TCTGCTTCACTCTCCCCATCTCCCCCCCCTCCCCACCCCCAATTTTGTAT

TTATTTATTTTTTAATTATTTTGTGCAGCGATGGGGGCGGGGGGGGGGG

GGCGCGCGCCAGGCGGGGCGGGGCGGGGCGAGGGCGGGGCGGGGCGAGG

CGGAGAGGTGCGGCGGCAGCCAATCAGAGCGGCGCGCTCCGAAAGTTTCC

TTTTATGGCGAGGCGGCGGCGGCGGCCCTATAAAAAGCGAAGCGCGC

GGCGGGCGGGAGTCGCTGCGTTGCCTTCGCCCCGTGCCCCGCTCCGCGCC

GCCTCGCGCCGCCCGCCCCGGCTCTGACTGACCGCGTTACTCCCACAGGT

GAGCGGGCGGGACGGCCCTTCTCCTCCGGGCTGTAATTAGCGCTTGGTTT

AATGACGGCTCGTTTCTTTTCTGTGGCTGCGTGAAAGCCTTAAAGGGCTC

CGGGAGGGCCCTTTGTGCGGGGGGGAGCGGCTCGGGGGGTGCGTGCGTGT

GTGTGTGCGTGGGGAGCGCCGCGTGCGGCCCGCGCTGCCCGGCGGCTGTG

AGCGCTGCGGGCGCGGCGCGGGGCTTTGTGCGCTCCGCGTGTGCGCGAGG

GGAGCGCGGCCGGGGCGGTGCCCCGCGGTGCGGGGGGGCTGCGAGGGGA

ACAAAGGCTGCGTGCGGGTGTGTGCGTGGGGGGTGAGCAGGGGGTGTG

GGCGCGGCGGTCGGGCTGTAACCCCCCCCTGCACCCCCCTCCCCGAGTTG

CTGAGCACGGCCCGGCTTCGGGTGCGGGCTCCGTGCGGGGCGTGGCGCG

GGGCTCGCCGTGCCGGGCGGGGGTGGCGGCAGGTGGGGGTGCCGGGCGG

GGCGGGGCCGCCTCGGGCCGGGGAGGGCTCGGGGAGGGGCGCGGCGGCC

CCCGGAGCGCCGGCGGCTGTCGAGGCGCGGCGAGCCGCAGCCATTGCCTT

TTATGGTAATCGTGCGAGAGGGCGCAGGGACTTCCTTTGTCCCAAATCTG

TGCGGAGCCGAAATCTGGGAGGCGCCGCCGCACCCCCTCTAGCGGGCGCG

GGGCGAAGCGGTGCGGCGCCGGCAGGAAGGAAATGGGCGGGGAGGGCCTT

CGTGCGTCGCCGCGCCGCCGTCCCCTTCTCCCTCTCCAGCCTCGGGCTG

TCCGCGGGGGGACGGCTGCCTTCGGGGGGGACGGGGCAGGGCGGGGTTCG

GCTTCTGGCGTGTGACCGGCGGCTCTAGAGCCTCTGCTAACCATGTTCAT

GCCTTCTTCTTTTTCCTACAG(CBA sequence; SEQ ID NO: 37);

CTCCTGGGCAACGTGCTGGTTATTGTGACCGGTGCCACC(spacer;

SEQ ID NO: 38);

ATGTACCGGATGCAGCTGCTGAGCTGTATCGCCCTGTCTCTGGCCCTGGT

CACCAATTCT(IL-2 secretion signal sequence; SEQ ID

NO: 39);

AGCGATACCGGCAGACCCTTCGTGGAAATGTACAGCGAGATCCCCGAGAT

CATCCACATGACCGAGGGCAGAGAGCTGGTCATCCCCTGCAGAGTGACAA

GCCCCAACATCACCGTGACTCTGAAGAAGTTCCCTCTGGACACACTGATC

CCCGACGGCAAGAGAATCATCTGGGACAGCCGGAAGGGCTTCATCATCAG

CAACGCACCTACAAAGAGATCGGCCTGCTGACCTGTGAAGCCACCGTGA

ATGGCCACCTGTACAAGACCAACTACCTGACACACAGACAGACCAACACC

ATCATCGACGTGGTGCTGAGCCCTAGCCACGGCATTGAACTGTCTGTGGG

CGAGAAGCTGGTGCTGAACTGTACCGCCAGAACCGAGCTGAACGTGGGCA

TCGACTTCAACTGGGAGTACCCCAGCAGCAAGCACCAGCACAAGAAACTG

GTCAACGGGACCTGAAAACCCAGAGCGGCAGCGAGATGAAGAAATTCCT

GAGCACCCTGACCATCGACGGCGTGACCAGATCTGACCAGGGCCTGTACA

CATGTGCCGCCAGCTCTGGCCTGATGACCAAGAAAAACAGCACCTTCGTG

CGGGTGCACGAGAAGGACAAGACCCACACCTGTCCTCCATGTCCTGCTCC

AGAACTGCTCGGCGGACCTTCCGTGTTCCTGTTTCCTCCAAAGCCTAAGG

ACACCCTGATGATCAGCAGAACCCCTGAAGTGACCTGCGTGGTGGTGGAT

GTGTCCCACGAGGATCCCGAAGTGAAGTTCAATTGGTACGTGGACGGCGT

GGAAGTGCACAACGCCAAGACCAAGCCTAGAGAGGAACAGTACAATAGCA

CCTACAGAGTGGTGTCCGTGCTGACCGTGCTGCACCAGGATTGGCTGAAC

GGCAAAGAGTACAAGTGCAAGGTGTCCAACAAGGCCCTGCCTGCTCCTAT

CGAGAAAACCATCTCCAAGGCCAAGGGCCAGCCTAGGGAACCCCAGGTTT

ACACACTGCCTCCAAGCAGGGACGAGCTGACAAAGAACCAGGTGTCCCTG

ACCTGCCTGGTCAAGGGCTTCTACCCTTCCGATATCGCCGTGGAATGGGA

GAGCAATGGCCAGCCTGAGAACAACTACAAGACAACCCCTCCTGTGCTGG

ACAGCGACGGCTCATTCTTCCTGTACAGCAAGCTGACAGTGGACAAGAGC

-continued

```
AGATGGCAGCAGGGCAACGTGTTCAGCTGCAGCGTGATGCACGAGGCCCT

GCACAACCACTACACCCAGAAGTCCCTGAGCCTGTCTCCTGGATAA (sequence encoding a flibercept; SEQ ID NO: 61);

GAGCTCGCTGATCAGCCTCGA(linker sequence; SEQ ID NO:

45);

CTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGA

GGAAATTGCATCGCATTGTCTGAGTAGGTGTCATTCTATTCTGGGGGGTG

GGGTGGGGCAGGACAGCAAGGGGGAGGATTGGGAAGACAATAGCAGGCAT

GCTGGGGATGCGGTGGGCTCTATGG(bovine growth hormone polyA tail sequence; SEQ ID NO: 46);

AAGCTTGAATTCAGCTGACGTGCCTCGGACCGCT(linker sequence; SEQ ID NO: 47);
and

AGGAACCCCTAGTGATGGAGTTGGCCACTCCCTCTCTGCGCGCTCGCTCG

CTCACTGAGGCCGGGCGACCAAAGGTCGCCCGACGCCCGGGCTTTGCCCG

GGCGGCCTCAGTGAGCGAGCGAGCGCGCAGCTGCCTGCAGG(3' ITR;

SEQ ID NO: 48).
```

The IL-2 signal sequence encoded by SEQ ID NO: 39 is MYRMQLLSCIALSLALVTNS (SEQ ID NO: 49). SEQ ID NO: 61 encodes aflibercept (SEQ ID NO: 12). The last three nucleotides in SEQ ID NO: 61 is a stop codon.

To determine protein expression driven by the AAV vectors shown in FIGS. 1A-1C, HEK293FT cells were seeded overnight at $7 \times 10^4$ cells/well (400 µL per well) in wells of a 24-well plate. HEK293FT cells were transfected at ~800 ng with the AAV vectors shown in FIGS. 1A-1D using a Jetprime Polypus reagent (used to generate the data in Lanes 2-5 and 10-13 of FIG. 2). HEK293FT cells were also seeded for six hours at $4 \times 10^4$ cells/well (50 µL per well) in wells of a 96-well plate in the presence of 2 µM etoposide (used to generate the data in Lanes 6-8 and 14-16 of FIG. 2). The AAV vector shown in FIG. 1A was added into the media with a multiplicity of infection (MOI) of $7.5 \times 10^4$, $2.2 \times 10^5$, or $5.5 \times 10^5$. The supernatant was harvested at 72 hours post-treatment from well and was loaded onto a 4-12% Bolt protein gel in reducing (lanes 2-8 of FIG. 2) and non-reducing conditions (lanes 10-16 of FIG. 2). An anti-ranibizumab antibody detecting the Fab region was used as a primary antibody, and anti-human IgG was used as the second antibody.

Figure 2:
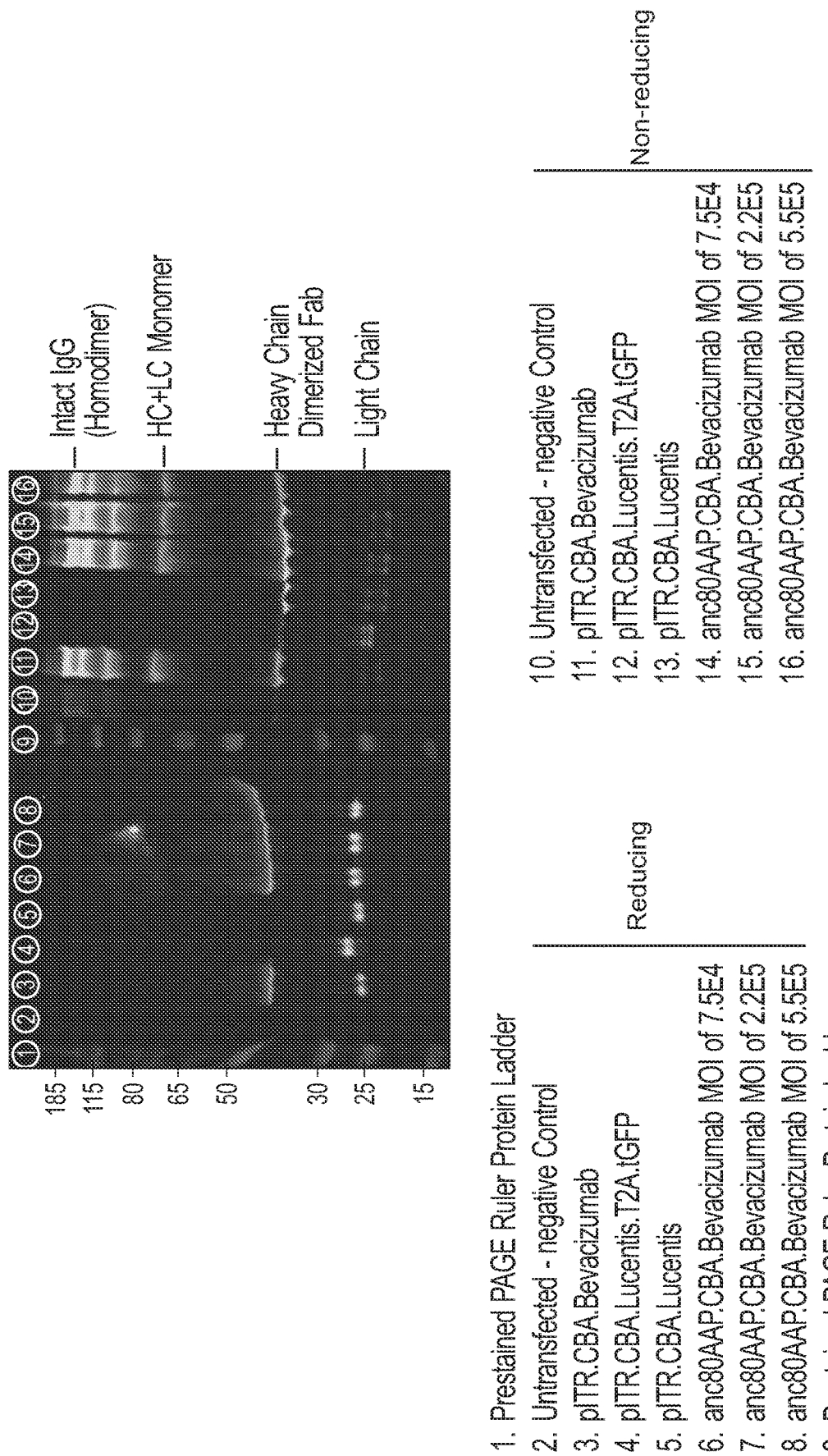
FIG. 2 is a Western blot showing HEK cell expression of different anti-VEGF antibodies or antigen-binding antibody fragments, or soluble VEGF receptors using exemplary AAV vectors described herein. Lane 1: pre-stained PageRuler™ protein ladder. Lane 2: untransfected/negative control. Lane 3: tranfection with the AAV vector shown in FIG. 1A. Lane 4: transfection with the AAV vector shown in FIG. 1C. Lane 5: transfection with the AAV vector shown in FIG. 1B. Lane 6: transfection with the AAV vector shown in FIG. 1A with an multiplicity of infection (MOI) of $7.5 \times 10^4$. Lane 7: transfection with the AAV vector shown in FIG. 1A with an MOI of $2.2 \times 10^5$. Lane 8: transfection with the AAV vector shown in FIG. 1A with an MOI of $5.5 \times 10^5$. Lane 9: prestained PageRuler™ protein ladder. Lane 10: untransfected/negative control. Lane 11: tranfection with the AAV vector shown in FIG. 1A. Lane 12: transfection with the AAV vector shown in FIG. 1C. Lane 13: transfection with the AAV vector shown in FIG. 1B. Lane 14: transfection with the AAV vector shown in FIG. 1A with an multiplicity of infection (MOI) of $7.5 \times 10^4$. Lane 15: transfection with the AAV vector shown in FIG. 1A with an MOI of $2.2 \times 10^5$. Lane 16: transfection with the AAV vector shown in FIG. 1A with an MOI of $5.5 \times 10^5$. Lanes 2-8 contain reduced proteins. Lanes 10-16 contain non-reduced proteins.

As shown in FIG. 2, the heavy chain and light chain ranibizumab were detected in Lanes 3 and 6-8, and intact ranibizumab (heterodimer) was detected in lanes 11 and 14-16.

Example 2. Binding Activity of Anti-Human VEGF Monoclonal Antibodies

Figure 3A:
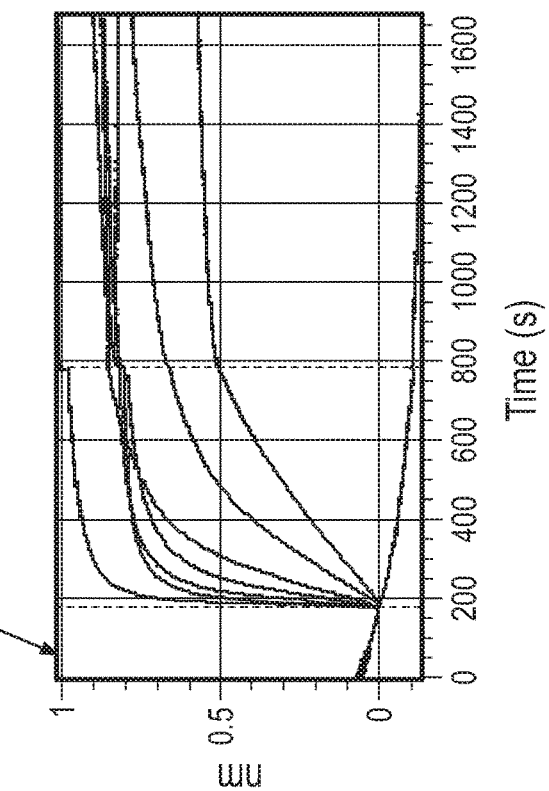
FIG. 3A is a graph showing the affinity of a control mouse anti-human VEGF monoclonal antibody (anti-hVEGF MmAb) in a buffer using recombinant human VEGF as the binding agent, as measured by Octet® HTX biosensor instrument using the Octet® analysis software, Data Analysis HT10.0.
Figure 3B:
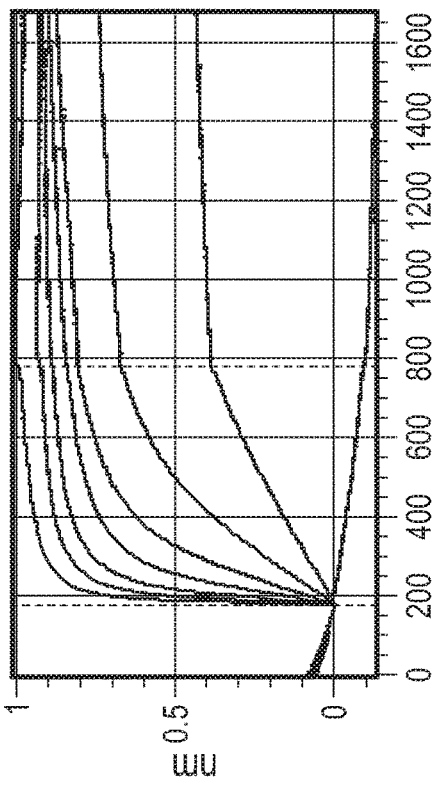
FIG. 3B is a graph showing the affinity of a control anti-hVEGF MmAb in conditioned media (CM) samples using recombinant human VEGF as the binding agent, as measured by Octet® HTX biosensor instrument using the Octet® analysis software, Data Analysis HT10.0. *: anti-hVEGF MmAb was prepared in CM at 100 μg/mL, then diluted to a final concentration of 10 μg/mL in 1× kinetics buffer.
Figures 4A, 4B:
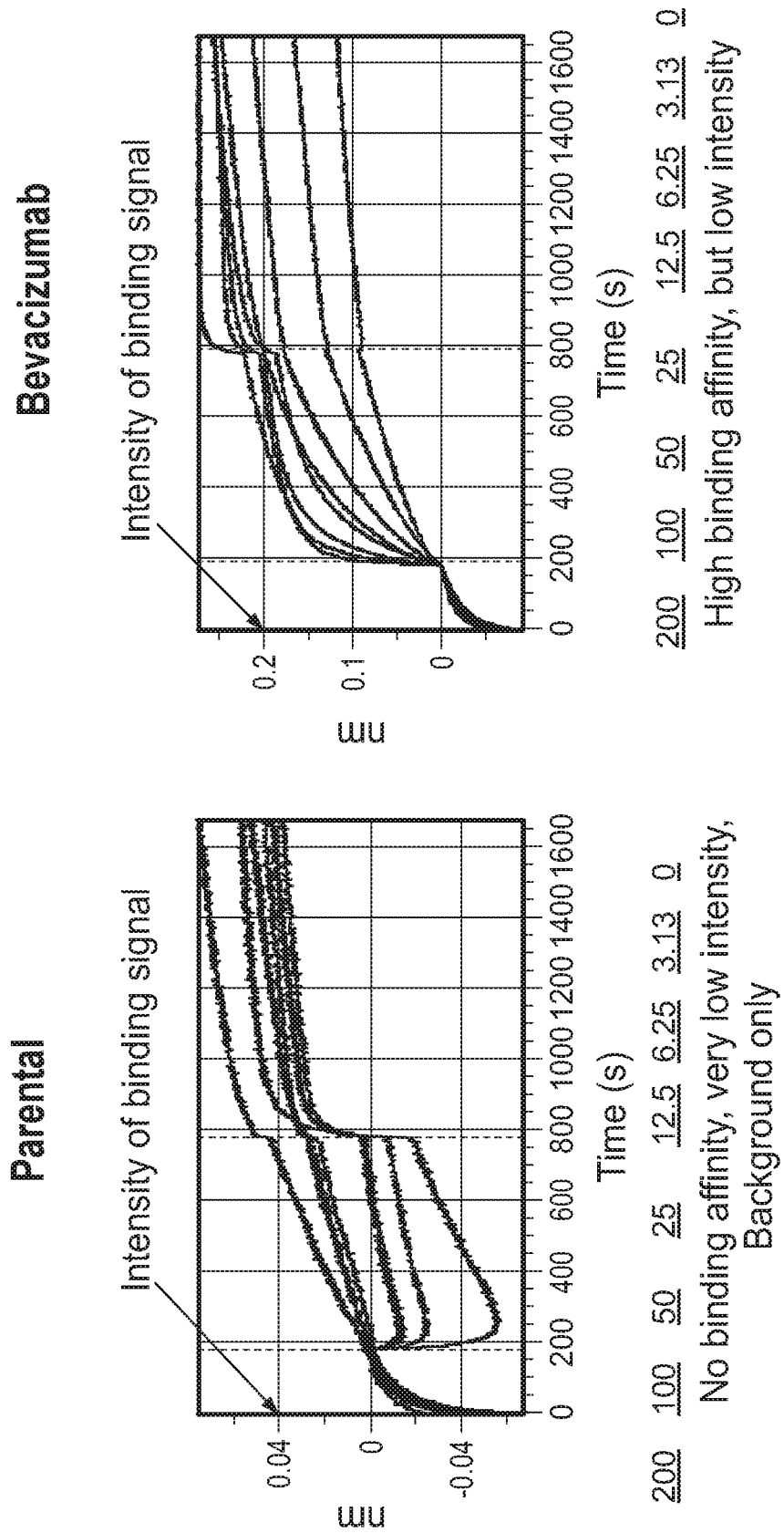
FIG. 4A is a graph showing the affinity of conditioned medium using recombinant human VEGF as the binding agent, as measured by Octet® HTX biosensor instrument using the Octet® analysis software, Data Analysis HT10.0.
FIG. 4B is a graph showing the affinity of culture medium from HEK cells transfected with the AAV vector shown in FIG. 1A using recombinant human VEGF as the binding agent, using by Octet® HTX biosensor instrument using the Octet® analysis software, Data Analysis HT10.0.

A set of experiments were performed to determine the binding activity of bevacizumab produced in HEK293FT cells following transfection with the AAV vector shown in FIG. 1A. A first set of control experiments were performed to calibrate the plasmon surface resonance instrumentation (using a mouse anti-human VEGF monoclonal antibody (anti-hVEGF MmAb; R&D, MAB293-100) in buffer or in conditioned medium (FIGS. 3A and 3B, respectivey) using recombinant human VEGF as the binding agent. A second set of experiments were performed to determine the human VEGF-binding activity of control conditioned medium and conditioned medium from HEK293TF cells following transfection with the AAV vector shown in FIG. 1A (FIGS. 4A and 4B, respectively).

The samples, bevacizumab in medium from HEK293TF cells transfected with the AAV vector shown in FIG. 1A or conditioned medium), were prepared by diluting 1:10 in 1× kinetics buffer (Fortebio, 18-1105) into a 384-well sample plate. Anti-hVEGF MmAb (R&D, MAB293-100) was diluted at a concentration of 10 µg/mL as a positive control. The capture agent, recombinant human VEGF (R&D, 293-VE-010) was diluted in a series of 1:2 dilution ratio from 200 nM to 3.125 nM.

The binding affinities of the conditioned medium samples and mouse anti-human VEGF antibody (R&D) samples were measured in 1× kinetics buffer in Octet® HTX biosensor instrument. The binding features and $K_D$ values were generated by the Octet® analysis software, Data Analysis HT10.0. As shown in FIGS. 3A-B, the $K_D$ of anti-hVEGF MmAb in buffer was $<1.0 \times 10^{-12}$ M, and the anti-hVEGF MmAb in conditioned medium was $<1.0 \times 10^{-12}$ M. The conditioned medium itself had no binding affinity and very low intensity (background signal only) (FIG. 4A). In contrast, the conditioned medium including bevacizumab produced by HEK293TF cells transfected with the AAV vector shown in FIG. 1A had high binding affinity, but low intensity (FIG. 4B; $K_D < 1.0 \times 10^{-12}$ M). FIG. 4C shows a table of the loading samples and the respective $K_D$, $K_D$ errors, equilibrium association constant ($k_a$), and the dissociation ($k_{dis}$), and $k_{dis}$ error.

In summary, the anti-hVEGF mouse antibody (R&D) showed high binding affinity ($K_D$ was lower than measurable range of $1.0 \times 10^{-12}$ M). The bevacizumab conditioned medium sample showed high binding affinity ($K_D$ was lower than measurable range). No $K_D$ value could be extrapolated from the binding data of control conditioned medium sample.

In sum, these data show that the AAV vectors provided herein can result in expression and secretion of anti-VEGF antibodies and can be used to express anti-VEGF antibodies in the inner ear of a mammal.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All publications, patent applications, patents, and other references mentioned herein are incorporated by reference in their entirety. In case of conflict, the present specification, including definitions, will control. Section headings and any descriptions of materials, methods, and examples are illustrative only and not intended to be limiting.

What is claimed is:

1. A composition formulated for delivery to the inner ear, wherein the composition comprises an adeno-associated virus (AAV) vector and the AAV vector comprises a nucleotide sequence that comprises:

a coding sequence that encodes a polypeptide, wherein the polypeptide comprises one or more soluble vascular endothelial growth factor (VEGF) receptors or a portion thereof and the coding sequence comprises the sequence of SEQ ID NO: 61, and wherein the polypeptide is operably linked to a signal peptide;

wherein the polypeptide specifically binds to one or more mammalian VEGF proteins.

2. The composition of claim 1, wherein the nucleotide sequence comprises a promoter, a Kozak sequence, or both.

3. The composition of claim 2, wherein the promoter is an inducible promoter, a constitutive promoter, or a tissue-specific promoter.

4. The composition of claim 3, wherein the promoter is a CAG promoter, a CBA promoter, or a CMV promoter.

5. The composition of claim 1, wherein the nucleotide sequence further comprises a polyadenylation signal sequence.

6. The composition of claim 1, wherein the signal peptide comprises an IL2 signal peptide.

7. The composition of claim 2, wherein the nucleotide sequence further comprises two AAV inverted terminal repeats (ITRs), and wherein the two AAV ITRs flank the coding sequence and promoter.

8. The composition of claim 7, wherein the two AAV ITRs are or are derived from AAV2 ITRs.

9. A cell comprising an adeno-associated virus (AAV) vector comprising a nucleotide sequence that comprises:
   a coding sequence that encodes a polypeptide, wherein the polypeptide comprises one or more soluble vascular endothelial growth factor (VEGF) receptors or a portion thereof and the coding sequence comprises the sequence of SEQ ID NO: 61, and wherein the polypeptide is operably linked to a signal peptide;
   wherein the polypeptide specifically binds to one or more mammalian VEGF proteins.

10. A method of treating an inner ear disorder in a mammal, comprising:
   administering an AAV vector comprising a nucleotide sequence that comprises:
   a coding sequence that encodes a polypeptide, wherein the polypeptide comprises one or more soluble vascular endothelial growth factor (VEGF) receptors or a portion thereof and the coding sequence comprises the sequence of SEQ ID NO: 61, and wherein the polypeptide is operably linked to a signal peptide and wherein the polypeptide specifically binds to one or more mammalian VEGF proteins;
   wherein the polypeptide specifically binds to one or more mammalian VEGF proteins.

11. The composition of claim 1, wherein the polypeptide comprises the amino acid sequence of SEQ ID NO: 12.

12. A pharmaceutical composition comprising an adeno-associated virus (AAV) vector comprising a nucleotide sequence that comprises:
   a coding sequence that encodes a polypeptide, wherein the polypeptide comprises one or more soluble vascular endothelial growth factor (VEGF) receptors or a portion thereof and the coding sequence comprises the sequence of SEQ ID NO: 61, and wherein the polypeptide is operably linked to a signal peptide;
   wherein the polypeptide specifically binds to one or more mammalian VEGF proteins, and wherein the pharmaceutical composition is formulated for delivery to the inner ear.

13. The pharmaceutical composition of claim 12, further comprising one or more pharmaceutically acceptable carriers or excipients.

14. The method of claim 10, wherein the inner ear disorder is vestibular schwannoma or neurofibromatosis type II (NF2).

15. The method of claim 10, wherein the AAV vector is in a composition and is delivered via intra-cochlear administration.

* * * * *